US008697877B2

(12) United States Patent
Sudo et al.

(10) Patent No.: US 8,697,877 B2
(45) Date of Patent: Apr. 15, 2014

(54) OXYINDOLE DERIVATIVES WITH MOTILIN RECEPTOR AGONISTIC ACTIVITY

(75) Inventors: Masaki Sudo, Aichi (JP); Yasuhiro Iwata, Aichi (JP); Yoshimasa Arano, Aichi (JP); Madoka Jinno, Aichi (JP); Masashi Ohmi, Aichi (JP); Hirohide Noguchi, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 122 days.

(21) Appl. No.: 13/203,301

(22) PCT Filed: Mar. 1, 2010

(86) PCT No.: PCT/JP2010/001368
§ 371 (c)(1),
(2), (4) Date: Sep. 9, 2011

(87) PCT Pub. No.: WO2010/098145
PCT Pub. Date: Sep. 2, 2010

(65) Prior Publication Data
US 2011/0312933 A1    Dec. 22, 2011

Related U.S. Application Data

(60) Provisional application No. 61/202,430, filed on Feb. 27, 2009, provisional application No. 61/282,173, filed on Dec. 24, 2009.

(51) Int. Cl.
*C07D 401/04*    (2006.01)
*A61K 31/454*    (2006.01)

(52) U.S. Cl.
USPC .......................... 546/200; 514/323

(58) Field of Classification Search
USPC .......................... 546/200; 514/323
See application file for complete search history.

(56) References Cited

U.S. PATENT DOCUMENTS

| | | | |
|---|---|---|---|
| 5,767,118 | A | 6/1998 | Nargund et al. |
| 6,511,980 | B2 | 1/2003 | Johnson et al. |
| 6,967,199 | B2 | 11/2005 | Johnson et al. |
| 7,112,586 | B2 | 9/2006 | Johnson et al. |
| 7,166,601 | B2 | 1/2007 | Johnson et al. |
| 2002/0013352 | A1 | 1/2002 | Johnson et al. |
| 2003/0203906 | A1 | 10/2003 | Johnson et al. |
| 2004/0152732 | A1 | 8/2004 | Jasserand et al. |
| 2005/0148584 | A1 | 7/2005 | Johnson et al. |
| 2006/0183741 | A1 | 8/2006 | Johnson et al. |
| 2007/0037857 | A1 | 2/2007 | Perrissoud et al. |
| 2007/0054888 | A1 | 3/2007 | Johnson et al. |

FOREIGN PATENT DOCUMENTS

| | | |
|---|---|---|
| JP | 10-506914 | 7/1998 |
| JP | 2003-532710 | 11/2003 |
| JP | 2004-529184 | 9/2004 |
| JP | 2009-504697 | 2/2009 |
| WO | 2008/000729 | 1/2008 |

OTHER PUBLICATIONS

Talley Failure of a motilin receptor agonist (ABT-229) to relieve the symptoms of functional dyspepsia in patients with and without delayed gastric emptying: a randomizeddouble-blind placebo-controlled trial. Aliment Pharmacol Ther 2000;14:1653-61.*
Talley "Effects of amotilin receptor agonist (ABT-229) on upper gastrointestinal symptoms in type 1diabetes mellitus: a randomised, double blind, placebo controlled trial." Gut 2001;49: 395-401.*
International Search Report and Written Opinion issued Mar. 23, 2010 in International (PCT) Application No. PCT/JP2010/001368.
English translation of International Preliminary Report on Patentability and Written Opinion dated Aug. 30, 2011.

* cited by examiner

*Primary Examiner* — David K O Dell
(74) *Attorney, Agent, or Firm* — Wenderoth, Lind & Ponack, L.L.P.

(57) ABSTRACT

The present invention relates to novel oxyindole derivatives of formula (I) or a pharmaceutically acceptable salt thereof, processes for their preparation, pharmaceutical compositions containing them and their use in the treatment of various disorders which are mediated via the motilin receptor (GPR38).

{Chem. 47}

(I)

5 Claims, No Drawings

OXYINDOLE DERIVATIVES WITH MOTILIN RECEPTOR AGONISTIC ACTIVITY

This application is a U.S. national stage of International Application No. PCT/JP2010/001368 filed Mar. 1, 2010, which claim the benefit of U.S. provisional application Ser. No. 61/202,430 filed Feb. 27, 2009 and Ser. No. 61/282,173 filed Dec. 24, 2009.

TECHNICAL FIELD

The present invention relates to novel oxyindole derivatives of formula (I) or a pharmaceutically acceptable salt thereof, processes for their preparation, pharmaceutical compositions containing them and their use in the treatment of various disorders which are mediated via the motilin receptor (GPR38).

BACKGROUND ART

GPR38 is a 7-transmembrane, G-protein coupled receptor, with high affinity for the peptide motilin [Feighner et al., Science 1999, 284, 2184], suggesting that endogenous motilin exerts all or most of its activity via this receptor.

Motilin is a 22 amino acid peptide found in large amounts within endocrine-like cells of the gastrointestinal (GI) tract, and especially in the duodenum-jejunum areas. During fasting, the peptide is known to be associated with the onset of Phase III migrating complex activity within the stomach [Boivin et al., Dig. Dis. Sci. 1992, 37, 1562], suggesting a role in the mechanisms of prokinetic activity. Motilin is also released from the gut during feeding, sham feeding, gastric distension or by oral or intravenous nutrient application [Christofides et al., Gut 1979, 20, 102; Bormans et al., Scand. J. Gastroenterol. 1987, 22, 781], suggesting additional roles for this peptide in the modulation of motility patterns during feeding.

In animals or in man, motilin has long been known to increase GI motility, and promote gastric emptying and intestinal propulsion in an anal direction, during both fasting and fed conditions. This activity is thought to be primarily due to a facilitation of at least the cholinergic excitatory function of the gut [Van Assche et al., Eur. J. Pharmacol. 1997, 337, 267], perhaps also involving the activation of the vagus nerve [Mathis & Malbert, Am. J. Physiol. 1998, 274, G80]. In addition, higher concentrations of motilin directly evoke a small contraction of the muscle [Van Assche et al., Eur. J. Pharmacol. 1997, 337, 267].

The antibiotic erythromycin was shown to mimic the GI activity of motilin, in addition to its previously-described antibiotic properties [see Peeters, in Problems of the Gastrointestinal Tract in Anaesthesia Ed., Herbert M K et al. Springer-Verlag, Berlin, Heidelberg 1999, pp 39-51]. More recently, erythromycin has been shown to activate the GPR38 receptor, confirming its ability to mimic the function of motilin [Carreras et al., Analyt. Biochem. 2002, 300, 146]. In addition, the availability of this non-peptide motilin receptor agonist has allowed at least some clinical studies to be undertaken in order to examine the clinical potential of motilin receptor agonists. These studies have consistently demonstrated an ability to increase gastric emptying in various conditions associated with gastroparesis, such as functional dyspepsia and diabetic gastroparesis. Further, erythromycin has been shown to increase lower esophageal sphincter pressure in man, which together with the increase in gastric emptying, suggests a role in the treatment of gastroesophageal reflux disorders (GERD). Finally, erythromycin has been used to promote intestinal propulsive activity, finding clinical utility in the treatment of pseudoobstruction and in conditions with impaired colonic motility [Peeters, in Problems of the Gastrointestinal Tract in Anaesthesia Ed., Herbert M K et al. Springer-Verlag, Berlin, Heidelberg 1999, pp 39-51].

Consequently it is expected that agonists at the GPR38 receptor will mimic the activity of motilin or of other substances acting at this receptor, such as erythromycin, and find clinical utility in the treatment of GI disorders associated with hypomotility, especially the functional bowel disorders such as GERD, functional dyspepsia (FD) and irritable bowel syndrome (IBS). The compounds will also be useful for the treatment of other GI conditions where the cause is known and in which GI motility is reduced. Such conditions include constipation, caused by various diseases such as those associated with neuropathy, and/or by the administration of other drugs, intestinal pseudo-obstruction, paralytic ileus following surgery or some other manipulation, gastric stasis or hypomotility caused by various diseases such as diabetes and/or by the administration of other drugs, or in enterally fed patients. Interestingly, the ability of motilin or erythromycin to activate the vagus nerve, the association of this nerve with changes in feeding behaviour [e.g. Furness et al., Auton. Neurosci. 2001, 92, 28] and the chromosomal location of GPR38 [based on Ensembl: 13q21.1 (58.46-59.46 Mb)] within the markers (D13S257-13q14.11 to D13S258 at 13q21.33) of a locus associated with obesity [Feitosa et al, Am. J. Hum. Genet. 2002, 70, 72] also suggests that agonists active at the GPR38 receptor will, in addition to promoting GI motility, facilitate eating behaviours in at least those patients in which some degree of appetite suppression or cachexia is present. Such activity indicates that agonists at this receptor will find clinical utility in the treatment of symptoms associated with—for example—the treatment of cancer or by the presence of the cancer itself.

In addition to the ability of motilin receptor agonists to promote GI motility, the association of motilin gene polymorphism with Crohn's disease [Annese et al., Dig. Dis. ScL 1998, 43, 715-710] and the changes in motilin receptor density during colitis [Depoortere et al., Neurogastroenterol. Motil. 2001, 13, 55] suggests a utility for agonists at the motilin receptor for the treatment of inflammatory bowel conditions in general.

Finally, GPR38 is also found in regions outside the GI tract. These areas include the pituitary, adipose tissue, urinary bladder and certain areas of the brain. The former suggests clinical utility in the promotion of pituitary function, such as the release of growth hormone secretagogues, the presence within adipose tissue again suggests a role in the control of body weight, and the presence within the urinary bladder suggests a role for agonists at this receptor in the treatment of incontinence. The presence of GPR38 within the brain supports the GI and feeding utilities already mentioned, but in addition, suggests an involvement of the receptor in a greater spectrum of vagal-hypothalamic functions.

WO9410185, EP838469, WO9823629, DE19805822, and U.S. Pat. No. 6,165,985 claim erythromycin derivatives targeting GPR38 for use in disorders relating to GI motility. WO9921846, WO0185694, WO0168620, WO0168621, and WO0168622 disclose a series of small molecule antagonists of the GPR38 receptor. JP07138284 and EP807639 disclose peptide agonists. JP09249620, WO02092592, W005027637, US2005065156 and Li et al., (2004, Journal of Medicinal Chemistry, 47(7) p 1704-1708) disclose series of small molecule agonists. WO 05012331 and WO 05012332 disclose macrocyclic compounds which are agonists or antagonists of mammalian motilin or ghrelin receptors. WO 06127252 discloses erythromycin derivatives.

SUMMARY OF INVENTION

Technical Problem

There is a need to provide new motilin agonists that can be a good drug. They should be well absorbed from the GI tract, be metabolically stable and possess favorable pharmacokinetic properties. They should be non-toxic. Furthermore, the ideal drug candidate will exist in a physical form that is stable, non-hygroscopic and easily formulated. In particular, it has been desired that compounds must bind potently to the motilin receptor and show functional activity as agonists. The present invention provides novel compounds which have excellent motilin agonistic activities.

Solution to Problem

WO08/000729, WO07/007018, and WO07/012479 disclose a series of small molecule agonist.

The compounds of the present invention differ structurally from the cited arts known compounds by the presence of oxyindole.

Then, WO96/13265 is formally discloses oxyindole compounds. However, the compounds are growth hormone secretagogue which is different from motilin agonist. In addition all disclosed compounds of the present invention are thought to be introducing D-amino acid into the molecules, whereas the compounds of the present invention are characterized by introducing L-(alpha-, beta-, or gamma-) amino acid into the molecules.

WO96/13265 discloses the compounds with neither the L-amino acid moiety nor motilin agonistic activity.

A structurally novel class of compounds with L-type amino acid moiety in the molecules has now been found which provides agonists of the motilin receptor (GPR38).

The present invention therefore provides compounds of formula (I) and salts thereof:

{Chem. 1}

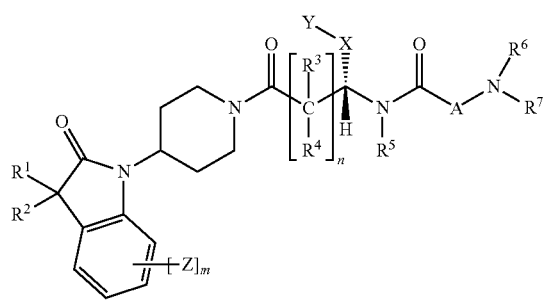

(I)

wherein $R^1$ and $R^2$ are independently selected from the group consisting of hydrogen, $C_1$-$C_4$ alkyl, and $C_3$-$C_7$ cycloalkyl; or alternatively $R^1$ and $R^2$, together with the atoms to which they are attached, form a 3 to 6 membered ring which may contain oxygen; said ring is optionally substituted with 1 to 4 substituents independently selected from the group consisting of halogen, hydroxy, $C_1$-$C_4$ alkyl, and $C_1$-$C_4$ alkoxy;

$R^3$ and $R^4$ are independently hydrogen or $C_1$-$C_4$ alkyl;

$R^5$ is hydrogen, $C_1$-$C_4$ alkyl, or $C_1$-$C_4$ alkoxy $C_1$-$C_4$ alkyl; of these, hydrogen or $C_1$-$C_4$ alkyl is preferred for $R^5$;

$R^6$ and $R^7$ are independently selected from hydrogen, $C_1$-$C_4$ alkyl, hydroxy $C_1$-$C_4$ alkyl, $C_1$-$C_4$ alkoxy $C_1$-$C_4$ alkyl, amino $C_1$-$C_4$ alkyl, $C_1$-$C_4$ alkyl amino $C_1$-$C_4$ alkyl, di($C_1$-$C_4$ alkyl)amino $C_1$-$C_4$ alkyl, saturated heterocyclyl, and saturated heterocyclyl $C_1$-$C_4$ alkyl; said saturated heterocyclyl and alkyl may have independently 1 to 4 $C_1$-$C_4$ alkyl; or alternatively $R^6$ and $R^7$ together with nitrogen atom to which they are attached form a 4 to 6 membered ring which may contain nitrogen or oxygen, wherein the 4 to 6 membered ring is optionally substituted with 1 to 4 substituents independently selected from the group consisting of hydroxy, $C_1$-$C_4$ alkyl, $C_1$-$C_4$ alkoxy, $C_3$-$C_7$ cycloalkyl, amino, $C_1$-$C_4$ alkylamino, and di($C_1$-$C_4$ alkylamino;

A is

{Chem. 2}

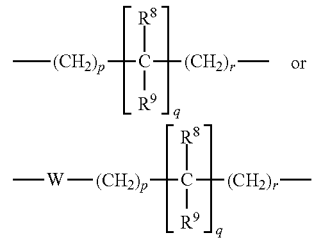

where p, q, and r are independently 0, 1, 2 or 3;

$R^8$ and $R^9$ are independently hydrogen, $C_1$-$C_6$ alkyl or $C_3$-$C_7$ cycloalkyl; said alkyl and cycloalkyl are optionally substituted with hydroxy, $C_1$-$C_4$ alkyl, amino, $C_1$-$C_4$ alkylamino, and di($C_1$-$C_4$ alkyl)amino; or $R^8$ and $R^9$ may be joined to one another to form a $C_3$-$C_7$ membered ring which may contain oxygen; or $R^8$ and $R^9$ may independently be joined to one or both of $R^8$ and $R^9$ groups to form alkylene bridges between the terminal nitrogen and the alkyl portion of the $R^8$ or $R^9$ groups, wherein the bridge contains 1 to 5 carbons atoms and may contain nitrogen or oxygen; said the bridge is optionally substituted with 1 to 4 substituents independently selected from the group consisting of halogen, hydroxy, $C_1$-$C_4$ alkyl, halo $C_1$-$C_4$ alkyl, and $C_1$-$C_4$ alkoxy;

W is N—$R^{10}$, said $R^{10}$ is hydrogen or $C_1$-$C_4$ alkyl;

X is $C_0$-$C_4$ alkylene, or $C_0$-$C_4$ alkylene-K—$C_0$-$C_4$ alkylene, where K is —O—, —NH—, $NR^9$—, —S—, —SO—, —$SO_2$—, —CO—, —OCO—, —C(O)O—, —$CR^{11}$=$CR^{12}$—, —C≡C—,    {Chem. 3}

—$NR^{11}$CO—, or —$CONR^{11}$—; said alkylene is optionally substituted with $C_1$-$C_4$ alkyl, hydroxy $C_1$-$C_4$ alkyl, amino $C_1$-$C_4$ alkyl, $C_1$-$C_4$ alkyl amino $C_1$-$C_4$ alkyl, di($C_1$-$C_4$)alkylamino $C_1$-$C_4$ alkyl, or $C_1$-$C_4$ alkoxy $C_1$-$C_4$ alkyl; of these, —O—, —NH— or $NR^9$— is preferred for K; of these, said alkylene being optionally substituted with $C_1$-$C_4$ alkyl, hydroxy $C_1$-$C_4$ alkyl, or $C_1$-$C_4$ alkoxy $C_1$-$C_4$ alkyl is preferred;

$R^{11}$ is hydrogen or $C_1$-$C_4$ alkyl;

Y is hydrogen, halogen, or 5-10 membered ring; said ring is optionally substituted with hydroxy, halogen, halo $C_1$-$C_4$ alkyl, $C_1$-$C_4$ alkyl, hydroxy $C_1$-$C_4$ alkyl, amino $C_1$-$C_4$ alkyl, $C_1$-$C_4$ alkoxy, or $C_1$-$C_4$ alkoxy $C_1$-$C_4$ alkyl; of these, hydrogen or 5-10 membered ring is preferred for Y; of these, said ring being optionally substituted with hydroxy, halogen, halo $C_1$-$C_4$ alkyl, $C_1$-$C_4$ alkyl, hydroxy $C_1$-$C_4$ alkyl, $C_1$-$C_4$ alkoxy, or $C_1$-$C_4$ alkyl is preferred;

Z is halogen, $C_1$-$C_4$ alkyl, $C_1$-$C_4$ alkoxy, or hydroxy;

m is 0, 1, 2, 3, or 4; of these, 0, 1 or 2 is preferred for m;

n is 0, 1, or 2; of these, 0 or 1 is preferred for n.

Also, the present invention provides the use of a compound of formula (I) or a pharmaceutically acceptable salt thereof, each as described herein, for the manufacture of a medicament for the treatment of a condition mediated by motilin receptor activity; in particular, motilin agonistic activity.

Preferably, the present invention also provides the use of a compound of formula (I) or a pharmaceutically acceptable salt thereof, each as described herein, for the manufacture of a medicament for the treatment of diseases selected from motilin related diseases.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, together with a pharmaceutically acceptable carrier for said compound and another pharmacologically active agent.

Further, the present invention provides a method of treatment of a condition mediated by motilin receptor activity, in a mammalian subject, which comprises administering to a mammal in need of such treatment a therapeutically effective amount of a compound of formula (I) or a pharmaceutically acceptable salt thereof, each as described herein.

Examples of conditions mediated by motilin receptor activity include, but are not limited to, motilin related diseases. The compounds of the present invention show the motilin receptor agonistic activity. The compounds of the present invention may show less toxicity, good absorption, distribution, good solubility, less protein binding affinity other than motilin receptor, less drug-drug interaction, and good metabolic stability.

Advantageous Effects of Invention

Actually it is confirmed in the present invention that when the L-type amino acid moiety is replaced with D-amino acid, the motilin agonistic activity is dramatically decreased. As shown in the table in the experiment part, the functional activity toward motilin receptor has been influenced by the absolute configuration of the amino acid linker moiety no less than 100-10000 fold between a compound with L-amino acid moiety and the corresponding compounds with D-amino acid moiety.

DESCRIPTION OF EMBODIMENTS

As used herein, the term "alkyl" as a group or part of a group e.g. alkoxy or hydroxyalkyl refers to a straight or branched alkyl group in all isomeric forms. The term "$C_1$-$C_4$ alkyl" refers to an alkyl group, as defined above, containing at least 1, and at most 4 carbon atoms. Examples of such alkyl groups include methyl, ethyl, propyl, iso-propyl, n-butyl, iso-butyl, sec-butyl, or tert-butyl. Examples of such alkoxy groups include methoxy, ethoxy, propoxy, iso-propoxy, butoxy, iso-butoxy, sec-butoxy and tert-butoxy.

The term "cycloalkyl", as used herein, preferably a cycloalkyl group having 3 to 7 carbon atoms and is exemplified by cyclopropyl, cyclobutyl, cyclopentyl and cyclohexyl, cycloheptyl. The term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "heterocyclyl" represents a 5 or 6 membered ring which comprises one or more heteroatoms selected from nitrogen, oxygen and sulphur. Examples of such heterocyclyl groups include pyrrolidinyl, piperidinyl, piperazinyl and morpholinyl.

In the compounds of formula (I), there is chiral carbon atom attached to X, and therefore compounds of formula (I) in a plane structure exists as stereoisomers. This invention is characterized to have one optical isomer of the stereoisomeric forms around the carbon atom attached to X in the compounds of formula (I), which is illustrated with a dotted line of the C—X bond. The intended stereoisomeric forms may be separated or resolved one from the other by conventional methods or any given isomer may be obtained by conventional stereoselective or asymmetric syntheses.

In certain of the compounds of formula (I), there may be some chiral carbon atoms other than the carbon atom attached to X. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

Suitable compounds of the invention are:

(R)—N—((S)-1-(4-(3,3-dimethyl-2-oxoindolin-1-yl)piperidin-1-yl)-1-oxo-4-phenylbutan-2-yl)piperidine-3-carboxamide;

(S)—N—((S)-1-(4-(3,3-dimethyl-2-oxoindolin-1-yl)piperidin-1-yl)-1-oxo-4-phenylbutan-2-yl)piperidine-2-carboxamide;

(S)-2-amino-N—((S)-1-(4-(3,3-dimethyl-2-oxoindolin-1-yl)piperidin-1-yl)-1-oxo-4-phenylbutan-2-yl)-3,3-dimethylbutanamide;

(S)-2-(1-aminocyclobutyl)-N-(1-(4-(3,3-dimethyl-2-oxoindolin-1-yl)piperidin-1-yl)-1-oxo-4-phenylbutan-2-yl)acetamide;

(S)-1-(aminomethyl)-N-(1-(4-(3,3-dimethyl-2-oxoindolin-1-yl)piperidin-1-yl)-1-oxo-4-phenylbutan-2-yl)cyclopropanecarboxamide;

(S)—N-(1-(4-(3,3-dimethyl-2-oxoindolin-1-yl)piperidin-1-yl)-1-oxo-4-phenylbutan-2-yl)azetidine-3-carboxamide;

(S)—N-(1-(4-(3,3-dimethyl-2-oxoindolin-1-yl)piperidin-1-yl)-1-oxo-4-phenylbutan-2-yl)piperidine-4-carboxamide;

(S)-2-(1-aminocyclopentyl)-N-(1-(4-(3,3-dimethyl-2-oxoindolin-1-yl)piperidin-1-yl)-1-oxo-4-phenylbutan-2-yl)acetamide;

(S)—N-(1-(4-(3,3-dimethyl-2-oxoindolin-1-yl)piperidin-1-yl)-1-oxo-4-phenylbutan-2-yl)-3-methyl-3-(methylamino)butanamide;

(S)-3-(cyclopentylamino)-N-(1-(4-(3,3-dimethyl-2-oxoindolin-1-yl)piperidin-1-yl)-1-oxo-4-phenylbutan-2-yl)propanamide;

(S)—N-(1-(4-(3,3-dimethyl-2-oxoindolin-1-yl)piperidin-1-yl)-1-oxo-4-phenylbutan-2-yl)-3-((2-methoxyethyl)(methyl)amino)propanamide;

(S)—N-(1-(4-(3,3-dimethyl-2-oxoindolin-1-yl)piperidin-1-yl)-1-oxo-4-phenylbutan-2-yl)-2-(pyrrolidin-1-yl)acetamide;

(R)—N—((S)-1-(4-(3,3-dimethyl-2-oxoindolin-1-yl)piperidin-1-yl)-1-oxo-4-phenylbutan-2-yl)-1-methylpiperidine-3-carboxamide;
(1S,3R)—N—((S)-3-(4-chlorophenyl)-1-(4-(3,3-dimethyl-2-oxoindolin-1-yl)piperidin-1-yl)-1-oxopropan-2-yl)-3-(methylamino)cyclopentanecarboxamide;
(1S,3R)—N—((S)-1-(4-(3,3-dimethyl-2-oxoindolin-1-yl)piperidin-1-yl)-1-oxo-3-(2-(trifluoromethyl)phenyl)propan-2-yl)-3-(methylamino)cyclopentanecarboxamide;
(1S,3R)—N—((S)-3-cyclohexyl-1-(4-(3,3-dimethyl-2-oxoindolin-1-yl)piperidin-1-yl)-1-oxopropan-2-yl)-3-(methylamino)cyclopentanecarboxamide;
(1S,3R)—N—((S)-1-(4-(3,3-dimethyl-2-oxoindolin-1-yl)piperidin-1-yl)-3-(naphthalen-1-yl)-1-oxopropan-2-yl)-3-(methylamino)cyclopentanecarboxamide;
(1S,3R)—N—((S)-3-(2-chlorophenyl)-1-(4-(3,3-dimethyl-2-oxoindolin-1-yl)piperidin-1-yl)-1-oxopropan-2-yl)-3-(methylamino)cyclopentanecarboxamide;
(1S,3R)—N—((S)-1-(4-(3,3-dimethyl-2-oxoindolin-1-yl)piperidin-1-yl)-1-oxo-3-o-tolylpropan-2-yl)-3-(methylamino)cyclopentanecarboxamide;
(1S,3R)—N—((S)-1-(4-(3,3-dimethyl-2-oxoindolin-1-yl)piperidin-1-yl)-3-(4-fluorophenyl)-1-oxopropan-2-yl)-3-(methylamino)cyclopentanecarboxamide;
(1S,3R)—N—((S)-1-(4-(3,3-dimethyl-2-oxoindolin-1-yl)piperidin-1-yl)-3-(3-fluorophenyl)-1-oxopropan-2-yl)-3-(methylamino)cyclopentanecarboxamide;
(1S,3R)—N—((S)-3-(3-chlorophenyl)-1-(4-(3,3-dimethyl-2-oxoindolin-1-yl)piperidin-1-yl)-1-oxopropan-2-yl)-3-(methylamino)cyclopentanecarboxamide;
(1S,3R)—N—((S)-1-(4-(3,3-dimethyl-2-oxoindolin-1-yl)piperidin-1-yl)-1-oxo-3-phenylpropan-2-yl)-3-(methylamino)cyclopentanecarboxamide;
(1S,3R)—N—((S)-1-(4-(3,3-dimethyl-2-oxoindolin-1-yl)piperidin-1-yl)-3-(3-methoxyphenyl)-1-oxopropan-2-yl)-3-(methylamino)cyclopentanecarboxamide;
(1S,3R)—N—((S)-1-(4-(3,3-dimethyl-2-oxoindolin-1-yl)piperidin-1-yl)-3-(2-fluorophenyl)-1-oxopropan-2-yl)-3-(methylamino)cyclopentanecarboxamide;
(1S,3R)—N—((S)-1-(4-(3,3-dimethyl-2-oxoindolin-1-yl)piperidin-1-yl)-4-methyl-1-oxopentan-2-yl)-3-(methylamino)cyclopentanecarboxamide;
(1S,3R)—N—((S)-1-(4-(3,3-dimethyl-2-oxoindolin-1-yl)piperidin-1-yl)-3-(1H-indol-3-yl)-1-oxopropan-2-yl)-3-(methylamino)cyclopentanecarboxamide;
(1S,3R)—N—((S)-1-(4-(3,3-dimethyl-2-oxoindolin-1-yl)piperidin-1-yl)-1-oxo-3-(3-(trifluoromethyl)phenyl)propan-2-yl)-3-(methylamino)cyclopentanecarboxamide;
(1S,3R)—N—((S)-1-(4-(3,3-dimethyl-2-oxoindolin-1-yl)piperidin-1-yl)-1-oxo-3-(4-(trifluoromethyl)phenyl)propan-2-yl)-3-(methylamino)cyclopentanecarboxamide;
(1S,3R)—N—((S)-1-(4-(3,3-dimethyl-2-oxoindolin-1-yl)piperidin-1-yl)-3-(4-methoxyphenyl)-1-oxopropan-2-yl)-3-(methylamino)cyclopentanecarboxamide;
(1S,3R)—N—((S)-1-(4-(3,3-dimethyl-2-oxoindolin-1-yl)piperidin-1-yl)-1-oxo-3-phenoxypropan-2-yl)-3-(methylamino)cyclopentanecarboxamide;
(1S,3R)—N—((S)-3-(2-chlorophenoxy)-1-(4-(3,3-dimethyl-2-oxoindolin-1-yl)piperidin-1-oxopropan-2-yl)-3-(methylamino)cyclopentanecarboxamide;
(1S,3R)—N—((S)-4-(4-(3,3-dimethyl-2-oxoindolin-1-yl)piperidin-1-yl)-4-oxo-1-phenylbutan-2-yl)-3-(methylamino)cyclopentanecarboxamide;
(R)—N—((S)-1-(4-(5-fluoro-3,3-dimethyl-2-oxoindolin-1-yl)piperidin-1-yl)-1-oxo-4-phenylbutan-2-yl)piperidine-3-carboxamide;
(1S,3R)—N—((S)-1-(4-(5-fluoro-3,3-dimethyl-2-oxoindolin-1-yl)piperidin-1-yl)-1-oxo-4-phenylbutan-2-yl)-3-(methylamino)cyclopentanecarboxamide;
(S)—N-(1-(4-(5-fluoro-3,3-dimethyl-2-oxoindolin-1-yl)piperidin-1-yl)-1-oxo-4-phenylbutan-2-yl)-3-methyl-3-(methylamino)butanamide;
(S)—N—((S)-1-(4-(3,3-dimethyl-2-oxoindolin-1-yl)piperidin-1-yl)-1-oxo-4-phenylbutan-2-yl)-3-(methylamino)pyrrolidine-1-carboxamide;
1-((S)-1-(4-(3,3-dimethyl-2-oxoindolin-1-yl)piperidin-1-yl)-1-oxo-4-phenylbutan-2-yl)-3-((S)-pyrrolidin-2-ylmethyl)urea;
1-((S)-1-(4-(3,3-dimethyl-2-oxoindolin-1-yl)piperidin-1-yl)-1-oxo-4-phenylbutan-2-yl)-3-((R)-piperidin-3-yl)urea;
3-((S)-1-(4-(3,3-dimethyl-2-oxoindolin-1-yl)piperidin-1-yl)-1-oxo-4-phenylbutan-2-yl)-1-methyl-1-((S)-pyrrolidin-2-ylmethyl)urea;
1-((S)-1-(4-(3,3-dimethyl-2-oxoindolin-1-yl)piperidin-1-yl)-1-oxo-4-phenylbutan-2-yl)-3-((R)-pyrrolidin-2-ylmethyl)urea;
1-((S)-1-(4-(3,3-dimethyl-2-oxoindolin-1-yl)piperidin-1-yl)-1-oxo-4-phenylbutan-2-yl)-3-(R)-pyrrolidin-3-yl)urea;
1-((S)-1-(4-(3,3-dimethyl-2-oxoindolin-1-yl)piperidin-1-yl)-1-oxo-4-phenylbutan-2-yl)-3-((R)-pyrrolidin-3-ylmethyl)urea;
(R)—N—((S)-1-(4-(3,3-dimethyl-2-oxoindolin-1-yl)piperidin-1-yl)-1-oxo-4-phenylbutan-2-yl)-3-methylpiperazine-1-carboxamide;
(S)-1-(1-(4-(3,3-dimethyl-2-oxoindolin-1-yl)piperidin-1-yl)-1-oxo-4-phenylbutan-2-yl)-3-(4-ethylpiperidin-4-yl)urea;
(S)-1-(1-(4-(3,3-dimethyl-2-oxoindolin-1-yl)piperidin-1-yl)-1-oxo-4-phenylbutan-2-yl)-3-(4-methylpiperidin-4-yl)urea;
1-((S)-1-(4-(3,3-dimethyl-2-oxoindolin-1-yl)piperidin-1-yl)-1-oxo-4-phenylbutan-2-yl)-3-((S)-pyrrolidin-3-yl)urea;
1-((S)-1-(4-(3,3-dimethyl-2-oxoindolin-1-yl)piperidin-1-yl)-1-oxo-4-phenylbutan-2-yl)-3-((S)-piperidin-2-ylmethyl)urea;
1-((S)-1-(4-(3,3-dimethyl-2-oxoindolin-1-yl)piperidin-1-yl)-1-oxo-4-phenylbutan-2-yl)-3-((S)-piperidin-3-ylmethyl)urea;
(S)-1-(2-amino-2-methylpropyl)-3-(1-(4-(3,3-dimethyl-2-oxoindolin-1-yl)piperidin-1-yl)-1-oxo-4-phenylbutan-2-yl)urea;
(S)-3-(cyclopropyl(methyl)amino)-N—((S)-1-(4-(3,3-dimethyl-2-oxoindolin-1-yl)piperidin-1-yl)-1-oxo-4-phenylbutan-2-yl)pyrrolidine-1-carboxamide;
(S)-1-(1-(4-(3,3-dimethyl-2-oxoindolin-1-yl)piperidin-1-yl)-1-oxo-4-phenylbutan-2-yl)-3-(2-pyrrolidin-1-yl)ethyl)urea;
(S)-1-(1-(4-(3,3-dimethyl-2-oxoindolin-1-yl)piperidin-1-yl)-1-oxo-4-phenylbutan-2-yl)-3-(2-(dimethylamino)ethyl)urea;
(S)—N—((S)-1-(4-(3,3-dimethyl-2-oxoindolin-1-yl)piperidin-1-yl)-1-oxo-4-phenylbutan-2-yl)-3-(dimethylamino)pyrrolidine-1-carboxamide;
1-((S)-1-(4-(3,3-dimethyl-2-oxoindolin-1-yl)piperidin-1-yl)-1-oxo-4-phenylbutan-2-yl)-3-(((S)-1-methylpyrrolidin-2-yl)methyl)urea;
(S)-1-(1-(4-(3,3-dimethyl-2-oxoindolin-1-yl)piperidin-1-yl)-1-oxo-4-phenylbutan-2-yl)-3-(1,4-dimethylpiperidin-4-yl)urea;

(S)—N—((S)-1-(4-(5-fluoro-3,3-dimethyl-2-oxoindolin-1-yl)piperidin-1-yl)-1-oxo-4-phenylbutan-2-yl)-3-(methylamino)pyrrolidine-1-carboxamide;
1-((S)-1-(4-(5-fluoro-3,3-dimethyl-2-oxoindolin-1-yl)piperidin-1-yl)-1-oxo-4-phenylbutan-2-yl)-3-((S)-pyrrolidin-2-ylmethyl)urea;
(S)-1-(1-(4-(5-fluoro-3,3-dimethyl-2-oxoindolin-1-yl)piperidin-1-yl)-1-oxo-4-phenylbutan-2-yl)-3-(4-methylpiperidin-4-yl)urea;
(S)—N-(1-(4-(3,3-dimethyl-2-oxoindolin-1-yl)piperidin-1-yl)-1-oxo-3-(2-(trifluoromethyl)phenyl)propan-2-yl)piperidine-4-carboxamide;
(S)—N-(3-(2-chlorophenyl)-1-(4-(3,3-dimethyl-2-oxoindolin-1-yl)piperidin-1-yl)-1-oxopropan-2-yl)piperidine-4-carboxamide;
(S)—N-(3-(4-chlorophenyl)-1-(4-(3,3-dimethyl-2-oxoindolin-1-yl)piperidin-1-yl)-1-oxopropan-2-yl)piperidine-4-carboxamide;
(R)—N—((S)-1-(4-(3,3-dimethyl-2-oxoindolin-1-yl)piperidin-1-yl)-1-oxo-3-phenylpropan-2-yl)piperidine-3-carboxamide;
(R)—N—((S)-1-(4-(3,3-dimethyl-2-oxoindolin-1-yl)piperidin-1-yl)-3-(2-fluorophenyl)-1-oxopropan-2-yl)piperidine-3-carboxamide;
(R)—N—((S)-1-(4-(3,3-dimethyl-2-oxoindolin-1-yl)piperidin-1-yl)-3-(3-fluorophenyl)-1-oxopropan-2-yl)piperidine-3-carboxamide;
(R)—N—((S)-1-(4-(3,3-dimethyl-2-oxoindolin-1-yl)piperidin-1-yl)-1-oxo-3-(2-(trifluoromethyl)phenyl)propan-2-yl)piperidine-3-carboxamide;
(R)—N—((S)-3-(2-chlorophenyl)-1-(4-(3,3-dimethyl-2-oxoindolin-1-yl)piperidin-1-yl)-1-oxopropan-2-yl)piperidine-3-carboxamide;
(R)—N—((S)-3-(4-chlorophenyl)-1-(4-(3,3-dimethyl-2-oxoindolin-1-yl)piperidin-1-yl)-1-oxopropan-2-yl)piperidine-3-carboxamide;
(S)—N—((S)-1-(4-(3,3-dimethyl-2-oxoindolin-1-yl)piperidin-1-yl)-3-(3-fluorophenyl)-1-oxopropan-2-yl)-3-(methylamino)pyrrolidine-1-carboxamide;
(S)—N—((S)-1-(4-(3,3-dimethyl-2-oxoindolin-1-yl)piperidin-1-yl)-1-oxo-3-(2-(trifluoromethyl)phenyl)propan-2-yl)-3-(methylamino)pyrrolidine-1-carboxamide;
(S)—N—((S)-3-(2-chlorophenyl)-1-(4-(3,3-dimethyl-2-oxoindolin-1-yl)piperidin-1-yl)-1-yl)-1-oxopropan-2-yl)-3-(methylamino)pyrrolidine-1-carboxamide;
(S)—N—((S)-3-(4-chlorophenyl)-1-(4-(3,3-dimethyl-2-oxoindolin-1-yl)piperidin-1-yl)-1-oxopropan-2-yl)-3-(methylamino)pyrrolidine-1-carboxamide;
and salts thereof.

Included within the scope of the "compounds of the invention" are all salts, solvates, hydrates, complexes, polymorphs, prodrugs, radiolabeled derivatives, stereoisomers and optical isomers of the compounds of formula (I).

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. ScL, 1977, 66, 1-19, such as acid addition salts formed with inorganic acids e.g. hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

The compounds of formula (I) and salts thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Compounds of the invention that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances, Isotopically labeled compounds of the invention can generally be prepared by carrying out the procedures disclosed in the Schemes and/or in the Examples below, then substituting a readily available isotopically labeled reagent for a non-isotopically labeled reagent.

The potencies and efficacies of the compounds of this invention for GPR38 can be determined by reporter assay performed on the human cloned receptor as described herein.

Compounds of formula (I) have demonstrated agonistic activity at the GPR38 receptor, using the functional assay described herein.

Compounds of formula (I) and pharmaceutically acceptable salts thereof are therefore of use in the treatment of conditions or disorders which are mediated via the GPR38 receptor. In particular the compounds of formula (I) and pharmaceutically acceptable salts thereof are of use in the treatment of certain GI disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, or in enterally fed patients, Crohn's disease, colitis, cachexia associated with advanced diseases such as cancer and/or the treatment thereof, and other disorders such as incontinence (herein after referred to as the "Disorders of the Invention").

It is to be understood that "treatment" as used herein includes prophylaxis as well as alleviation of established symptoms.

Thus the invention also provides compounds of formula (I) and pharmaceutically acceptable salts thereof for use as a therapeutic substance, in particular in the treatment of conditions or disorders mediated via the GPR38 receptor. In particular the invention provides compounds of formula (I) and pharmaceutically acceptable salts thereof for use as a therapeutic substance in the treatment of "Disorders of the Invention".

The invention further provides a method of treatment of conditions or disorders in mammals including humans which can be mediated via the GPR38 receptor, which comprises administering to the sufferer a therapeutically safe and effective amount of a compound of formula (I) or a pharmaceutically acceptable salt thereof.

In another aspect, the invention provides for the use of compounds of formula (I) and pharmaceutically acceptable salts thereof in the manufacture of a medicament for use in the treatment of the conditions or disorders mediated via the GPR38 receptor.

In order to use the compounds of formula (I) and pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrate compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycolate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg or 1.0 to 200 mg, and such unit doses may be administered once a day or more than once a day, for example two or three times a day.

Compounds of formula (I) and pharmaceutically acceptable salts thereof may be used in combination preparations. For example, the compounds of formula (I) and pharmaceutically acceptable salts thereof may be used in combination with one or more compounds with activity in reducing gastric acid; one or more compounds with activity in reducing gastro-esophageal reflux; one or more compounds with activity in reducing esophago-gastric irritancy or inflammation, especially when used to alleviate erosive or non-erosive esophagitis; one or more compounds with analgesic activity; and/or one or more compounds with mixed activity on motility and pain.

Examples of compounds with activity in reducing gastric acid include H2 receptor antagonists, acid pump antagonists and proton pump inhibitors. Examples of compounds with activity in reducing gastro-esophageal reflux include agonists at GABA-B. Examples of compounds with analgesic activity include compounds active at Neurokinin receptors (NK1, 2, 3), TRPV1 and sodium-channels. Examples of compounds with mixed activity on motility and pain include CRF2 antagonists, 5-HT3 antagonists or octreotide or other molecules active at sst2 receptors.

All publications, including but not limited to patents and patent applications, cited in this specification are herein incorporated by reference as if each individual publication were specifically and individually indicated to be incorporated by reference herein as though fully set forth. The following Descriptions and Examples illustrate the preparation of compounds of the invention.

General Synthesis

Throughout the instant application, the following abbreviations are used with the following meanings:

BOC: t-butyloxycarbonyl
BOP: 1H-Benzotriazol-1-yloxytris(dimethylamino)phosphonium Hexafluorophosphate
CBZ: Benzyloxycarbonyl
DCC: dicyclohexylcarbodiimide
DMF: N,N-dimethylformamide
EDC: 1-Ethyl-3-(3-dimethylaminopropyl)carbodiimide Hydrochloride
FMOC: 9-fluorenylmethoxycarbonyl
HOBT: 1-Hydroxybenztriazole
HBTU: O-(Benzotriazol-1-yl)-N,N,N',N'-tetramethyluronium Hexafluorophosphate
HPLC: High pressure liquid chromatography
MHz: Megahertz
NMR: Nuclear Magnetic Resonance
TFA: Trifluoroacetic acid
THF: Tetrahydrofuran
TLC: Thin layer chromatography The compounds of the instant invention all have at least one asymmetric center as noted by the asterisk in the following structural Formula I:

{Chem. 4}

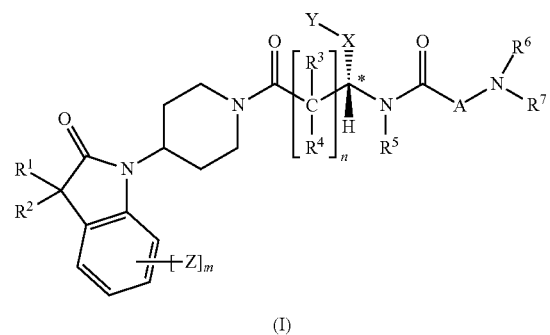

Formula I (I)

This invention is characterized to have one optical isomer of the stereoisomeric forms around the asterisked carbon. Additional asymmetric centers may be present on the molecule depending upon the nature of the various substituents on the molecule. Each such asymmetric center will produce equal to or more than two optical isomers and it is intended that all such optical isomers, as separated, pure optical isomers thereof, be included within the ambit of the instant invention.

Compounds which are more than about $10^3$ active as motilin receptor agonist and, therefore are preferred, are those in which the substituent of —X—Y is below and the hydrogen atom is above the plane of the structure as represented in Formula I.

This configuration corresponds to that present in a L-amino acid, which include alpha-amino acid, beta-amino acid or gamma-amino acid in the case of n=1, 2 or 3 of formula I, respectively. In most cases, this is also designated as an S-configuration although this will vary according to the value of —X—Y used in making the R- or S-stereochemical assignments. Their absolute stereochemistry may be determined by the X-ray crystallography of crystalline products or crystalline intermediates which are derivatized, if necessary, containing an asymmetric center of known configuration.

The preparation of compounds of Formula I of the present invention can be carried out in sequential or convergent synthetic routes.

Syntheses detailing the preparation of the compounds of Formula I in a sequential manner are presented in the following reaction schemes.

The term "standard peptide coupling reaction conditions" is used repeatedly here, and it means coupling a carboxylic acid with an amine using an acid activating agent such as EDC, DCC, HBTU, and BOP in a inert solvent such as DMF and dichloromethane in the presence of a catalyst such as HOBT and/or in the presence of a base such as diisopropylethyamine or triethylamine.

The term "PG1", as used hereinafter, means an amino-protecting group which is selected from typical amino-protecting groups described in Protective Groups in Organic Synthesis edited by T. W. Greene et al. (John Wiley & Sons, 1999). Typical amino-protecting groups include benzyl, CBZ, FMOC and BOC. Of these groups, benzyl, CBZ and BOC are preferred.

BOC and benzyl were used extensively in the syntheses of this invention, and their removal conditions are known to those skilled in the art. Removal of BOC protecting groups is carried out in a solvent such as methylene chloride or methanol, with a strong acid, such as trifluoroacetic acid (TFA) or hydrochloric acid (HCl). Removal of benzyl and CBZ groups can be achieved by a number of methods, for example, catalytic hydrogenation with hydrogen in the presence of palladium catalyst in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide.

The protected amino acid derivatives IV are, in many cases, commercially available, where the amino protecting group is PG1. The protected amino acid derivatives IV other than commercially available ones can be prepared by literature methods (Williams, R. M. Synthesis of Optically Active amino Acids, Pergamon Press: Oxford, 1989).

Many of the oxyindol piperidines of formula II can be prepared by following methods described in Scheme 13, 14, and 15. The skills required in carrying out the reaction and purification of the resulting reaction products are known to those skilled in the art. Purification procedures include crystallization, normal phase and/or reverse phase chromatography.

Scheme 1

{Chem. 5}

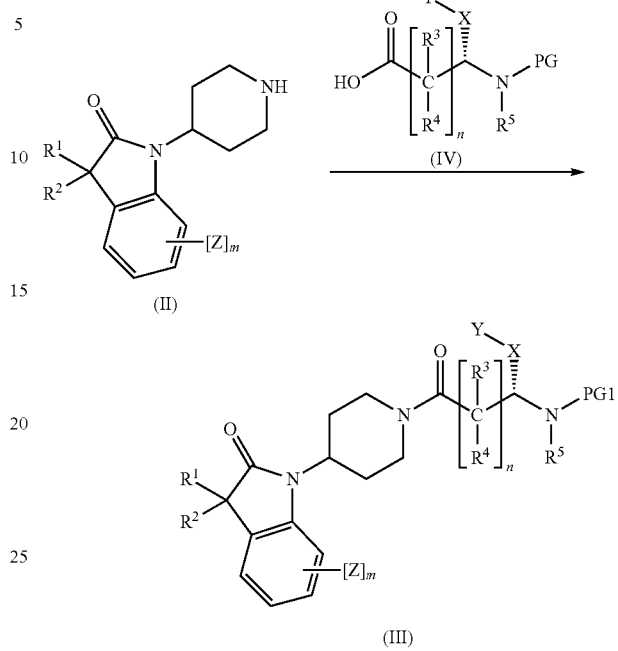

Intermediates of formula III can be synthesized as described in Scheme 1. Coupling of amine of formula II, whose preparations are described later if they are not commercially available, to protected amino acids of formula IV wherein PG1 is a suitable protecting group, is conveniently carried out under standard peptide coupling conditions.

Scheme 2

{Chem. 6}

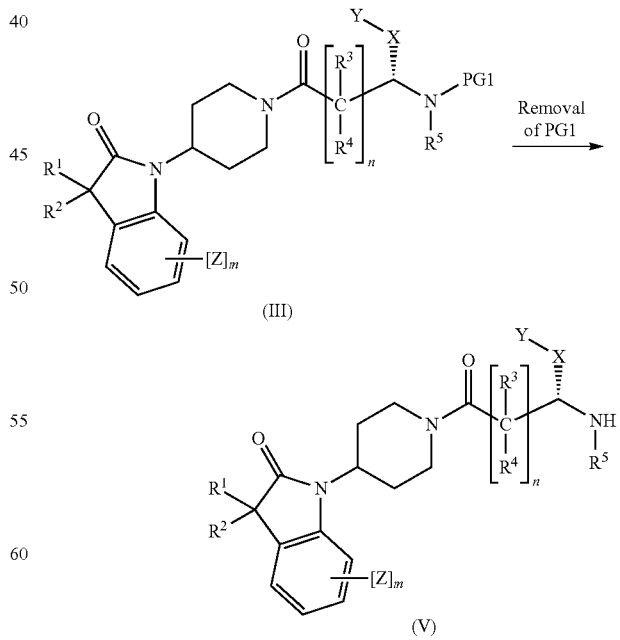

Conversion of III to intermediates V can be carried out as illustrated in Scheme 2 by removal of the amino protecting group, PG1 (CBZ, BOC, etc.).

Scheme 3

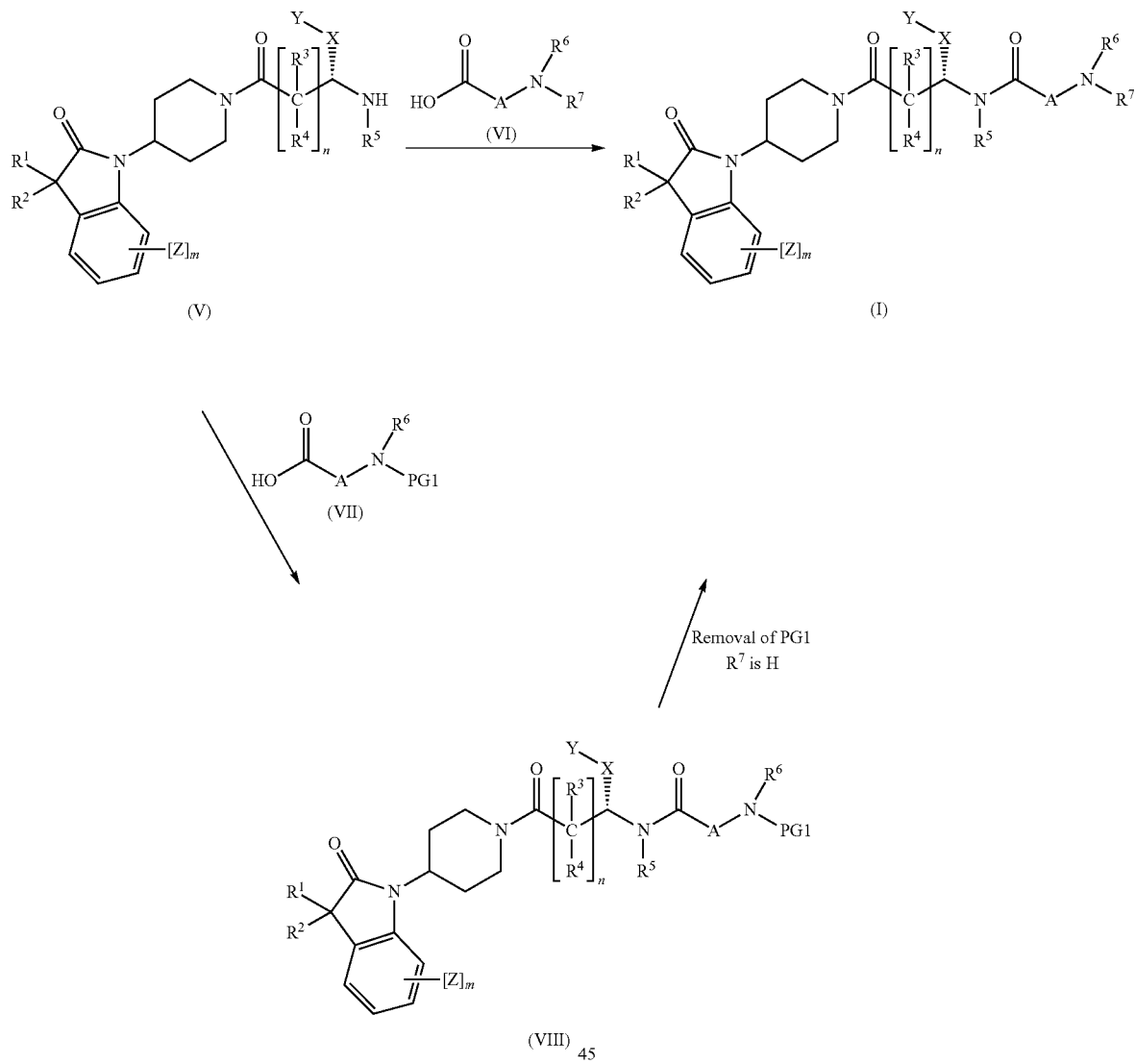

Intermediates of formula VI, wherein A is connected to the carbonyl by a carbon atom —(CH$_2$)pCR$^8$R$^9$q(CH$_2$)r— as shown in Scheme 3 can be coupled to intermediates of formula V under the standard peptide coupling reaction conditions. The amino acids VI, as amino acids VII, are commercially available or can be synthesized according to the procedure known in the art. One of the procedures is described in working example 21. Also if R$^6$ or R$^7$ is a hydrogen then the protected amino acids VII are employed in the coupling reaction, wherein PG1 is a amino-protecting group as defined above. Removal of PG1 in VIII to afford I, where R$^7$=hydrogen atom (H), can be carried out under conditions known in the art.

Scheme 4

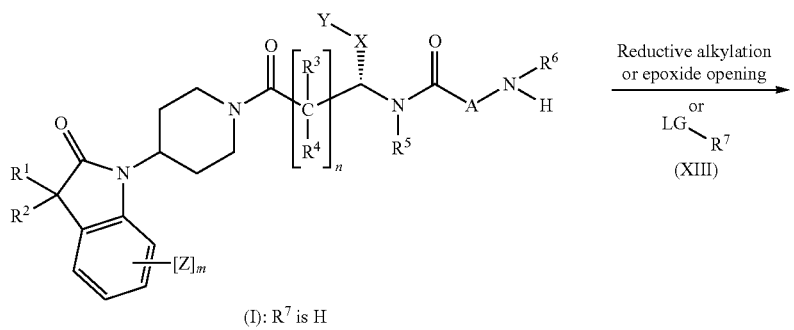

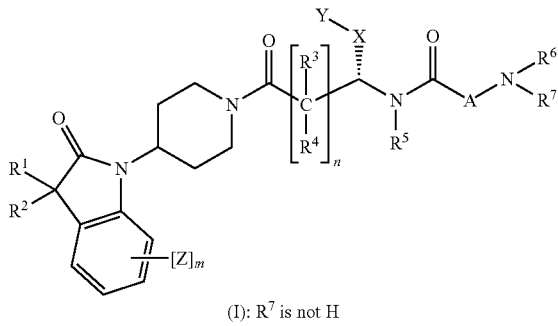

(I): R[7] is not H

Compounds of formula I wherein $R^6$ and/or $R^7$ is a H can be further elaborated to new compounds I, which are substituted on the amino group as depicted in Scheme 4. Reductive alkylation of I with an aldehyde is carried out under conditions known in the art; for example, by reduction of corresponding imine or iminium salt, either isolated or generated in situ, with hydrogen in the presence of platinum, palladium, or nickel catalysts or with chemical reducing agents such as sodium triacetoxyborohydride or sodium cyanoborohydride in a protic solvent such as methanol, ethanol, or 2-propanol in the present of catalytic amount of acid. Alternatively, a similar transformation can be accomplished via an epoxide opening reaction under presence of suitable base in inert solvent. Alternatively, a similar transformation can be accomplished by alkylation with the reagent of $R^7$-LG under presence of suitable base in inert solvent. Wherein the LG is "leaving group", as used herein, and signifies a group capable of being substituted by nucleophilic groups, such as amines, metal-amides and examples of such leaving groups include halogen atoms, alkylsulfonyl group, and arylsulfonyl group, nitrobenzenecarbonyl group, perhalobenzenecarbonyl group. Of these, an iodine atom, a metanesulfonyl group, a trifluoromethanesulfonyl group, and 4-methylphenylsulfonyl group are preferred.

The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMSO, THF, diethylether, diisopropylether, dimethoxyethane, acetonitrile, dichloromethane, dichloroethane and chloroform are preferred.

Scheme 5
{Chem. 9}

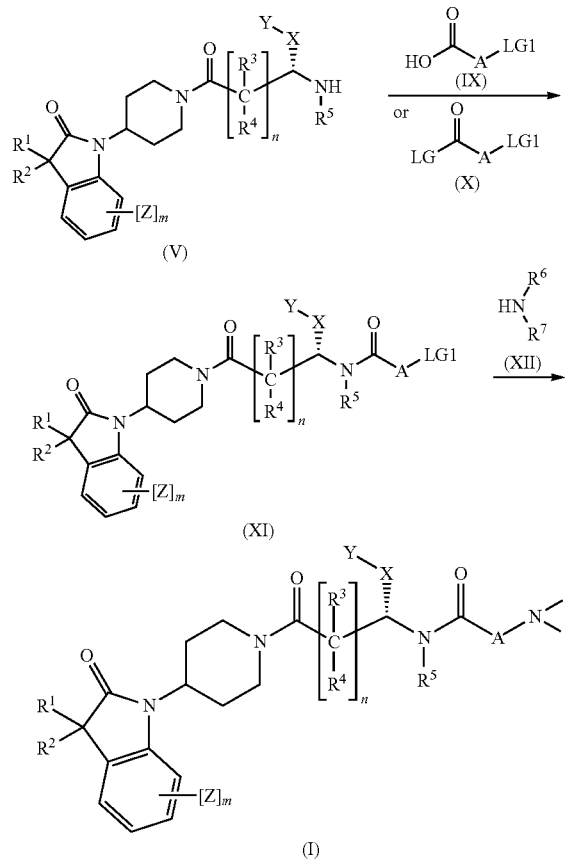

Scheme 6
{Chem. 10}

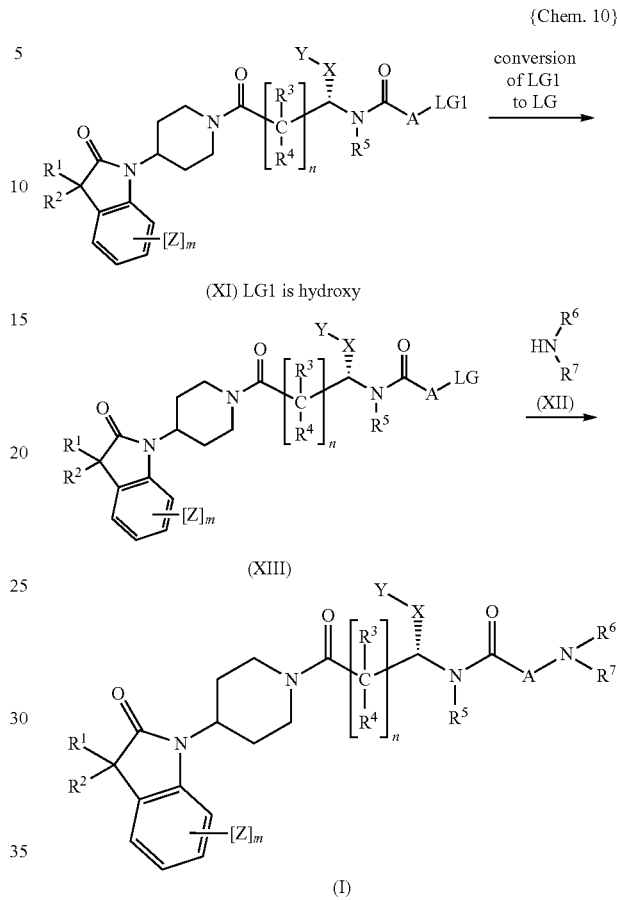

Compounds of the formula I can be prepared by nucleophilic addition of the intermediate of formula XI with amine IX as shown in Scheme 5. The intermediate of formula XI can be prepared by coupling reaction with amine of formula V and acid of formula IX is carried out under standard peptide coupling reaction condition, wherein LG1 is a halogen atom such as chloride, bromide, and iodide. Alternatively, the intermediate of formula XI can be prepared by coupling reaction with amine of formula V and activated acid equivalent of formula X is carried out under presence of suitable bases in inert solvent.

Compound formula of XI is converted to the target compound of formula I under presence of amine XII and suitable base in inert solvent.

When LG1 is a hydroxy group, the desired compound of formula I can be prepared via intermediate of formula XIII wherein LG as defined above as shown in Scheme 6. Conversion of hydroxy group of the compound formula XI to intermediate of formula XIII is carried out under conditions in the art; for example, by conversion of hydroxy group to LG with triphenylphosphine and tetrahalomethane or N-halo-succinimide in inert solvent. Alternatively, the electrophilic intermediate of formula XIII can be prepared by sulfonylation. Conversion to an alkyl- or arylsulfonyl ester of formula XIII can be carried out with the corresponding sulfonyl chloride under presence suitable base in inert solvent.

Alternatively, Compounds of formula I can be prepared as shown in Scheme 6 by reacting XIII with reagent XII, wherein A-LG is —$(CH_2)p$-$C\{(R^8)(R^9)\}q$-$(CH_2)r$-1-CHO.

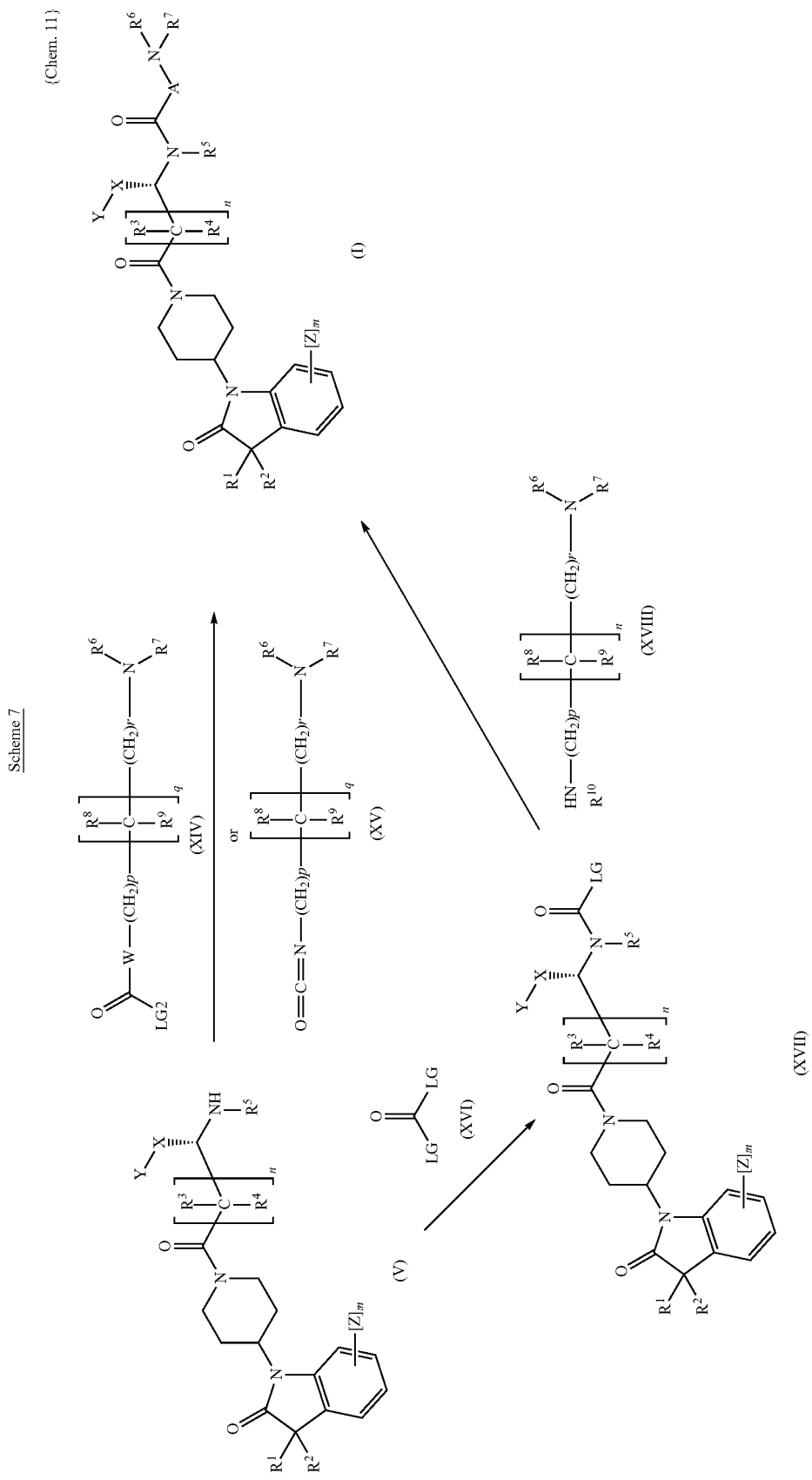

Compounds of formula I, wherein A is W—(CH$_2$)p-C{(R$^8$)(R$^9$)}q-(CH$_2$)r- and W is N—R$^{10}$ or NH can be prepared as shown in Scheme 7 by reacting V with reagent XIV, wherein LG2 is an appropriate leaving group such as Cl, Br, I, imidazole, or o-nitrobenzene. Alternatively, V can be reacted with an isocyanate of formula XV in an inert solvent such as 1,2-dichloroethane which results in a compound of formula I where W is NH. Compound of formula I can be prepared via intermediate of formula XVII. The intermediate of XVII can be prepared by coupling reaction of compound of formula V with the reagent of formula XVI, wherein LG as defined above, under presence of a suitable base in an inert solvent. The intermediate of formula XVII can be isolated or generated in situ. The conversion from the intermediate of formula XVII to the desired compound of formula I is carried out by nucleophilic substitution reaction of the formula XVIII under presence of a suitable base in an inert solvent.

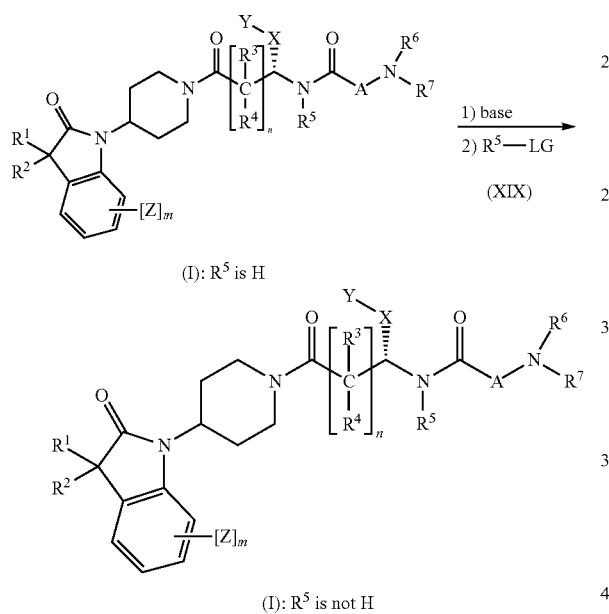

The compound of formula I, wherein R$^5$ is not hydrogen, can be further elaborated to new compounds I, which are substituted on the amide NH group as depicted in Scheme 8. Alkylation of compound of formula I is carried out by nucleophilic substitution reaction of reagent of formula XIX, wherein LG as defined above, with suitable base treated compound of formula I.

Scheme 9

{Chem. 13}

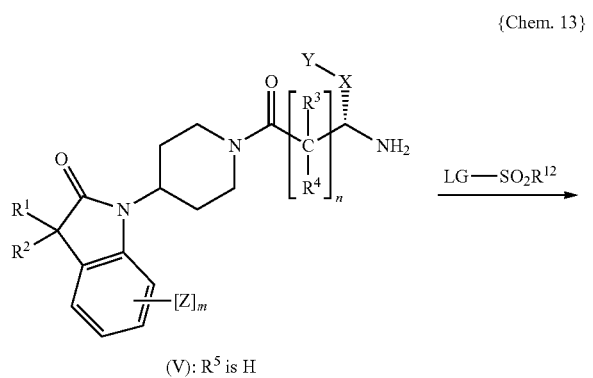

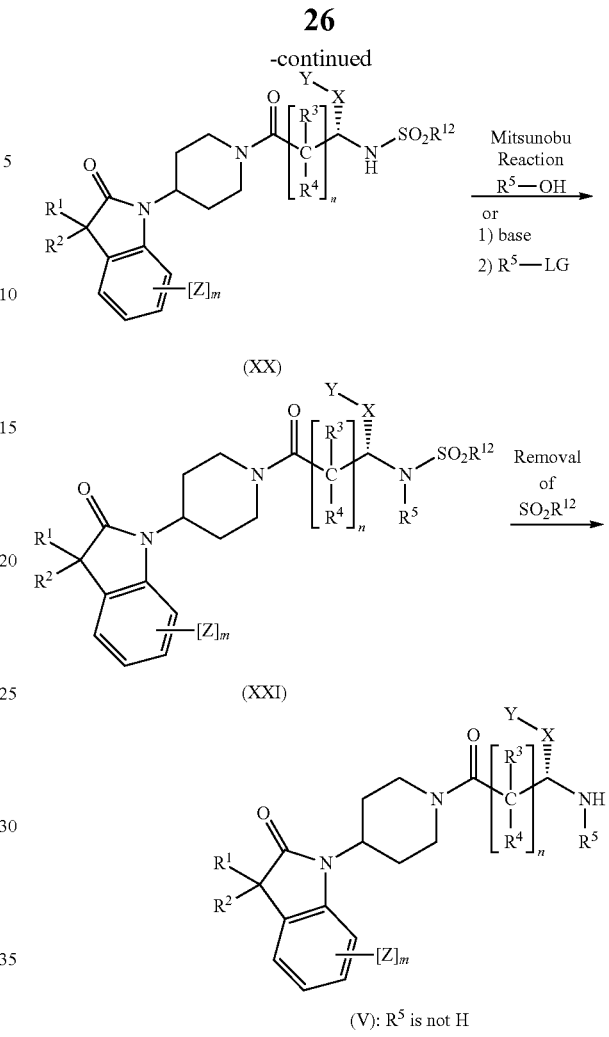

The compound of formula V, wherein R$^5$ is not hydrogen, can be prepared via sulfonamides of formula XX as shown in Scheme 9. The sulfonamide preparation of compound XX is carried out by the reaction of compound of formula V and alkylsulfonyl, or arylsulfonyl halide, wherein R$^{12}$ is selected from typical sulfonyl protecting groups described in Protective Groups in Organic Synthesis edited by T. W. Greene et al. (John Wiley & Sons, 1999). Examples of suitable protecting groups include, but are not limited to: methanesulfonyl, trifluoromethanesulfonyl, benzenesulfonyl, 2- or 4-nitrobenzenesulfonyl, and 2,4-dinitrobenzenesulfonyl groups. Of these groups, 2- or 4-nitrobenzenesulfonyl, and 2,4-dinitrobenzenesulfonyl are preferred. Removal of sulfonyl group from the compound formula XXI is carried out under conditions as known methods cited therein.

The compound of formula XXI can be prepared under Mitsunobu reaction condition, as defined below, from sulfonamide of formula XX and R$^5$—OH. Alternatively, the compound of formula XXI can also be prepared from compound formula XX by the same procedure as shown in Scheme 8.

The Mitsunobu reaction is carried out in the presence of reagent(s). There is likewise no particular restriction on the nature of the reagents used, and any reagent commonly used in reactions of this type may equally be used here. Examples of such reagents include but are not limited to:

(a) a combination of (a1) dialkyl azodicarboxylate such as diethyl azodicarboxylate (DEAD), dimethyl azodicarboxylate (DMAD) and diisopropyl azodicarboxylate (DIAD) and (a2) trialkylphosphine such as tributylphosphine (TBP) or triarylphosphine such as triphenylphosphine (TPP);

(b) a combination of (b1) tetraalkyldiazocarboxamide such as N,N,N',N'-tetraisopropylazodicarboxamide (TIPA) and N,N,N',N'-tetramethylazodicarboxamide (TMAD) and (b2) trialkylphosphine such as tributylphosphine (TBP) or triarylphosphine such as triphenylphosphine (TPP);

(c) phosphorane such as cyanomethylenetributylphosphorane (CMBP), cyanomethlenetrimethylphosphorane and dimethyl (tributylphosphoranylidene)malonate (DMTP).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: aliphatic hydrocarbons, such as hexane, heptane, and petroleum ether; halogenated hydrocarbons, such as dichloromethane, chloroform, carbon tetrachloride, and dichloroethane; ethers, such as diethyl ether, diisopropyl ether, THF, dimethoxyethane, and dioxane; aromatic hydrocarbons, such as benzene, toluene, xylene, chlorobenzene, dichlorobenzene, and nitrobenzene; amides, such as formamide, DMF, N,N-dimethylacetamide, and hexamethylphosphoric triamide; amines, such as N-methylmorpholine, triethylamine, tripropylamine, tributylamine, diisopropylethylamine, pyridine, 4-pyrrolidinopyridine, N,N-dimethylaniline, and N,N-diethylaniline; nitriles, such as acetonitrile and benzonitrile; sulfoxides, such as dimethyl sulfoxide, and sulfolane. Of these solvents, toluene, benzene, xylene, chlorobenzene, dichlorobenzene, THF, diethylether, diisopropylether, dimethoxyethane, acetonitrile, dichloromethane, dichloroethane, and chloroform are preferred.

The compound of formula V is prepared by removal of sulfonyl protecting group from the intermediate of formula XXI as shown in the Scheme 9, according to the procedures similar to those described in Protective Groups in Organic Synthesis edited by T. W. Greene et al. (John Wiley & Sons, 1999). Typical conditions for removal of the protecting groups employ, but are not limited to:

(a) Strong acid such as hydrogen bromide (HBr) (Haskell, B., E., et. al., J. Org. Chem, 41, 159 (1976)), and the like.

(b) Strong nucleophile such as excess amount of propyl amine, thiobenzene, thioacetic acid (Fukuyama, T., et. al., Tetrahedron Lett., 36, 6373 (1995), Fukuyama, T., et. al., Tetrahedron Lett., 38, 5831 (1997)), and the like.

(c) Reducing agent such as dissolving metal like sodium in tert-butanol (Merlin, P., et. al., Tetrahedron Lett., 29, 1691 (1988) or lithium in liquid ammonia (Heathcock, C. H., et. al., J. Am. Chem. Soc., 108, 5022 (1986), hydride reagents like lithium aluminum hydride (Bell, K. E., et. al., Tetrahedron Lett., 36, 8681 (1995)), and the like.

The compounds of general formula I of the present invention can also be prepared in a convergent manner as described in reaction schemes 10, 11 and 12. The carboxylic acid protected amino acid derivatives XXI are, in many cases, commercially available. In Reaction Scheme 10, PG2 is a carboxy-protecting group. The term "carboxy-protecting group", as used herein, signifies a protecting group capable of being cleaved by chemical means, such as hydrogenolysis, hydrolysis, electrolysis, or photolysis, and such carboxy-protecting groups are described in Protective Groups in Organic Synthesis edited by T. W. Greene et al. (John Wiley & Sons, 1999). Typical carboxy-protecting groups include, but are not limited to: methyl, ethyl, t-butyl, methoxymethyl, 2,2,2-trichloroethyl, benzyl, diphenylmethyl, trimethylsilyl, t-butyldimethylsilyl and allyl. Of these groups, t-butyl or methyl are preferred.

Scheme 10

{Chem. 14}

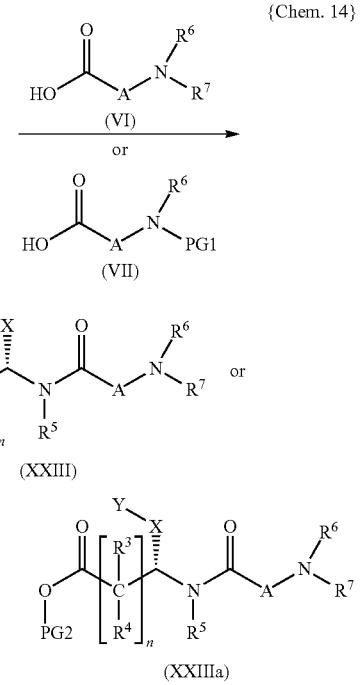

Intermediates of formula XXIII or XXIIIa, can be prepared as shown in Scheme 10 by coupling of amino acid esters XXII to amino acids of formula VI or VII. When a urea linkage is present in XXIII or XXIIIa, it can be introduced as illustrated in Scheme 7.

Scheme 11

{Chem. 15}

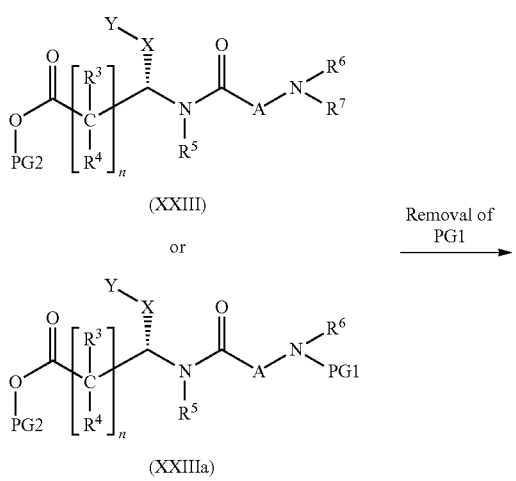

Removal of PG1

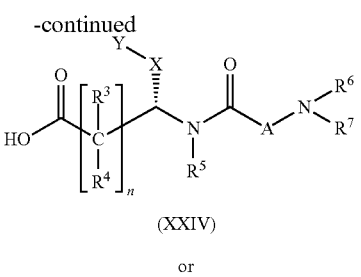

(XXIV)

or

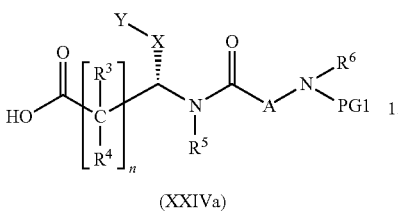

(XXIVa)

Conversion of the ester XXIII or XXIIIa to intermediate acids XXIV or XXIVa can be achieved by a number of methods known in the art as described in Scheme 11. For example, methyl and ethyl esters can be hydrolyzed with lithium hydroxide or sodium hydroxide or potassium hydroxide in a protic solvent like aqueous alcohol, such as methanol, ethanol, and 2-propanol. In addition, removal of benzyl group can be accomplished by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see J. Org. Chem., 42, 587 (1982)).

Acid XXIV or XXIVa can then be elaborated to I or compound VIII as described in Scheme 12. Coupling of piperidines of formula II to acids of formula)(XIV or XXIVa, wherein PG1 is a suitable protecting group as defined above, is conveniently carried out under the standard peptide coupling reaction conditions. Transformation of VIII to I is achieved by removal of the protecting group PG1. When $R^6$ and/or $R^7$ is hydrogen, substituted alkyl groups may be optionally added to the nitrogen atom as described in Scheme 4.

Scheme 13

{Chem. 17}

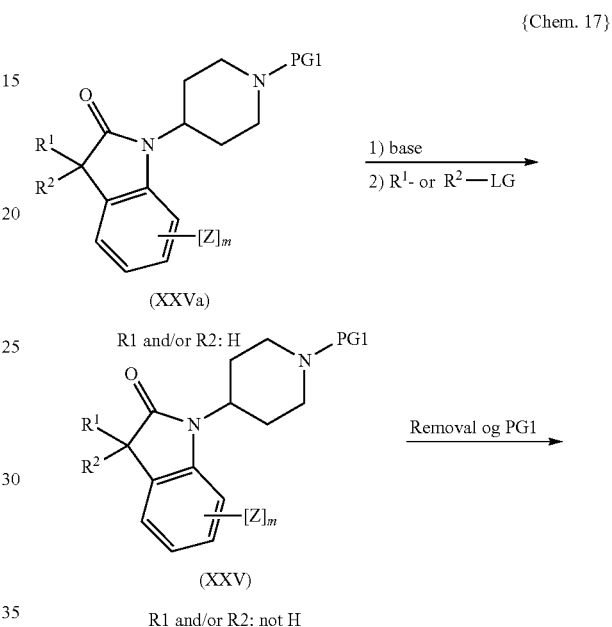

Scheme 12

{Chem. 16}

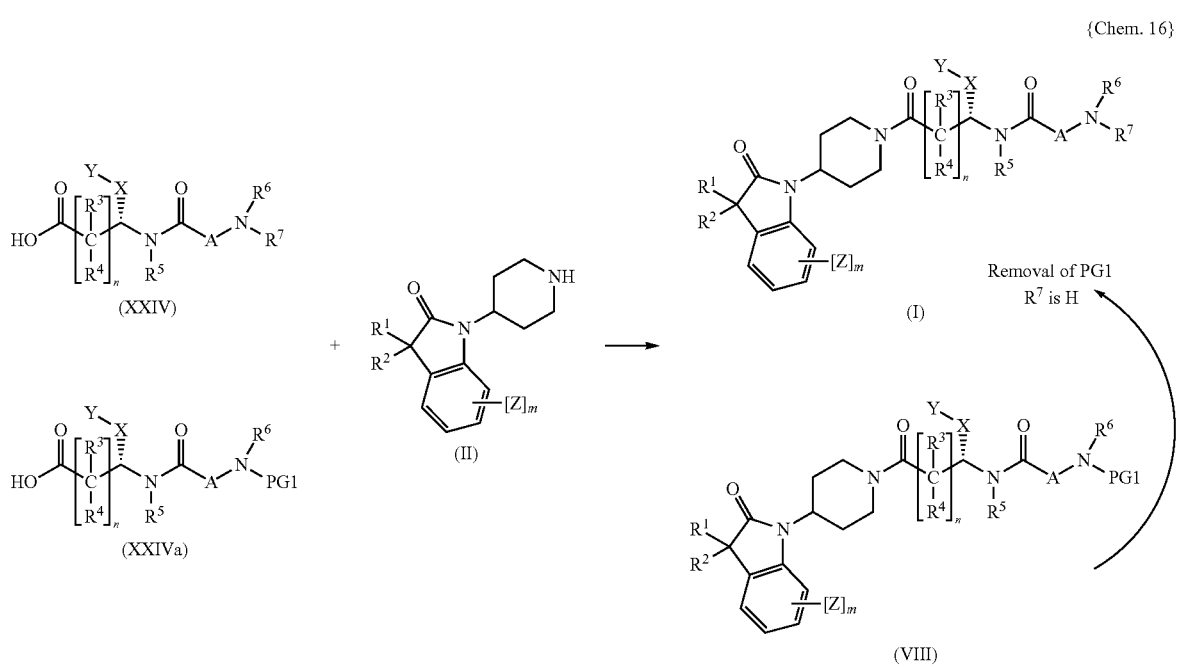

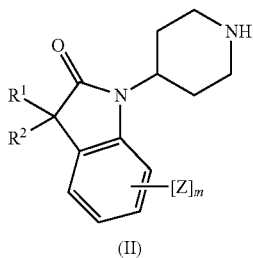

(II)

When R¹ and/or R² is/are hydrogen, the piperidines of formula II can be prepared from the intermediates, XXVa by alkylation and followed removal of protecting group PG1 as shown in Scheme 13. Wherein the leaving group, LG and amino protecting group, PG1 are defined as above.

The procedure of alkylation protocol detailed by Dounay et al. (J. Am Chem. Soc., 125, 6261-6271 (2003)).

Scheme 14

{Chem. 18}

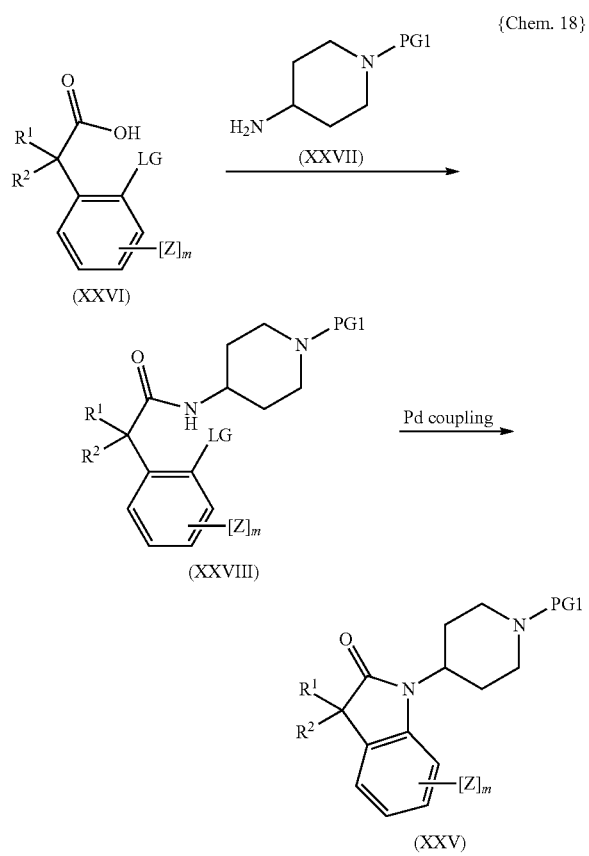

The compounds of formula XXV can be prepared by intermolecular palladium coupling as shown in scheme 14. The intermediates of the formula XXVIII is prepared by the standard peptide coupling reaction of acids of formula XXVI and piperidines of formula XXVII. The palladium catalyzed coupling reaction is carried out under the known procedure (Hoogenband et al., Tetrahedron Lett., 45 (2004) 8535).

Scheme 15

{Chem. 19}

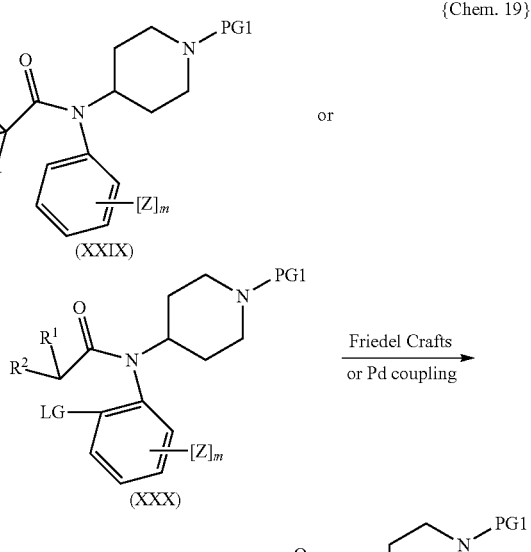

The compounds of formula XXV can be prepared by Friedel-Crafts reaction or intermolecular palladium coupling as shown in Scheme 15. The protocols of Friedel-Crafts reaction and palladium coupling reaction of formula XXIX and XXX are carried out under known procedures (Zaveri, N. et al., J. Med. Chem., 47, (2004), 2973-2976., Buchwald, S., J. Am. Chem. Soc., 125, (2003), 12084-12085., Lee, S. et al., J. Org. Chem. 66 (2001), 3402-3415.) Preparation of the intermediates of formula XXIX and XXX are carried out according to the cited protocols in above literatures.

EXAMPLES

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (tlc) and reaction times are given for illustration only; the structure and purity of all isolated compounds were assured by at least one of the following techniques: tlc (Merck silica gel 60 $F_{254}$ precoated TLC plates or Merck $NH_2$ $F_{254}$ precoated HPTLC plates), mass spectrometry or nuclear magnetic resonance (NMR). Yields are given for illustrative purposes only. Flash column chromatography was carried out using Merck silica gel 60 (230-400 mesh ASTM) or Fuji Silysia Chromatorex(registered trademark) DU3050 (Amino Type, 30-50 micrometer) or Biotage silica (32-63 mm, KP-Sil) or Biotage amino bounded silica (35-75 mm, KP-NH). The purification of compounds using HPLC was performed by the following apparatus and conditions ("process A"); Apparatus; Waters MS-trigger AutoPurification™ system Column; Waters XTerra C18, 19×50 mm, 5 mm particle, Method A; Methanol or acetonitrile/0.05%(v/v) formic acid aqueous solution, Method B; Methanol or acetonitrile/0.01%(v/v) ammonia aqueous solution. The purification using HPLC ("Process B") was performed by the following apparatus and conditions: Apparatus; UV-trigger preparative HPLC system, Waters (Column; XTerra MS C18, 5 micrometer, 19×50 mm or 30×50 mm), Detector; UV 254 nm, Conditions; acetonitrile:0.05% formic acid aqueous solution or acetonitrile:0.01% aqueous ammonia solution; 20 mL/min (19×50 mm) or 40 mL/min (30×50 mm) at room temperature. Low-resolution mass spectral data (ESI) were obtained by the following apparatus and conditions: Apparatus; Waters Alliance HPLC system on ZQ or ZMD mass spectrometer and UV detector. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; microL (microliter(s)), microg (microgram(s)), M (mol(s) per liter), L (liter(s)), mL (milliliter(s)), g (gram(s)), mg (milligram(s)), mol (mole(s)), mmol (millimole(s)).

Conditions for Determining HPLC Retention Time:

Method A:

Apparatus: Waters Acquity Ultra Performance LC on TUV Detector and ZQ mass spectrometer Column: Waters ACQUITY C18, 2.1×50 mm, 1.7 micrometer particle Column Temperature: 60° C.

Solvents:

A1: 10 mM ammonium acetate aqueous solution

B1: acetonitrile

TABLE 1

| Time(min) | A1(%) | B1(%) |
|---|---|---|
| 0 | 95 | 5 |
| 0.1 | 95 | 5 |
| 0.8 | 5 | 95 |
| 1 | 95 | 5 |
| run time | | 1.5 min |
| flow | | 1 mL/min |

Method B:

Apparatus: Waters Acquity Ultra Performance LC on TUV Detector and ZQ mass spectrometer Column: Waters SunFire C18 2.1×50 mm, 3.5 micrometer particle Column Temperature: 40° C.

Solvents:

A: water

B: acetonitrile

C: 1% (v/v) formic acid aqueous solution

TABLE 2

| Time(min) | A(%) | B(%) | C(%) |
|---|---|---|---|
| 0 | 90 | 5 | 5 |
| 0.5 | 90 | 5 | 5 |
| 3.5 | 0 | 95 | 5 |
| 4.5 | 90 | 5 | 5 |
| run time | | | 5 min |
| flow | | | 1 mL/min |

Method C:

Apparatus: Waters Acquity Ultra Performance LC on TUV Detector and ZQ mass spectrometer Column: Waters ACQUITY C18, 2.1×100 mm, 1.7 micrometer particle Column Temperature: 60° C.

Solvents:

A1: 10 mM ammonium acetate aqueous solution

B1: acetonitrile

TABLE 3

| Time(min) | A1(%) | B1(%) |
|---|---|---|
| 0 | 95 | 5 |
| 0.1 | 95 | 5 |
| 1.8 | 5 | 95 |
| 2.3 | 95 | 5 |
| run time | | 3 min |
| flow | | 0.7 mL/min |

Example 1

(R)—N—((S)-1-(4-(3,3-dimethyl-2-oxoindolin-1-yl)piperidin-1-yl)-1-oxo-4-phenylbutan-2-yl)piperidine-3-carboxamide {Chem. 20}

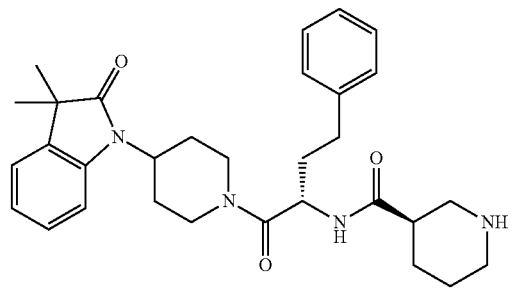

Step 1.

1-(1-benzylpiperidin-4-yl)-3,3-dimethylindolin-2-one

To a stirred solution of N,N-diisopropylethylamine (28.9 mL, 205 mmol) and dry tetrahydrofuran (446 mL) cooled to −78° C. was added drop-wise n-butyl lithium (82.3 mL, 205 mmol) under nitrogen atmosphere. The reaction mixture was stirred at −78° C. for 10 min then 1-(1-benzylpiperidin-4-yl)indolin-2-one (21.0 g, 68.0 mmol, Tetrahedron Letters, 2004, 50, 8535-8537) in tetrahydrofuran (258 mL) was added drop-wise. The reaction mixture was stirred for another 30 min, and iodomethane (12.8 mL, 205 mmol) was added. The reaction mixture was warmed up to room temperature and stirred for overnight. The reaction mixture was cooled to 0° C. and ammonium chloride aqueous solution was added to quench the reaction. The aqueous layer was extracted with ethyl acetate (×3). The organic layers were combined, dried over sodium sulfate and concentrated. The residue was purified by silica gel column chromatography using 10% ethyl acetate in hexane to give the title compound (19.0 g, 83%).

$^1$H NMR (CDCl$_3$) δ: 7.31-7.25 (4H, m), 7.21-7.10 (4H, m), 7.10-6.94 (1H, m), 4.27-4.21 (1H, m), 3.49 (2H, s), 2.97-2.94 (2H, m), 2.44-2.36 (2H, m), 2.11-2.05 (2H, m), 1.62-1.58 (2H, m), 1.28 (6H, s).

Step 2.

3,3-dimethyl-1-(piperidin-4-yl)indolin-2-one hydrochloride 1-(1-Benzylpiperidin-4-yl)-3,3-dimethylindolin-2-one (17.0 g, 50.8 mmol, Step 1) and palladium on carbon (19.7 g) were added to ethanol (442 mL). The reaction mixture was heated to 60° C. under hydrogen atmosphere for 10 h. The reaction mixture was filtered and the filtrate was concentrated to about 50 mL. Diethyl ether (200 mL) was added, and the following mixture was adjusted to pH 3 with saturated hydrogen chloride in methanol. White solids were filtered and dried in vacuo to give the title compound (7.5 g, 53%).

$^1$H NMR (CDCl$_3$) δ: 7.33-7.29 (2H, m), 7.23-7.21 (1H, m), 7.13-7.09 (1H, m), 4.46-4.40 (1H, m), 3.59-3.56 (2H, m), 3.26-3.18 (2H, m), 2.83-2.72 (2H, m), 2.01-1.98 (2H, m), 1.34 (6H, s).

Step 3.
(S)-tert-butyl

1-(4-(3,3-dimethyl-2-oxoindolin-1-yl)piperidin-1-yl)-1-oxo-4-phenylbutan-2-ylcarbamate To a mixture of 3,3-dimethyl-1-(piperidin-4-yl)indolin-2-one hydrochloride (2.00 g, 7.12 mmol, EXAMPLE 1, Step 2) and (S)—N-tert-butoxycarbonyl-homophenylalanine (2.09 g, 7.48 mmol) in dichloromethane (30 mL) at 0° C. was added triethylamine (3.50 mL, 24.9 mmol), 1-ethyl-3-(3-dimethylaminopropyl)-carbodiimide hydrochloride (1.64 g, 8.55 mmol) and 1-hydroxybenzotriazole hydrate (1.16 g, 8.55 mmol). Then the mixture was stirred for 24 h. The reaction was quenched with water, and volatiles were removed in vacuo. The residue was diluted with ethyl acetate (100 mL). The organic layer was washed with 0.5 mol/L hydrochloric acid (40 mL×3), 0.5 mol/L sodium hydroxide aqueous solution (40 mL×2) and brine (30 mL), dried over magnesium sulfate and concentrated to give the title compound (2.79 g, 77%) as a solid.

$^1$H NMR (CDCl$_3$) δ: 7.25-7.08 (7H, m), 7.00-6.95 (2H, m), 5.45-5.35 (1H, m), 4.75-4.25 (3H, m), 3.80-3.60 (1H, m), 3.09-2.90 (1H, m), 2.70-2.55 (3H, m), 2.35-2.15 (2H, m), 2.00-1.60 (4H, m), 1.43-1.41 (9H, pseudo d), 1.29-1.22 (6H, pseudo d).

Step 4.

(S)-1-(1-(2-amino-4-phenylbutanoyl)piperidin-4-yl)-3,3-dimethylindolin-2-one hydrochloride A mixture of (S)-tert-butyl 1-(4-(3,3-dimethyl-2-oxoindolin-1-yl)piperidin-1-yl)-1-oxo-4-phenylbutan-2-ylcarbamate (2.79 g, 5.52 mmol, EXAMPLE 1, Step 3) and 1 mol/L hydrochloride in diethyl ether (25 mL) was stirred at room temperature. After 4 h, a mixture of chlorotrimethylsilane (2 mL) and methanol (4 mL) was added to the reaction suspension. The whole mixture changed to a clear solution and was stirred for 3 h. The mixture was concentrated in vacuo and the residue was diluted with diethyl ether and re-concentrated to remove methanol completely. The obtained solid was washed with diethyl ether to give the title compound (2.05 g, 84%).

$^1$H NMR (CDCl$_3$) δ: 8.38-8.25 (3H, m), 7.45-6.74 (9H, m), 4.68-4.56 (2H, m), 4.45-4.10 (1H, m), 3.63-3.44 (1H, m), 3.05-2.75 (3H, m), 2.57-2.05 (5H, m), 1.65-1.44 (2H, m), 1.26-1.23 (6H, pseudo d).

MS (ESI) m/z: 406 (M+H)$^+$.

Step 5.

(R)—N—((S)-1-(4-(3,3-dimethyl-2-oxoindolin-1-yl)piperidin-1-yl)-1-oxo-4-phenylbutan-2-yl)piperidine-3-carboxamide To a solution of (S)-1-(1-(2-amino-4-phenylbutanoyl)piperidin-4-yl)-3,3-dimethylindolin-2-one hydrochloride (45 mg, 0.10 mmol, EXAMPLE 1, Step 4) were added (R)—N-Boc-piperidine-3-carboxylic acid (31 mg, 0.14 mmol) and 2-(1H-benzotriazole-1-yl)-1,1,3,3-tetramethyluronium hexafluorophosphate (53 mg, 0.14 mmol), and the mixture was stirred at 60° C. for 6 h, then at room temperature for 13 h. Volatiles were removed in vacuo.

To the residue dissolved in 1,2-dichloroethane (1 mL) was added 2,2,2-trifluoroacetic acid (1 mL), and the mixture was stirred at room temperature for 2 h. Then the mixture was concentrated in vacuo. The residue was diluted with methanol and applied onto a strong cation exchange cartridge (Bond-Elute(registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo. The residue was purified by preparative LC-MS to give the title compound (22.7 mg, 44%).

MS (ESI) m/z: 517 (M+H)$^+$.
HPLC retention time: 0.72 min. (Method A).

Example 1

Alternative Method

Step 1.
(R)-tert-butyl

3-((S)-1-(4-(3,3-dimethyl-2-oxoindolin-1-yl)piperidin-1-yl)-1-oxo-4-phenylbutan-2-ylcarbamoyl)piperidine-1-carboxylate To a mixture of (S)-1-(1-(2-amino-4-phenylbutanoyl)piperidin-4-yl)-3,3-dimethylindolin-2-one hydrochloride (500 mg, 1.13 mmol, EXAMPLE 1, Step 4), (R)—N-Boc-piperidine-3-carboxylic acid (389 mg, 1.70 mmol) and triethylamine (556 microL, 3.96 mmol) in dimethyl formamide (8 mL) were added 1-ethyl-3-(3-dimethylamino)propyl carbodiimide hydrochloride (347 mg, 1.81 mmol) and 1-hydroxybenztriazole hydrate (277 mg, 1.81 mmol). After stirring for 17 h, the mixture was diluted with ethyl acetate and water. The organic layer was washed with saturated sodium hydrogen carbonate aqueous solution and brine, dried over sodium sulfate and concentrated in vacuo. The residue was purified with silica gel column chromatography (hexane/ethyl acetate) and amine gel column chromatography (hexane/ethyl acetate,) to give the title compound (615 mg, 88%) as an amorphous solid.

$^1$H NMR (CDCl$_3$) δ: 7.33-7.08 (m, 7H), 7.01-6.85 (m, 2H), 6.68-6.58 (m, 1H), 5.03-4.93 (m, 1H), 4.83-4.70 (m, 1H), 4.52-4.30 (m, 1H), 4.23-4.06 (m, 2H), 4.04-3.88 (m, 1H), 3.76 (m, 1H), 3.11-2.56 (m, 5H), 2.43-2.18 (m, 3H), 2.09-1.57 (m, 8H), 1.48 (s, 9H), 1.38-1.30 (m, 6H).

MS (ESI) m/z: 617 (M+H)$^+$.
Step 2.

(R)—N—((S)-1-(4-(3,3-dimethyl-2-oxoindolin-1-yl)piperidin-1-yl)-1-oxo-4-phenylbutan-2-yl)piperidine-3-carboxamide A mixture of (R)-tert-butyl 3-((S)-1-(4-(3,3-dimethyl-2-oxoindolin-1-yl)piperidin-1-yl)-1-oxo-4-phenylbutan-2-ylcarbamoyl)piperidine-1-carboxylate (615 mg, 0.997 mmol, EXAMPLE 1, Alternative Method, Step 1) and trifluoroacetic acid (2 mL) was stirred for 20 min and concentrated. The residue was diluted with dichloromethane and basified by saturated sodium hydrogen carbonate aqueous solution. The organic layer was dried over sodium sulfate and concentrated in vacuo. The crude product was purified by amine gel column chromatography (dichloromethane/methanol, gradient) to give the title compound (430 mg, 83%) as an amorphous solid.

$^1$H NMR (CDCl$_3$) δ: 8.16-7.84 (m, 1H), 7.55-6.77 (m, 9H), 5.16-4.97 (m, 1H), 4.88-4.71 (m, 1H), 4.58-4.26 (m, 1H), 3.96-3.77 (m, 1H), 3.26-2.54 (m, 9H), 2.48-2.19 (m, 3H), 2.18-1.18 (m, 14H).

MS (ESI) m/z: 517 (M+H)$^+$.

Example 2-16

{Chem. 21}

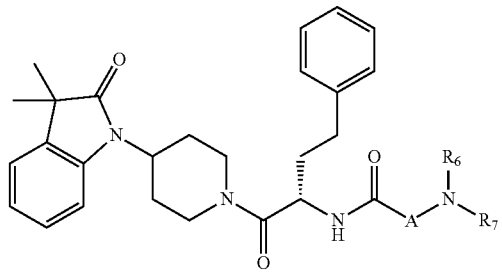

The following examples, EXAMPLE 2-16, were prepared according to the procedure similar to that described in the Step 5 of the EXAMPLE 1, using the appropriate precursor instead of (R)-1-(tert-butoxycarbonyl)piperidine-3-carboxylic acid.

TABLE 4-A

| Example | Structure | Chemical Name | HPLC Gradient Method | HPLC Retention Time (min.) | MS (ESI): m/z (M + H)+ |
|---|---|---|---|---|---|
| 2 | | (S)-N-((S)-1-(4-(3,3-dimethyl-2-oxoindolin-1-yl)piperidin-1-yl)-1-oxo-4-phenylbutan-2-yl)piperidine-2-carboxamide | Method B | 2.17 | 517 |
| 3 | | (S)-2-amino-N-((S)-1-(4-(3,3-dimethyl-2-oxoindolin-1-yl)piperidin-1-yl)-1-oxo-4-phenylbutan-2-yl)-3,3-dimethylbutanamide | Method B | 2.20 | 519 |
| 4 | | (S)-N-((S)-1-(4-(3,3-dimethyl-2-oxoindolin-1-yl)piperidin-1-yl)-1-oxo-4-phenylbutan-2-yl)pyrrolidine-2-carboxamide | Method A | 0.75 | 503 |
| 5 | | (S)-1-amino-N-(1-(4-(3,3-dimethyl-2-oxoindolin-1-yl)piperidin-1-yl)-1-oxo-4-phenylbutan-2-yl)cyclopentanecarboxamide | Method A | 0.82 | 517 |
| 6 | | (S)-2-(1-aminocyclobutyl)-N-(1-(4-(3,3-dimethyl-2-oxoindolin-1-yl)piperidin-1-yl)-1-oxo-4-phenylbutan-2-yl)acetamide | Method A | 0.75 | 517 |
| 7 | | (S)-1-(aminomethyl)-N-(1-(4-(3,3-dimethyl-2-oxoindolin-1-yl)piperidin-1-yl)-1-oxo-4-phenylbutan-2-yl)cyclopropanecarboxamide | Method A | 0.74 | 503 |

TABLE 4-A-continued

| Example | 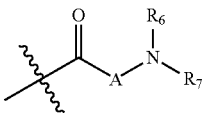 | Chemical Name | HPLC Gradient Method | HPLC Retention Time (min.) | MS (ESI): m/z (M + H)+ |
|---|---|---|---|---|---|
| 8 | 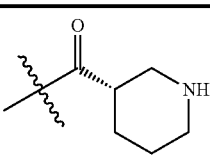 | (S)-N-((S)-1-(4-(3,3-dimethyl-2-oxoindolin-1-yl)piperidin-1-yl)-1-oxo-4-phenylbutan-2-yl)piperidine-3-carboxamide | Method A | 0.74 | 517 |

TABLE 4-B

| Example | 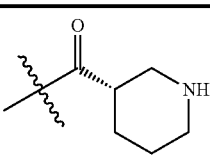 | Chemical Name | HPLC Gradient Method | HPLC Retention Time (min.) | MS (ESI): m/z (M + H)+ |
|---|---|---|---|---|---|
| 9 | 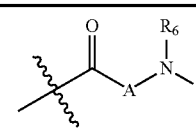 | (S)-N-(1-(4-(3,3-dimethyl-2-oxoindolin-1-yl)piperidin-1-yl)-1-oxo-4-phenylbutan-2-yl)azetidine-3-carboxamide | Method B | 2.15 | 489 |
| 10 | 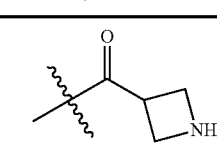 | (S)-N-(1-(4-(3,3-dimethyl-2-oxoindolin-1-yl)piperidin-1-yl)-1-oxo-4-phenylbutan-2-yl)piperidine-4-carboxamide | Method A | 0.72 | 517 |
| 11 | 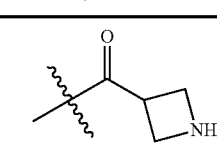 | (S)-N-(1-(4-(3,3-dimethyl-2-oxoindolin-1-yl)piperidin-1-yl)-1-oxo-4-phenylbutan-2-yl)-3-(methylamino)cyclobutane-carboxamide | Method A | 0.72 | 517 |
| 12 | 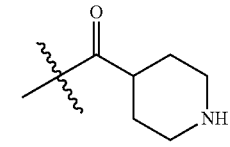 [SMILES: *C(=O)C1CCNCC1] | (S)-2-(1-aminocyclopentyl)-N-(1-(4-(3,3-dimethyl-2-oxoindolin-1-yl)piperidin-1-yl)-1-oxo-4-phenylbutan-2-yl)acetamide | Method B | 2.25 | 531 |
| 13 | 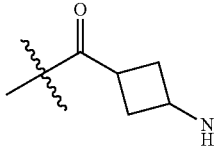 | (S)-N-(1-(4-(3,3-dimethyl-2-oxoindolin-1-yl)piperidln-1-yl)-1-oxo-4-phenylbutan-2-yl)-3-methyl-3-(methylamino)butanamide | Method A | 0.74 | 519 |
| 14 | 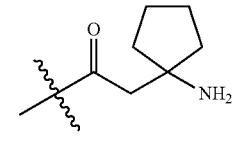 [SMILES: *C(=O)CC1(N)CCCC1] | (S)-3-(cyclopentylamino)-N-(1-(4-(3,3-dimethyl-2-oxoindolin-1-yl)piperidin-1-yl)-1-oxo-4-phenylbutan-2-yl)propanamide | Method A | 0.78 | 545 |
| 15 | 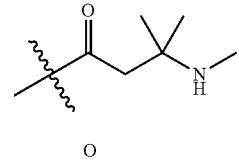 | (S)-N-(1-(4-(3,3-dimethyl-2-oxoindolin-1-yl)piperidin-1-yl)-1-oxo-4-phenylbutan-2-yl)-3-((2-methoxyethyl)(methyl)amino)propanamide | Method B | 2.20 | 549 |

TABLE 4-B-continued

| Example | Chemical Name | HPLC Gradient Method | HPLC Retention Time (min.) | MS (ESI): m/z (M + H)+ |
|---|---|---|---|---|
| 16 | (S)-N-(1-(4-(3,3-dimethyl-2-oxoindolin-1-yl)piperidin-1-yl)-1-oxo-4-phenylbutan-2-yl)-3-(dimethylamino)propanamide | Method B | 2.15 | 505 |

Example 17

(S)—N-(1-(4-(3,3-dimethyl-2-oxoindolin-1-yl)piperidin-1-yl)-1-oxo-4-phenylbutan-2-yl)-2-(pyrrolidin-1-yl)acetamide {Chem. 22}

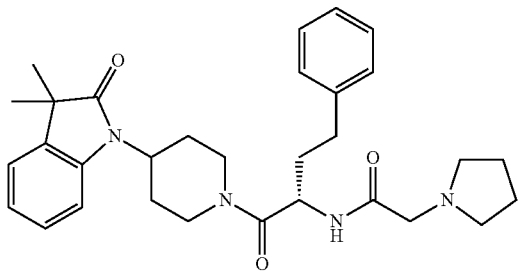

Step 1.

(S)-2-chloro-N-(1-(4-(3,3-dimethyl-2-oxoindolin-1-yl)piperidin-1-yl)-1-oxo-4-phenylbutan-2-yl)acetamide To a solution of chloroacetyl chloride (120 microL, 1.49 mmol) in dichloromethane (5 mL) was slowly added a mixture of (S)-1-(1-(2-amino-4-phenylbutanoyl)piperidin-4-yl)-3,3-dimethylindolin-2-one hydrochloride (600 mg, 1.36 mmol, EXAMPLE 1, Step 4) and triethylamine (420 microL, 2.99 mmol) in dichloromethane (4 mL) at 0° C. After 5 min, the reaction was quenched with water and the mixture was diluted with ethyl acetate to separate. The organic layer was washed with water (×2) and brine, dried over sodium sulfate and concentrated to give the title compound. The product was diluted with 6.0 mL of tetrahydrofuran to give 0.226 mol/L tetrahydrofuran solution assuming 100% conversion. The stock solution was used for the next step without further purification.

MS (ESI) m/z: 482 M ($^{35}$Cl)$^+$, 484 M ($^{37}$Cl)$^+$.

Step 2.

(S)—N-(1-(4-(3,3-dimethyl-2-oxoindolin-1-yl)piperidin-1-yl)-1-oxo-4-phenylbutan-2-yl)-2-pyrrolidin-1-yl)acetamide To a solution of pyrrolidine (16.9 microL, 0.204 mmol) was added (S)-2-chloro-N-(1-(4-(3,3-dimethyl-2-oxoindolin-1-yl)piperidin-1-yl)-1-oxo-4-phenylbutan-2-yl)acetamide (0.226 mol/L tetrahydrofuran solution, 300 microL, 0.0679 mmol, EXAMPLE 17, Step 1) at room temperature. After stirring at 60° C. for 2 h, the mixture was concentrated. The residue was diluted with methanol (4 mL). The residue was diluted with methanol and applied onto a strong cation exchange cartridge (BondElute(registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo. The residue was purified by preparative LC-MS to give the title compound (12.2 mg, 35%).

MS (ESI) m/z: 517 (M+H)$^+$.
HPLC retention time: 2.19 min. (Method B).

Example 18-19

{Chem. 23}

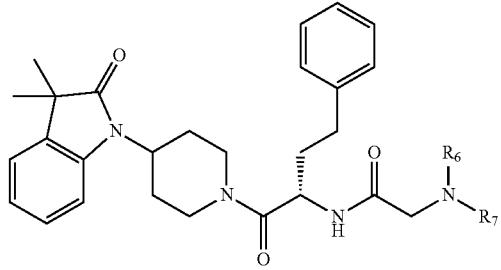

The following examples, EXAMPLE 18-19, were prepared according to the procedure similar to that described in the Step 1 through 2 of the EXAMPLE 17, using the appropriate precursor instead of pyrrolidine.

TABLE 5

| Example | Chemical Name | HPLC Gradient Method | HPLC Retention Time (min.) | MS (ESI): m/z (M + H)+ |
|---|---|---|---|---|
| 18 | (S)-2-(cyclopentylamino)-N-(1-(4-(3,3-dimethyl-2-oxoindolin-1-yl)piperidin-1-yl)-1-oxo-4-phenylbutan-2-yl)acetamide | Method B | 2.24 | 531 |

TABLE 5-continued

| Example | Chemical Name | HPLC Gradient Method | HPLC Retention Time (min.) | MS (ESI): m/z (M + H)+ |
|---|---|---|---|---|
| 19 | N-((S)-1-(4-(3,3-dimethyl-2-oxoindolin-1-yl)piperidin-1-yl)-1-oxo-4-phenylbutan-2-yl)-2-((R)-3-methylpiperazin-1-yl)acetamide | Method B | 2.17 | 546 |

Example 20

(R)—N—((S)-1-(4-(3,3-dimethyl-2-oxoindolin-1-yl)piperidin-1-yl)-1-oxo-4-phenylbutan-2-yl)-1-methylpiperidine-3-carboxamide {Chem. 24}

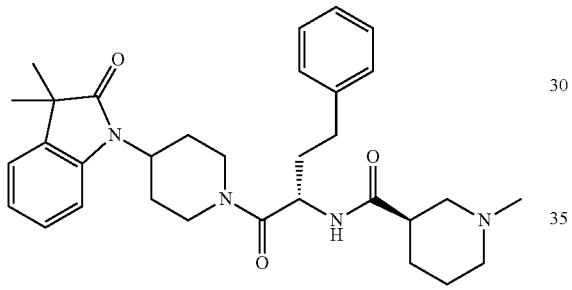

Step 1

(R)—N—((S)-1-(4-(3,3-dimethyl-2-oxoindolin-1-yl)piperidin-1-yl)-1-oxo-4-phenylbutan-2-yl)-1-methylpiperidine-3-carboxamide A mixture of (S)-1-(1-(2-amino-4-phenylbutanoyl)piperidin-4-yl)-3,3-dimethylindolin-2-one hydrochloride (30 mg, 0.068 mmol), (R)—N-Boc-piperidine-3-carboxylic acid (31 mg, 0.14 mmol), triethylamine (29 microL, 0.20 mmol) and 2-(1H-benzotriazole-1-yl)-1,1,3,3-tetramethyluronium hexafluorophosphate (52 mg, 0.14 mmol) in dimethyl formamide (1 mL) was stirred for 1.5 h at room temperature. The reaction mixture was diluted with water (2 mL) and ethyl acetate (6 mL). The organic layer was washed with aq. sodium bicarbonate (2 mL×2), filtered through magnesium sulfate column and concentrated. The residue was added trifluoroacetic acid (1 mL) and stirred for 10 min.

After removal of trifluoroacetic acid, the residue was diluted with methanol (4 mL) and the solution was filtered through a strong cation exchange cartridge (BondElute(registered trademark) SCX, 1 g/6 mL, Varian Inc.). The column was washed with 1 mol/L ammonia in methanol (2 mL×3) and the filtrate was concentrated. The residue was dissolved in dichloromethane (1.5 mL) and methanol (0.15 mL). To the solution was added paraformaldehyde (6.1 mg, 0.20 mmol) and sodium triacetoxyborohydride (43 mg, 0.20 mmol) at room temperature. After 1 h, further sodium triacetoxyborohydride (200 mg) was added to the mixture and the mixture was stirred. After 10 min, the mixture was concentrated and the residue was basified with sodium hydrogen carbonate aqueous solution and extracted with ethyl acetate (3 mL×2). The organic layer was filtered through magnesium sulfate column and the filtrate was concentrated in vacuo. The crude product was purified by preparative LC-MS to give the title compound (17.4 mg, 48%).

MS (ESI) m/z: 531 (M+H)⁺.

HPLC retention time: 0.75 min. (Method A).

Example 21

(1S,3R)—N—((S)-3-(4-chlorophenyl)-1-(4-(3,3-dimethyl-2-oxoindolin-1-yl)piperidin-1-yl)-1-oxopropan-2-yl)-3-(methylamino)cyclopentanecarboxamide {Chem. 25}

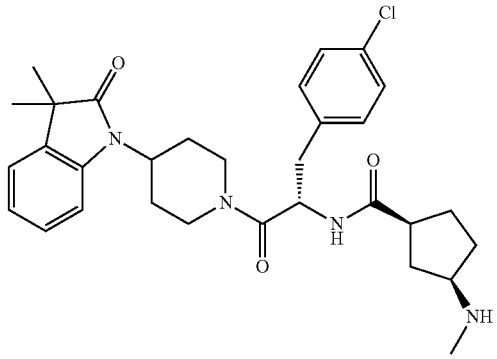

Step 1.

(1S,3R)-3-(tert-butoxycarbonyl(methyl)amino)cyclopentanecarboxylic acid

To a stirred suspension of sodium hydride (89 mg, 2.24 mmol) in tetrahydrofuran (10 mL) and dimethyl formamide (10 mL) cooled in an ice bath was added (1S,3R)-3-(tert-butoxycarbonylamino)cyclopentanecarboxylic acid (427 mg, 1.86 mmol, WO2006/011035) and iodomethane (128 microL, 2.05 mmol). The mixture was allowed to warm to room temperature and stirred for 20 h. Sodium hydride (178 mg, 4.474 mmol) and idomethan (256 microL, 4.102 mmol) were added, and the reaction mixture was stirred at 20 h at room temperature. Reaction mixture was acidified to pH 3.5 with 1 mol/L hydrochloric acid and extracted with ethyl acetate. Organic layer was dried over sodium sulfate and concentrated under reduced pressure. Crude material was purified by column chromatography (50% ethyl acetate in hexane containing 1.5% acetic acid) to give the desired compound as a colorless solid (138.0 mg, 31%).

MS (ESI) m/z: 242 (M−H)⁻.

Step 2.

(S)-1-(1-(2-amino-3-(4-chlorophenyl)propanoyl)piperidin-4-yl)-3,3-dimethylindolin-2-one To a solution of 3,3-dimethyl-1-(piperidin-4-yl)indolin-2-one hydrochloride (45 mg, 0.10 mmol, EXAMPLE 1, Step 2) in 3.75% triethylamine/N,N-dimethylacetamide (1.5 mL) were added (S)-2-(tert-butoxycarbonylamino)-3-(4-chlorophenyl)propanoic acid (32.9 mg, 0.11 mmol) and 2-(1H-benzotriazole-1-yl)-1,1,3,3-tetramethyluronium hexafluorophosphate (38 mg, 0.15 mmol), and the mixture was stirred at 60° C. for 6 h and at room temperature for 13 h. Volatiles were removed in vacuo.

To the residue dissolved in 1,2-dichloroethane (1 mL) was added 2,2,2-trifluoroacetic acid (1 mL), and the mixture was stirred at room temperature for 2 h. Then the mixture was concentrated in vacuo. The residue was diluted with methanol and applied onto a strong cation exchange cartridge (Bond-Elute(registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo. The residues were used in the next step without further purification.

Step 3.

(1S,3R)—N—((S)-3-(4-chlorophenyl)-1-(4-(3,3-dimethyl-2-oxoindolin-1-yl)piperidin-1-yl)-1-oxopropan-2-yl)-3-(methylamino)cyclopentanecarboxamide To a solution of (S)-1-(1-(2-amino-3-(4-chlorophenyl)propanoyl)piperidin-4-yl)-3,3-dimethylindolin-2-one (EXAMPLE 21, Step 2) were added (1S,3R)-3-(tert-butoxycarbonyl(methyl)amino)cyclopentanecarboxylic acid (26.7 mg, 0.11 mmol, EXAMPLE 21, Step 1) and 2-(1H-benzotriazole-1-yl)-1,1,3,3-tetramethyluronium hexafluorophosphate (53 mg, 0.14 mmol), and the mixture was stirred at 60° C. for 6 h, then at room temperature for 13 h. Volatiles were removed in vacuo.

To the residue dissolved in 1,2-dichloroethane (1 mL) was added 2,2,2-trifluoroacetic acid (1 mL), and the mixture was stirred at room temperature for 2 h. Then the mixture was concentrated in vacuo. The residue was diluted with methanol and applied onto a strong cation exchange cartridge (Bond-Elute(registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo. The residue was purified by preparative LC-MS to give the title compound (16.2 mg, 29%).

MS (ESI) m/z: 551 (M+H)⁺.

HPLC retention time: 0.74 min (Method A).

Example 22-43

{Chem. 26}

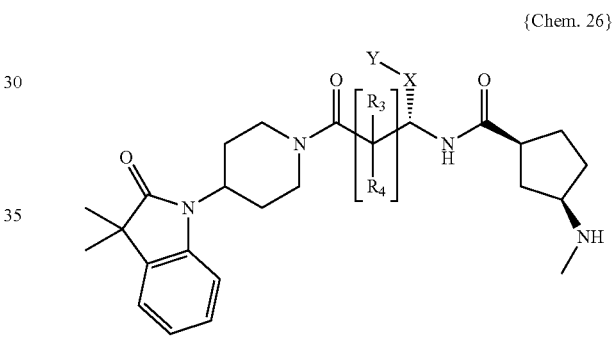

The following examples, EXAMPLE 22-43, were prepared according to the procedure described in the Step 2 through 3 of the EXAMPLE 21, using the appropriate amino acid precursor instead of (S)-2-(tert-butoxycarbonylamino)-3-(4-chlorophenyl)propanoic acid.

TABLE 6-A

| Example | Structure | Chemical Name | HPLC Gradient Method | HPLC Retention Time (min.) | MS (ESI): m/z (M + H)+ |
|---|---|---|---|---|---|
| 22 | [structure with CF₃ phenyl group] | (1S,3R)-N-((S)-1-(4-(3,3-dimethyl-2-oxoindolin-1-yl)piperidin-1-yl)-1-oxo-3-(2-(trifluoromethyl)phenyl)propan-2-yl)-3-(methylamino)cyclopentanecarboxamide | Method A | 0.75 | 585 |

TABLE 6-A-continued

| Example | Structure | Chemical Name | HPLC Gradient Method | HPLC Retention Time (min.) | MS (ESI): m/z (M + H)+ |
|---|---|---|---|---|---|
| 23 | | (1S,3R)-N-((S)-3-cyclohexyl-1-(4-(3,3-dimethyl-2-oxoindolin-1-yl)piperidin-1-yl)-1-oxopropan-2-yl)-3-(methylamino)cyclopentanecarboxamide | Method A | 0.77 | 523 |
| 24 | | (1S,3R)-N-((S)-1-(4-(3,3-dimethyl-2-oxoindolin-1-yl)piperidin-1-yl)-3-(naphthalen-1-yl)-1-oxopropan-2-yl)-3-(methylamino)cyclopentane-carboxamide | Method A | 0.75 | 567 |
| 25 | | (1S,3R)-N-((S)-3-(2-chlorophenyl)-1-(4-(3,3-dimethyl-2-oxoindolin-1-yl)piperidin-1-yl)-1-oxopropan-2-yl)-3-(methylamino)cyclopentane-carboxamide | Method A | 0.73 | 551 |
| 26 | | (1S,3R)-N-((S)-1-(4-(3,3-dimethyl-2-oxoindolin-1-yl)piperidin-1-yl)-1-oxo-3-o-tolylpropan-2-yl)-3-(methylamino)cyclopentanecarboxamide | Method A | 0.73 | 531 |
| 27 | | (1S,3R)-N-((S)-1-(4-(3,3-dimethyl-2-oxoindolin-1-yl)piperidin-1-yl)-3-(4-fluorophenyl)-1-oxopropan-2-yl)-3-(methylamino)cyclopentane-carboxamide | Method A | 0.71 | 535 |

TABLE 6-B

| Example | Structure | Chemical Name | HPLC Gradient Method | HPLC Retention Time (min.) | MS (ESI): m/z (M + H)+ |
|---|---|---|---|---|---|
| 28 | | (1S,3R)-N-((S)-1-(4-(3,3-dimethyl-2-oxoindolin-1-yl)piperidin-1-yl)-3-(3-fluorophenyl)-1-oxopropan-2-yl)-3-(methylamino)cyclopentanecarboxamide | Method A | 0.71 | 535 |
| 29 | | (1S,3R)-N-((S)-3-(3-chlorophenyl)-1-(4-(3,3-dimethyl-2-oxoindolin-1-yl)piperidin-1-yl)-1-oxopropan-2-yl)-3-(methylamino)cyclopentanecarboxamide | Method A | 0.74 | 551 |
| 30 | | (1S,3R)-N-((S)-1-(4-(3,3-dimethyl-2-oxoindolin-1-yl)piperidin-1-yl)-1-oxo-3-phenylpropan-2-yl)-3-(methylamino)cyclopentanecarboxamide | Method A | 0.7 | 517 |
| 31 | | (1S,3R)-N-((S)-1-(4-(3,3-dimethyl-2-oxoindolin-1-yl)piperidin-1-yl)-3-(3-methoxyphenyl)-1-oxopropan-2-yl)-3-(methylamino)cyclopentanecarboxamide | Method A | 0.71 | 547 |
| 32 | | (1S,3R)-N-((S)-1-(4-(3,3-dimethyl-2-oxoindolin-1-yl)piperidin-1-yl)-3-(2-fluorophenyl)-1-oxopropan-2-yl)-3-(methylamino)cyclopentanecarboxamide | Method A | 0.7 | 535 |

TABLE 6-B-continued

| Example | Structure | Chemical Name | HPLC Gradient Method | HPLC Retention Time (min.) | MS (ESI): m/z (M + H)+ |
|---|---|---|---|---|---|
| 33 | | (1S,3R)-N-((S)-1-(4-(3,3-dimethyl-2-oxoindolin-1-yl)piperidin-1-yl)-4-methyl-1-oxopentan-2-yl)-3-(methylamino)cyclopentanecarboxamide | Method A | 0.7 | 483 |

TABLE 6-C

| Example | Structure | Chemical Name | HPLC Gradient Method | HPLC Retention Time (min.) | MS (ESI): m/z (M + H)+ |
|---|---|---|---|---|---|
| 34 | | (1S,3R)-N-((S)-1-(4-(3,3-dimethyl-2-oxoindolin-1-yl)piperidin-1-yl)-3-(1H-indol-3-yl)-1-oxopropan-2-yl)-3-(methylamino)cyclopentanecarboxamide | Method A | 0.69 | 556 |
| 35 | | (1S,3R)-N-((S)-1-(4-(3,3-dimethyl-2-oxoindolin-1-yl)piperidin-1-yl)-1-oxo-3-(3-(trifluoromethyl)phenyl)propan-2-yl)-3-(methylamino)cyclopentanecarboxamide | Method A | 0.76 | 585 |
| 36 | | (1S,3R)-N-((S)-1-(4-(3,3-dimethyl-2-oxoindolin-1-yl)piperidin-1-yl)-1-oxo-3-(4-(trifluoromethyl)phenyl)propan-2-yl)-3-(methylamino)cyclopentanecarboxamide | Method A | 0.76 | 585 |

TABLE 6-C-continued

| Example | Structure | Chemical Name | HPLC Gradient Method | HPLC Retention Time (min.) | MS (ESI): m/z (M + H)+ |
|---|---|---|---|---|---|
| 37 | 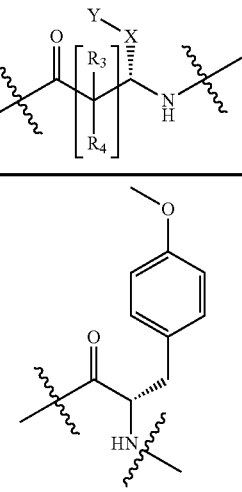 | (1S,3R)-N-((S)-1-(4-(3,3-dimethyl-2-oxoindolin-1-yl)piperidin-1-yl)-3-(4-methoxyphenyl)-1-oxopropan-2-yl)-3-(methylamino)cyclopentanecarboxamide | Method A | 0.7 | 547 |
| 38 | 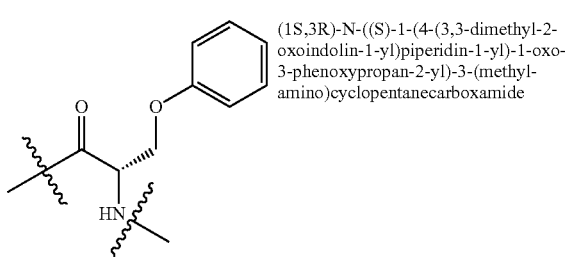 | (1S,3R)-N-((S)-1-(4-(3,3-dimethyl-2-oxoindolin-1-yl)piperidin-1-yl)-1-oxo-3-phenoxypropan-2-yl)-3-(methylamino)cyclopentanecarboxamide | Method A | 0.72 | 533 |

TABLE 6-D

| Example | Structure | Chemical Name | HPLC Gradient Method | HPLC Retention Time (min.) | MS (ESI): m/z (M + H)+ |
|---|---|---|---|---|---|
| 39 | 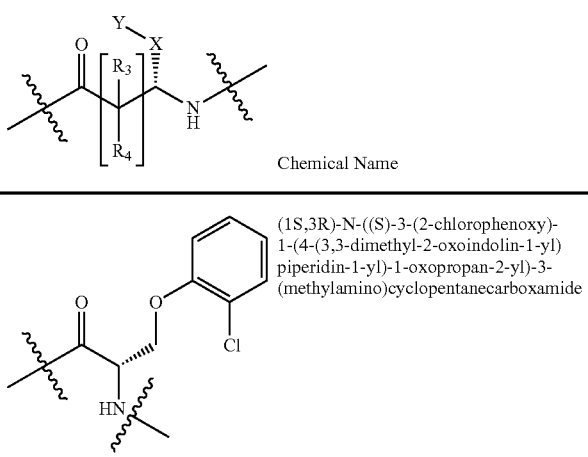 | (1S,3R)-N-((S)-3-(2-chlorophenoxy)-1-(4-(3,3-dimethyl-2-oxoindolin-1-yl)piperidin-1-yl)-1-oxopropan-2-yl)-3-(methylamino)cyclopentanecarboxamide | Method A | 0.74 | 567 |
| 40 | 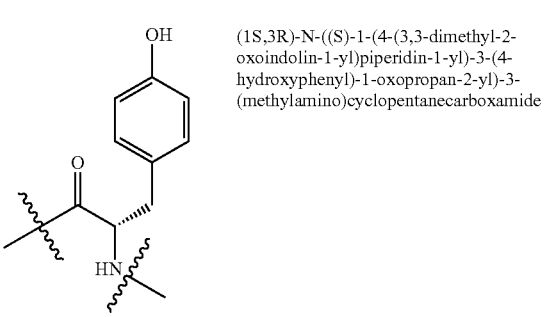 | (1S,3R)-N-((S)-1-(4-(3,3-dimethyl-2-oxoindolin-1-yl)piperidin-1-yl)-3-(4-hydroxyphenyl)-1-oxopropan-2-yl)-3-(methylamino)cyclopentanecarboxamide | Method A | 0.63 | 533 |

TABLE 6-D-continued

| Example | | Chemical Name | HPLC Gradient Method | HPLC Retention Time (min.) | MS (ESI): m/z (M + H)+ |
|---|---|---|---|---|---|
| 41 | | (1S,3R)-N-((2S,3S)-1-(4-(3,3-dimethyl-2-oxoindolin-1-yl)piperidin-1-yl)-3-methyl-1-oxopentan-2-yl)-3-(methylamino)cyclopentanecarboxamide | Method A | 0.69 | 483 |
| 42 | | (R)-N-((S)-1-(4-(3,3-dimethyl-2-oxoindolin-1-yl)piperidin-1-yl)-1-oxo-3-(pyridin-2-yl)propan-2-yl)piperidine-3-carboxamide | Method A | 0.62 | 504 |
| 43 | | (1S,3R)-N-((S)-4-(4-(3,3-dimethyl-2-oxoindolin-1-yl)piperidin-1-yl)-4-oxo-1-phenylbutan-2-yl)-3-(methylamino)cyclopentanecarboxamide | Method A | 0.71 | 531 |

Example 44

(R)—N—((S)-1-(4-(5-fluoro-3,3-dimethyl-2-oxoindolin-1-yl)piperidin-1-yl)-1-oxo-4-phenylbutan-2-yl)piperidine-3-carboxamide

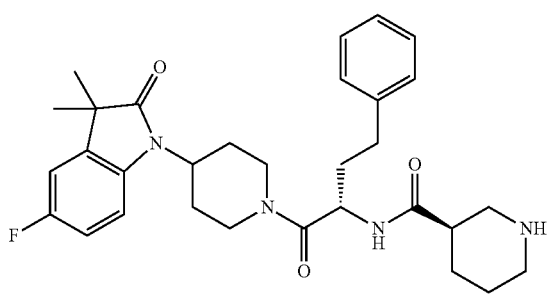 [SMILES: CC1(C)C(=O)N(C2CCN(C(=O)[C@H](CCc3ccccc3)NC(=O)[C@@H]3CCCNC3)CC2)c2ccc(F)cc21]

Step 1.

2-(2-bromo-5-fluorophenyl)-2-methylpropanoic acid

A mixture of methyl 2-(2-bromo-5-fluorophenyl)-2-methylpropanoate (0.529 g, 3.12 mmol, J. Am. Chem. Soc., 2008, 130, 15157-15166), potassium hydroxide (3.2 g, 57 mmol), water (10 mL) and ethanol (30 mL) was refluxed for 20 h.

The mixture was cooled to room temperature, and was concentrated to about 10 mL. The following mixture was adjusted to pH 4 with concentrated hydrochloric acid, and was extracted with dichloromethane (200 mL). The organic phase was washed with water and brine, dried over magnesium sulfate and concentrated in vacuo to give the title compound (0.510 g, 100%).

$^1$H NMR (CDCl$_3$) δ: 7.55-7.51 (1H, m), 7.18-7.13 (1H, m), 6.90-6.84 (1H, m), 1.67 (6H, s).

Step 2.

N-(1-benzylpiperidin-4-yl)-2-(2-bromo-5-fluorophenyl)-2-methylpropanamide

To a solution of 2-(2-bromo-5-fluorophenyl)-2-methylpropanoic acid (510 mg, 1.95 mmol, EXAMPLE 44, Step 1) in tetrahydrofuran (20 mL) were added triphosgene (197 mg, 0.66 mmol) and triethylamine (0.288 mL, 2.05 mmol). The mixture was stirred at room temperature for 30 min and was filtered. The filtrate was added drop-wise into a solution of 1-benzyl-4-aminopiperidine (372 mg, 1.95 mmol) and triethylamine (0.288 mL, 2.05 mmol) in tetrahydrofuran (20 mL). The mixture was stirred at room temperature for overnight.

Precipitates were filtered off, and the filtrate was concentrated. The residue was diluted with ethyl acetate. The organic layer was washed with 0.1 mol/L sodium hydroxide aqueous solution, water and brine, and was dried over sodium sulfate and concentrated. The residue was purified by silica gel column chromatography (20-100% ethyl acetate in hexane) to give the title compound (275 mg, 33%).

$^1$H NMR (CDCl$_3$) δ: 7.56-7.52 (1H, m), 7.32-7.19 (6H, m), 6.92-6.86 (1H, m), 4.94-4.91 (1H, m), 3.81-3.78 (1H, m), 3.45 (2H, s), 2.75-2.71 (2H, m), 2.12-2.04 (2H, m), 1.91-1.86 (2H, m), 1.61 (6H, s), 1.38-1.23 (2H, m).

MS (ESI) m/z: 433 (M+H)$^+$.

Step 3.

1-(1-benzylpiperidin-4-yl)-5-fluoro-3,3-dimethylindolin-2-one

A mixture of N-(1-benzylpiperidin-4-yl)-2-(2-bromo-5-fluorophenyl)-2-methylpropanamide (275 mg, 0.635 mmol, EXAMPLE 44, Step 2), palladium acetate (14 mg, 0.063 mmol), phenyl boronic acid (15 mg, 0.13 mmol), dicyclohexyl(2',4',6'-triisopropylbiphenyl-2-yl)phosphine (30 mg, 0.063 mmol), potassium carbonate (220 mg, 1.6 mmol) and t-butyl alcohol (15 mL) was refluxed under nitrogen atmosphere for 14 h. The mixture was cooled to room temperature, filtered, and concentrated under reduced pressure. The residue was purified by silica gel column chromatography (8-66% ethyl acetate in hexane) to give the title compound (171 mg, 76%).

$^1$H NMR (CDCl$_3$) δ: 7.35-7.26 (5H, m), 7.11-7.07 (1H, m), 6.94-6.89 (2H, m), 4.35-4.25 (1H, m), 3.56 (2H, s), 3.05-2.98 (2H, m), 2.50-2.34 (2H, m), 2.19-2.09 (2H, m), 1.70-1.63 (2H, m), 1.32 (6H, s).

MS (ESI) m/z: 353 (M+H)$^+$.

TLC Rf: 0.25 (ethyl acetate/hexane 1:2).

Step 4.

5-fluoro-3,3-dimethyl-1-(piperidin-4-yl)indolin-2-one

A mixture of 1-(1-benzylpiperidin-4-yl)-5-fluoro-3,3-dimethylindolin-2-one (171 mg, 0.485 mmol, EXAMPLE 44, Step 3), palladium hydroxide (20 wt % on carbon) (85 mg), formic acid (0.372 mL, 9.7 mmol) and ethanol (20 mL) was stirred at 50° C. for 1 h.

The mixture was cooled to room temperature, and filtered through Celite(registered trademark). The filtrate was concentrated under reduced pressure. To the residue were added 2 mol/L sodium hydroxide aqueous solution (1 mL) and water (15 mL). The aqueous mixture was extracted twice with ethyl acetate. Combined organic layers were washed with brine, dried over sodium sulfate, filtered, and concentrated under reduced pressure to give the title compound (124 mg, 86%) as a solid.

$^1$H NMR (CDCl$_3$) δ: 7.12-7.07 (1H, m), 6.98-6.88 (2H, m), 4.40-4.30 (1H, m), 3.28-3.23 (2H, m), 2.80-2.72 (2H, m), 2.35-2.29 (2H, m), 1.73-1.65 (4H, m), 1.35 (6H, s).

MS (ESI) m/z: 263 (M+H)$^+$.

Step 5.

(S)-tert-butyl 1-(4-(5-fluoro-3,3-dimethyl-2-oxoindolin-1-yl)piperidin-1-yl)-1-oxo-4-phenylbutan-2-ylcarbamate The title compound was prepared according to the procedure described in the Step 3 of the EXAMPLE 1 using 5-fluoro-3,3-dimethyl-1-(piperidin-4-yl)indolin-2-one (EXAMPLE 44, Step 4) instead of 3,3-dimethyl-1-(piperidin-4-yl)indolin-2-one hydrochloride.

$^1$H NMR (CDCl$_3$) δ: 7.32-7.19 (5H, m), 6.95-6.73 (3H, m), 5.50-5.37 (1H, m), 4.80-4.32 (3H, m), 3.78-3.65 (1H, m), 3.05-2.90 (1H, m), 2.73-2.63 (3H, m), 2.28-2.17 (2H, m), 1.96-1.67 (4H, m), 1.49-1.46 (9H, pseudo d), 1.34-1.33 (6H, pseudo d).

MS (ESI) m/z: 524 (M+H)$^+$.

Step 6.

(S)-1-(1-(2-amino-4-phenylbutanoyl)piperidin-4-yl)-5-fluoro-3,3-dimethylindolin-2-one The title compound was prepared according to the procedure described in the Step 4 of the EXAMPLE 1 using 1-(4-(5-fluoro-3,3-dimethyl-2-oxoindolin-1-yl)piperidin-1-yl)-1)-1-oxo-4-phenylbutan-2-ylcarbamate (EXAMPLE 44, Step 5) instead of 1-(4-(3,3-dimethyl-2-oxoindolin-1-yl)piperidin-1-yl)-1-oxo-4-phenylbutan-2-ylcarbamate.

MS (ESI) m/z: 424 (M+H)$^+$.

Step 7.

(R)—N—((S)-1-(4-(5-fluoro-3,3-dimethyl-2-oxoindolin-1-yl)piperidin-1-yl)-1-oxo-4-phenylbutan-2-yl)piperidine-3-carboxamide The title compound was prepared according to the procedure described in the Step 5 of the EXAMPLE 1 using 1-(4-(5-fluoro-3,3-dimethyl-2-oxoindolin-1-yl)piperidin-1-yl)-1-oxo-4-phenylbutan-2-ylcarbamate (EXAMPLE 44, Step 6) instead of 1-(4-(3,3-dimethyl-2-oxoindolin-1-yl)piperidin-1-yl)-1-oxo-4-phenylbutan-2-ylcarbamate.

MS (ESI) m/z: 535 (M+H)$^+$.

HPLC retention time: 0.73 min (Method A).

Example 45-46

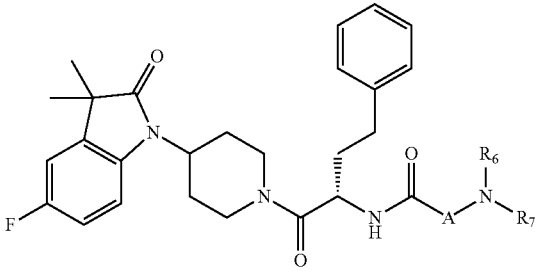

{Chem. 28}

The following examples, EXAMPLE 45-46, were prepared according to the procedure similar to that described in Step 7 of the EXAMPLE 44, using the appropriate precursor instead of (R)-1-(tert-butoxycarbonyl)piperidine-3-carboxylic acid.

TABLE 7

| Example | Structure | Chemical Name | HPLC Gradient Method | HPLC Retention Time (min.) | MS (ESI): m/z (M + H)+ |
|---|---|---|---|---|---|
| 45 |  | (1S,3R)-N-((S)-1-(4-(5-fluoro-3,3-dimethyl-2-oxoindolin-1-yl)piperidin-1-yl)-1-oxo-4-phenylbutan-2-yl)-3-(methylamino)cyclopentane-carboxamide | Method A | 0.75 | 549 |

TABLE 7-continued

| Example | | Chemical Name | HPLC Gradient Method | HPLC Retention Time (min.) | MS (ESI): m/z (M + H)+ |
|---|---|---|---|---|---|
| 46 | | (S)-N-(1-(4-(5-fluoro-3,3-dimethyl-2-oxoindolin-1-yl)piperidin-1-yl)-1-oxo-4-phenylbutan-2-yl)-3-methyl-3-(methylamino)butanamide | Method A | 0.75 | 537 |

Example 47

(S)—N—((S)-1-(4-(3,3-dimethyl-2-oxoindolin-1-yl)piperidin-1-yl)-1-oxo-4-phenylbutan-2-yl)-3-(methylamino)pyrrolidine-1-carboxamide

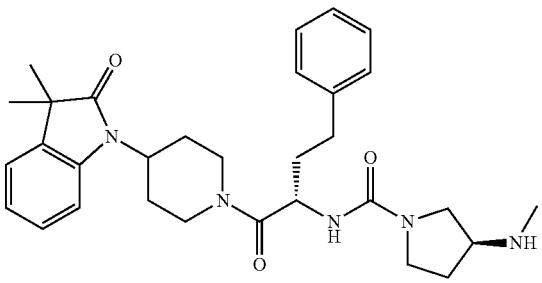 [SMILES: CN[C@H]1CCN(C(=O)N[C@@H](CCc2ccccc2)C(=O)N2CCC(N3C(=O)C(C)(C)c4ccccc43)CC2)C1]

(S)—N—((S)-1-(4-(3,3-dimethyl-2-oxoindolin-1-yl)piperidin-1-yl)-1-oxo-4-phenylbutan-2-yl)-3-(dimethylamino)pyrrolidine-1-carboxamide To a solution of 4-nitrophenyl chloroformate (15 mg, 0.075 mmol) in dichloromethane (0.5 mL) was added a mixture of (S)-1-(1-(2-amino-4-phenylbutanoyl)piperidin-4-yl)-3,3-dimethylindolin-2-one hydrochloride (30 mg, 0.068 mmol) and triethylamine (20 microL, 0.143 mmol) in dichloromethane (1 mL) at room temperature. After stirring for 5 min, (S)-tert-butyl methyl(pyrrolidin-3-yl)carbamate (27 mg, 0.136 mmol, Bioorg. Med. Chem. Lett., 2006, 16, 4922-4930) and triethylamine (19 microL, 0.136 mmol) in dichloromethane (1 mL) were added to the mixture. The whole mixture was stirred at room temperature for 20 min., then concentrated in vacuo.

To the residue was added trifluoroacetic acid (1 mL) and the resulting solution was stirred for 20 min. Then the mixture was concentrated in vacuo. The residue was diluted with methanol and applied onto a strong cation exchange cartridge (BondElute(registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo. The residue was purified by prep-LC-MS to give the title compound (13.6 mg, 38%).

MS (ESI) m/z: 532 (M+H)+.
HPLC retention time: 0.72 min. (Method A).

Example 47
Alternative Method
Step 1.

tert-butyl (S)-1-((S)-1-(4-(3,3-dimethyl-2-oxoindolin-1-yl)piperidin-1-yl)-1-oxo-4-phenylbutan-2-ylcarbamoyl)pyrrolidin-3-yl(methyl)carbamate To a mixture of 4-nitrophenyl chloroformate (227 mg, 1.13 mmol) in dichloromethane (3 mL) was added a mixture of (S)-1-(1-(2-amino-4-phenylbutanoyl)piperidin-4-yl)-3,3-dimethylindolin-2-one (500 mg, 1.13 mmol) and triethylamine (0.32 mL, 2.26 mmol) in dichloromethane (6 mL), and the reaction mixture was stirred for 30 min at room temperature.

Then, to the mixture was added a mixture of (S)-tert-butyl methyl(pyrrolidin-3-yl)carbamate (239 mg, 1.13 mmol, Bioorg. Med. Chem. Lett., 2006, 16, 4922-4930) and triethylamine (0.32 mL, 2.26 mmol) in dichloromethane (6 mL), and the resulting solution was stirred for 20 min at room temperature. The mixture was diluted with saturated sodium hydrogen carbonate aqueous solution and extracted with ethyl acetate. The organic layer was dried over sodium sulfate, filtered and concentrated under reduced pressure. The residual oil was purified by silica gel column chromatography to give the title compound (475 mg, 67%) as a colorless oil.

$^1$H NMR (CDCl$_3$) δ: 7.34-7.12 (7H, m), 7.09-6.83 (2H, m), 5.29-5.20 (1H, m), 4.98-4.68 (2H, m), 4.59-4.27 (1H, m), 3.85-3.71 (1H, m), 3.68-3.50 (2H, m), 3.39-3.17 (2H, m), 3.12-2.92 (1H, m), 2.87-2.58 (7H, m), 2.46-2.18 (2H, m), 2.18-1.60 (6H, m), 1.48 (9H, s), 1.35 (6H, br s).
MS (ESI) m/z: 632 (M+H)+, 630 (M−H)−.

Step 2.

(S)—N—((S)-1-(4-(3,3-dimethyl-2-oxoindolin-1-yl)piperidin-1-yl)-1-oxo-4-phenylbutan-2-yl)-3-(methylamino)pyrrolidine-1-carboxamide A mixture of tert-butyl (S)-1-((S)-1-(4-(3,3-dimethyl-2-oxoindolin-1-yl)piperidin-1-yl)-1-oxo-4-phenylbutan-2-ylcarbamoyl)pyrrolidin-3-yl(methyl)carbamate (267 mg, 0.42 mmol, EXAMPLE 47: Alternative Method, Step 1) in dichloromethane-trifluoroacetic acid (1:1, 6 mL) was stirred at room temperature for 1 h. The mixture was concentrated, diluted with dichloromethane, and washed with saturated sodium hydrogen carbonate aqueous solution. The organic layer was dried over sodium sulfate, filtered and concentrated under reduced pressure. The residual oil was purified by preparative HPLC (32-96% methanol in 0.01% ammonia aqueous solution) and by amino gel column chromatography to give the title compound (209 mg, 93%) as a colorless oil.

$^1$H NMR (CDCl$_3$) δ: 7.34-7.11 (7H, m), 7.10-6.82 (2H, m), 5.29-5.18 (1H, m), 5.00-4.88 (1H, m), 4.80-4.72 (1H, m), 4.59-4.27 (1H, m), 3.85-3.74 (1H, m), 3.66-3.45 (2H, m), 3.45-3.10 (3H, m), 3.10-2.94 (1H, m), 2.83-2.57 (3H, m), 2.46 (3H, br s), 2.45-1.55 (9H, m), 1.34 (6H, br s).
MS (ESI) m/z: 532 (M+H)+, 530 (M−H)−.

Example 48-66

The following examples, 48-66, were prepared according to the procedure similar to that described in the EXAMPLE 47, using the appropriate precursors as indicated in the table, instead of (S)-tert-butyl methyl(pyrrolidin-3-yl)carbamate.

{Chem. 30}

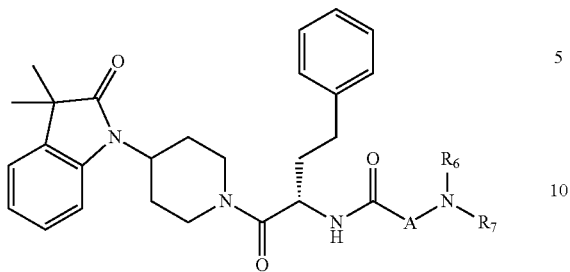

TABLE 8-A

| Example | $\begin{array}{c}\text{O}\\\text{~~}\text{C-N}\\\text{A}\end{array}$ R6/R7 structure | Chemical Name | HPLC Gradient Method | HPLC Retention Time (min.) | MS (ESI): m/z (M + H)+ |
|---|---|---|---|---|---|
| 48 | [structure: C(=O)NH-CH2-(S)-pyrrolidin-2-yl] | 1-((S)-1-(4-(3,3-dimethyl-2-oxo-indolin-1-yl)piperidin-1-yl)-1-oxo-4-phenylbutan-2-yl)-3-((S)-pyrrolidin-2-ylmethyl)urea | Method A | 0.73 | 532 |
| 49 | [structure: C(=O)NH-(R)-piperidin-3-yl] | 1-((S)-1-(4-(3,3-dimethyl-2-oxo-indolin-1-yl)piperidin-1-yl)-1-oxo-4-phenylbutan-2-yl)-3-((R)-piperidin-3-yl)urea | Method A | 0.73 | 532 |
| 50 | [structure: C(=O)N(CH3)-CH2-(S)-pyrrolidin-2-yl] | 3-((S)-1-(4-(3,3-dimethyl-2-oxo-indolin-1-yl)piperidin-1-yl)-1-oxo-4-phenylbutan-2-yl)-1-methyl-1-((S)-pyrrolidin-2-ylmethyl)urea | Method B | 2.19 | 546 |
| 51 | [structure: C(=O)NH-CH2-(R)-pyrrolidin-2-yl] | 1-((S)-1-(4-(3,3-dimethyl-2-oxo-indolin-1-yl)piperidin-1-yl)-1-oxo-4-phenylbutan-2-yl)-3-((R)-pyrrolidin-2-ylmethyl)urea | Method A | 0.74 | 532 |
| 52 | [structure: C(=O)NH-(R)-pyrrolidin-3-yl] | 1-((S)-1-(4-(3,3-dimethyl-2-oxo-indolin-1-yl)piperidin-1-yl)-1-oxo-4-phenylbutan-2-yl)-3-((R)-pyrrolidin-3-yl)urea | Method A | 0.71 | 518 |
| 53 | [structure: C(=O)NH-CH2-(R)-pyrrolidin-3-yl] | 1-((S)-1-(4-(3,3-dimethyl-2-oxo-indolin-1-yl)piperidin-1-yl)-1-oxo-4-phenylbutan-2-yl)-3-((R)-pyrrolidin-3-ylmethyl)urea | Method A | 0.71 | 532 |
| 54 | [structure: C(=O)-N(3-methylpiperazin-1-yl)] | (R)-N-((S)-1-(4-(3,3-dimethyl-2-oxoindolin-1-yl)piperidin-1-yl)-1-oxo-4-phenylbutan-2-yl)-3-methyl-piperazine-1-carboxamide | Method B | 2.19 | 532 |

TABLE 8-B

| Example | Chemical Name | HPLC Gradient Method | HPLC Retention Time (min.) | MS (ESI): m/z (M + H)+ |
|---|---|---|---|---|
| 55 | (S)-1-(1-(4-(3,3-dimethyl-2-oxo-indolin-1-yl)piperidin-1-yl)-1-oxo-4-phenylbutan-2-yl)-3-(4-ethylpiperidin-4-yl)urea | Method A | 0.75 | 560 |
| 56 | (S)-1-(1-(4-(3,3-dimethyl-2-oxo-indolin-1-yl)piperidin-1-yl)-1-oxo-4-phenylbutan-2-yl)-3-(4-methyl-piperidin-4-yl)urea | Method A | 0.73 | 546 |
| 57 | 1-((S)-1-(4-(3,3-dimethyl-2-oxo-indolin-1-yl)piperidin-1-yl)-1-oxo-4-phenylbutan-2-yl)-3-((S)-pyrrolidin-3-yl)urea | Method A | 0.71 | 518 |
| 58 | (S)-1-(azetidin-3-yl)-3-(1-(4-(3,3-dimethyl-2-oxoindolin-1-yl)piperidin-1-yl)-1-oxo-4-phenyl-butan-2-yl)urea | Method A | 0.71 | 504 |
| 59 | 3-((S)-1-(4-(3,3-dimethyl-2-oxo-indolin-1-yl)piperidin-1-yl)-1-oxo-4-phenylbutan-2-yl)-1-methyl-1-((R)-pyrrolidin-3-yl)urea | Method A | 0.73 | 532 |
| 60 | 1-((S)-1-(4-(3,3-dimethyl-2-oxo-indolin-1-yl)piperidin-1-yl)-1-oxo-4-phenylbutan-2-yl)-3-((S)-piperidin-2-ylmethyl)urea | Method C | 1.72 | 546 |
| 61 | 1-((S)-1-(4-(3,3-dimethyl-2-oxo-indolin-1-yl)piperidin-1-yl)-1-oxo-4-phenylbutan-2-yl)-3-((R)-piperidin-3-ylmethyl)urea | Method C | 1.64 | 5.46 |

TABLE 8-C

| Example | Chemical Name | HPLC Gradient Method | HPLC Retention Time (min.) | MS (ESI): m/z (M + H)+ |
|---|---|---|---|---|
| 62 | (S)-1-(2-amino-2-methylpropyl)-3-(1-(4-(3,3-dimethyl-2-oxoindolin-1-yl)piperidin-1-yl)-1-oxo-4-phenyl-butan-2-yl)urea | Method A | 0.73 | 520 |

TABLE 8-C-continued

| Example | Chemical Name | HPLC Gradient Method | HPLC Retention Time (min.) | MS (ESI): m/z (M + H)+ |
|---|---|---|---|---|
| 63 | (S)-3-(cyclopropyl(methyl)amino)-N-((S)-1-(4-(3,3-dimethyl-2-oxo-indolin-1-yl)piperidin-1-yl)-1-oxo-4-phenylbutan-2-yl)pyrrolidine-1-carboxamide | Method A | 0.83 | 572 |
| 64 | (S)-1-(1-(4-(3,3-dimethyl-2-oxo-indolin-1-yl)piperidin-1-yl)-1-oxo-4-phenylbutan-2-yl)-3-(2-(pyrrolidin-1-yl)ethyl)urea | Method A | 0.74 | 546 |
| 65 | (S)-1-(1-(4-(3,3-dimethyl-2-oxo-indolin-1-yl)piperidin-1-yl)-1-oxo-4-phenylbutan-2-yl)-3-(2-(dimethyl-amino)ethyl)urea | Method A | 0.72 | 520 |
| 66 | (S)-N-(1-(4-(3,3-dimethyl-2-oxo-indolin-1-yl)piperidin-1-yl)-1-oxo-4-phenylbutan-2-yl)-3,3-dimethyl-piperazine-1-carboxamide | Method A | 0.73 | 546 |

Example 67

(S)—N—((S)-1-(4-(3,3-dimethyl-2-oxoindolin-1-yl)piperidin-1-yl)-1-oxo-4-phenylbutan-2-yl)-3-(dimethylamino)pyrrolidine-1-carboxamide

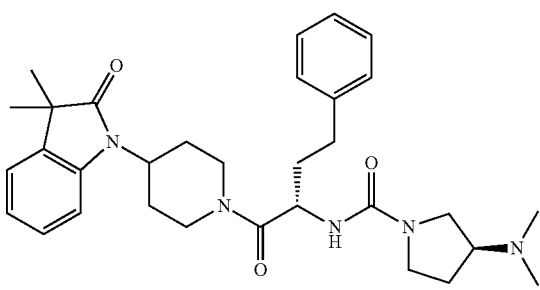 [SMILES: CN(C)[C@H]1CCN(C(=O)N[C@@H](CCc2ccccc2)C(=O)N2CCC(N3C(=O)C(C)(C)c4ccccc43)CC2)C1]

Step 1.

(S)—N—((S)-1-(4-(3,3-dimethyl-2-oxoindolin-1-yl)piperidin-1-yl)-1-oxo-4-phenylbutan-2-yl)-3-(dimethylamino)pyrolidine-1-carboxamide To a solution of 4-nitrophenyl chloroformate (15 mg, 0.075 mmol) in dichloromethane (0.5 mL) was added a mixture of (S)-1-(1-(2-amino-4-phenylbutanoyl)piperidin-4-yl)-3,3-dimethylindolin-2-one hydrochloride (30 mg, 0.068 mmol) and triethylamine (20 microL, 0.143 mmol) in dichloromethane (1 mL) at room temperature. After stirring for 5 min, (S)-tert-butyl methyl(pyrrolidin-3-yl)carbamate (27 mg, 0.136 mmol, Bioorg. Med. Chem. Lett., 2006, 16, 4922-4930) and triethylamine (19 microL, 0.136 mmol) in dichloromethane (1 mL) to the mixture. The whole mixture was stirred at room temperature for 20 min. The mixture was concentrated. To the residue was added trifluoroacetic acid (1 mL) and the resulting solution was stirred for 20 min. Then the mixture was concentrated in vacuo. The residue was diluted with methanol and applied onto a strong cation exchange cartridge (BondElute(registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo.

The residue was dissolved in methanol (2 mL). To the solution was added paraformaldehyde (20 mg, 0.68 mmol) and sodium triacetoxyborohydride (72 mg, 0.34 mmol) at room temperature. After 2 h, 2 drops of acetic acid was added to the mixture, followed by triacetoxyborohydride (72 mg, 0.34 mmol). After 1 h, the mixture was concentrated and the residue was basified by aq. sodium bicarbonate and extracted with ethyl acetate (2 mL×3). The combined organic layers were filtered through magnesium sulfate column and the filtrate was concentrated in vacuo. The crude product was purified by preparative LC-MS to give the title compound (10.4 mg, 28%).

MS (ESI) m/z: 546 (M+H)+.

HPLC retention time: 0.75 min. (Method A).

Example 68-69

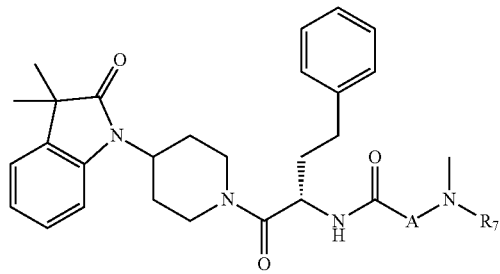

The following examples, EXAMPLE 68-69, were prepared according to the procedure similar to that described in the EXAMPLE 67, using the appropriate precursor instead of (S)-tert-butyl methyl(pyrrolidin-3-yl)carbamate.

Example 70

(S)—N—((S)-1-(4-(5-fluoro-3,3-dimethyl-2-oxoindolin-1-yl)piperidin-1-yl)-1-oxo-4-phenylbutan-2-yl)-3-(methylamino)pyrrolidine-1-carboxamide

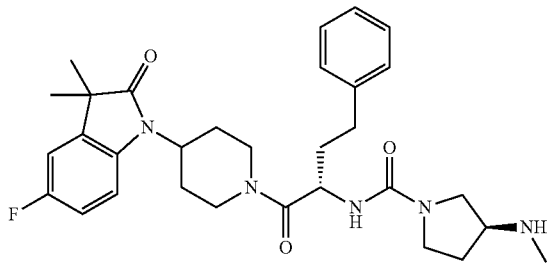 [SMILES: CN[C@H]1CCN(C(=O)N[C@@H](CCc2ccccc2)C(=O)N2CCC(N3C(=O)C(C)(C)c4cc(F)ccc43)CC2)C1]

The title compound was prepared according to the procedure described in the Step 1 of the EXAMPLE 47 using (S)-1-(1-(2-amino-4-phenylbutanoyl)piperidin-4-yl)-5-fluoro-3,3-dimethylindolin-2-one (EXAMPLE 44, Step 6) instead of (S)-1-(1-(2-amino-4-phenylbutanoyl)piperidin-4-yl)-3,3-dimethylindolin-2-one hydrochloride.

MS (ESI) m/z: 550 (M+H)+.

HPLC retention time: 0.73 min (Method A).

Example 71-72

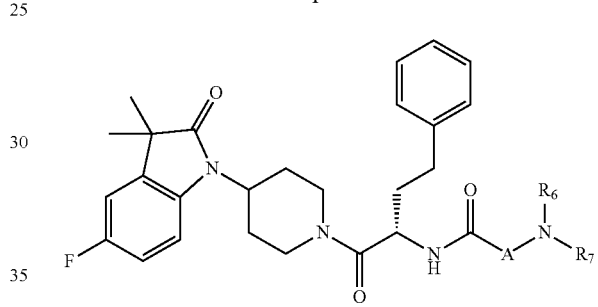

The following examples, EXAMPLE 71-72, were prepared according to the procedure similar to that described in the Step 1 of the EXAMPLE 67, using (S)-1-(1-(2-amino-4-phenylbutanoyl)piperidin-4-yl)-5-fluoro-3,3-dimethylindolin-2-one (EXAMPLE 44, Step 6) and the appropriate amine precursor instead of (S)-1-(1-(2-amino-4-phenylbutanoyl)piperidin-4-yl)-3,3-dimethylindolin-2-one hydrochloride and (S)-tert-butyl methyl(pyrrolidin-3-yl)carbamate, respectively.

TABLE 9

| Example | | Chemical Name | HPLC Gradient Method | HPLC Retention Time (min.) | MS (ESI): m/z (M + H)+ |
|---|---|---|---|---|---|
| 68 | | 1-((S)-1-(4-(3,3-dimethyl-2-oxoindolin-1-yl)piperidin-1-yl)-1-oxo-4-phenylbutan-2-yl)-3-(((S)-1-methylpyrrolidin-2-yl)methyl)urea | Method B | 2.19 | 546 |
| 69 | | (S)-1-(1-(4-(3,3-dimethyl-2-oxoindolin-1-yl)piperidin-1-yl)-1-oxo-4-phenylbutan-2-yl)-3-(1,4-dimethylpiperidin-4-yl)urea | Method B | 2.19 | 560 |

TABLE 10

| Example | Chemical Name | HPLC Gradient Method | HPLC Retention Time (min.) | MS (ESI): m/z (M + H)+ |
|---|---|---|---|---|
| 71 | 1-((S)-1-(4-(5-fluoro-3,3-dimethyl-2-oxoindolin-1-yl)piperldin-1-yl)-1-oxo-4-phenylbutan-2-yl)-3-((S)-pyrrolidin-2-ylmethyl)urea | Method A | 0.75 | 550 |
| 72 | (S)-1-(1-4-(5-fluoro-3,3-dimethyl-2-oxoindolin-1-yl)piperidin-1-yl)-1-oxo-4-phenylbutan-2-yl)-3-(4-methylpiperidin-4-yl)urea | Method A | 0.74 | 564 |

Example 73

(R)—N—((S)-1-(4-(3,3-dimethyl-2-oxoindolin-1-yl)piperidin-1-yl)-1-oxo-4-phenylbutan-2-yl)-N-methylpiperidine-3-carboxamide

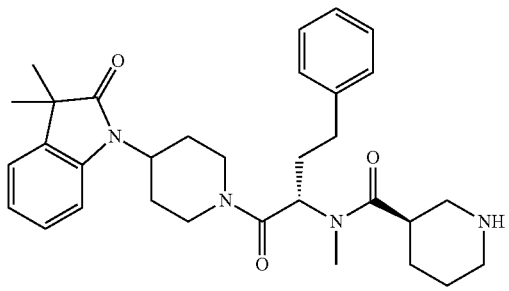 [SMILES: CN(C(=O)[C@@H]1CCCNC1)[C@@H](CCc1ccccc1)C(=O)N1CCC(N2C(=O)C(C)(C)c3ccccc32)CC1]

Step 1.

(S)—N-(1-(4-(3,3-dimethyl-2-oxoindolin-1-yl)piperidin-1-yl)-1-oxo-4-phenylbutan-2-yl)-2-nitro benzenesulfonamide To a solution of (S)-1-(1-(2-amino-4-phenylbutanoyl)piperidin-4-yl)-3,3-dimethylindolin-2-one hydrochloride (1.00 g, 2.26 mmol, EXAMPLE 1, Step 4) in dichloromethane (10 mL) was added triethylamine (954 microL, 6.79 mmol) and 2-nitrobenzenesulfonyl chloride (501 mg, 2.26 mmol) at 0° C. After stirring for 20 min at room temperature, water and ethyl acetate were added to the mixture. The organic layer was washed with sodium hydrogen carbonate aqueous solution, 1 mol/L hydrochloric acid and brine, dried over sodium sulfate and concentrated. The crude product was purified by silica gel column chromatography (hexane/ethyl acetate, gradient) to give the title compound (1.26 g, 94%) as an amorphous solid.

$^1$H NMR (CDCl$_3$) δ: 8.20-7.62 (m, 4H), 7.39-7.10 (m, 7H), 6.84-6.78 (m, 1H), 6.66-6.48 (m, 1H), 4.56-3.97 (m, 3H), 3.50-3.30 (m, 1H), 3.00-2.73 (m, 3H), 2.56-1.80 (m, 8H), 1.46-1.31 (m, 6H).

Step 2.

(S)—N-(1-(4-(3,3-dimethyl-2-oxoindolin-1-yl)piperidin-1-yl)-1-oxo-4-phenylbutan-2-yl)-N-methyl-2-nitrobenzenesulfonamide To a mixture of (S)—N-(1-(4-(3,3-dimethyl-2-oxoindolin-1-yl)piperidin-1-yl)-1-oxo-4-phenylbutan-2-yl)-2-nitrobenzenesulfonamide (1.26 g, 2.13 mmol, EXAMPLE 73, Step 1), methanol (519 microL, 12.8 mmol), triphenylphosphine (1.12 g, 4.27 mmol) in tetrahydrofuran (10 mL) was added diethyl azodicarboxylate (2.2 mol/L toluene solution, 3.88 mL, 8.53 mmol) at room temperature. After 3 h, the mixture was concentrated and the residue was purified by silica gel column chromatography (hexane/ethyl acetate, gradient) to give a mixture of the title compound and triphenylphosphineoxide (3.30 g).

MS (ESI) m/z: 605 (M+H)$^+$.

Step 3.

(S)-3,3-dimethyl-1-(1-(2-(methylamino)-4-phenylbutanoyl)piperidin-4-yl)indolin-2-one To a solution of (S)—N-(1-(4-(3,3-dimethyl-2-oxoindolin-1-yl)piperidin-1-yl)-1-oxo-4-phenylbutan-2-yl)-N-methyl-2-nitrobenzenesulfonamide (3.30 g, with triphenylphosphineoxide as impurity, EXAMPLE 73, Step 2) in dimethyl formamide (10 mL) were added mercaptoacetic acid (491 mg, 5.33 mmol) and lithium hydroxide monohydrate (447 mg, 10.7 mmol) at room temperature. After stirring for 16 h, the mixture was diluted with ethyl acetate and saturated sodium hydrogen carbonate aqueous solution. The organic layer was washed with saturated sodium hydrogen carbonate aqueous solution and brine, dried over sodium sulfate and concentrated in vacuo. The residue was diluted with dichloromethane (10 mL) and to the solution was added hydrogen chloride in methanol. Then the mixture was concentrated. The residue was diluted with methanol, and mixed with strong cation exchange gel (BondeSil(registered trademark) SCX, 40 g, Varian Inc.). The gel was filtered and washed with 1 mol/L ammonia in methanol, and the solution was concentrated to give the title compound (636 mg, 71%).

MS (ESI) m/z: 420 (M+H)$^+$.

$^1$H NMR (CDCl$_3$) δ: 7.33-7.12 (m, 7H), 7.09-7.00 (m, 1H), 6.93-6.85 (m, 1H), 4.94-4.79 (m, 1H), 4.49-4.31 (m, 1H), 3.68-3.51 (m, 1H), 3.43-3.27 (m, 1H), 3.07-2.55 (m, 4H), 2.55-2.12 (m, 5H), 1.94-1.51 (m, 5H), 1.40-1.32 (m, 6H).

Step 4.

(R)—N—((S)-1-(4-(3,3-dimethyl-2-oxoindolin-1-yl)piperidin-1-yl)-1-oxo-4-phenylbutan-2-yl)-N-methylpiperidine-3-carboxamide To a solution of (S)-1-(1-(2-amino-4-phenylbutanoyl)piperidin-4-yl)-3,3-dimethylindolin-2-one hydrochloride (44 mg, 0.1 mmol, EXAMPLE 73, Step 3) in 3.75% triethylamine/N,N-dimethylacetamide (1.5 mL) were added (S)-1-

(tert-butoxycarbonyl)piperidine-2-carboxylic acid (25.2 mg, 0.110 mmol) and 2-(1H-benzotriazole-1-yl)-1,1,3,3-tetramethyluronium hexafluorophosphate (57 mg, 0.150 mmol), and the mixture was stirred at 60° C. for 6 h. Then the mixture was cooled to room temperature and stirred for further 13 h. Volatiles were removed in vacuo.

The residue was dissolved in 1,2-dichloroethane (1 mL), and trifluoroacetic acid (1 mL) was added. The mixture was stirred at room temperature for 2 h. Then the mixture was concentrated in vacuo. The residue was diluted with methanol and applied onto a strong cation exchange cartridge (Bond-Elute(registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo. The residue was purified by preparative LC-MS to give the title compound (4.3 mg, 8%).

MS (ESI) m/z: 531 (M+H)+.

HPLC retention time: 0.74 min. (Method A).

Example 74

1-((S)-1-(4-(3,3-dimethyl-2-oxoindolin-1-yl)piperidin-1-yl)-1-oxo-4-phenylbutan-2-yl)-1-methyl-3-((R)-piperidin-3-yl)urea

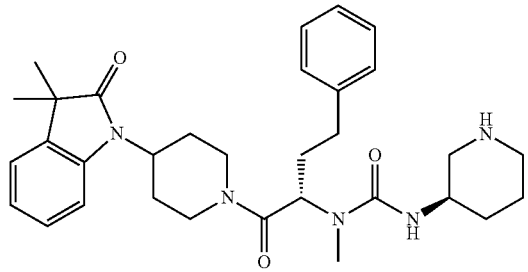 [SMILES: CN(C(=O)N[C@@H]1CCCNC1)[C@@H](CCc1ccccc1)C(=O)N1CCC(N2C(=O)C(C)(C)c3ccccc32)CC1]

Step 1.

1-((S)-1-(4-(3,3-dimethyl-2-oxoindolin-1-yl)piperidin-1-yl)-1-oxo-4-phenylbutan-2-yl)-2-methyl-3-yl)urea To a solution of 4-nitrophenyl chloroformate (14 mg, 0.072 mmol) in dichloromethane (1 mL) was added a mixture of (R)-tert-butyl 3-aminopiperidine-1-carboxylate (14 mg, 0.072 mmol) and triethylamine (10 microL, 0.072 mmol) in dichloromethane (1 mL) at room temperature. After stirring for 5 min, the solution was added to a solution of (S)-3,3-dimethyl-1-(1-(2-(methylamino)-4-phenylbutanoyl)piperidin-4-yl)indolin-2-one (20 mg, 0.048 mmol, EXAMPLE 73, Step 3) and triethylamine (13 microL, 0.095 mmol) in dichloromethane (1 mL). The whole mixture was stirred at room temperature for 3 h. The reaction mixture was concentrated. To the residue was added trifluoroacetic acid (1 mL), and the mixture was stirred for 15 min. Then the mixture was concentrated in vacuo. The residue was diluted with methanol and applied onto a strong cation exchange cartridge (Bond-Elute(registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo. The residue was purified by prep-LC-MS to give the title compound (2.3 mg, 9%).

MS (ESI) m/z: 546 (M+H)+.

HPLC retention time: 0.73 min. (Method A).

Example 75-81

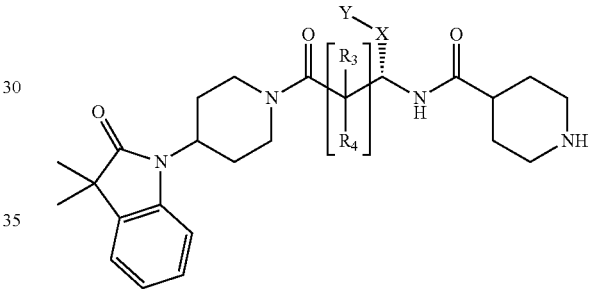

The following examples, EXAMPLE 75-81, were prepared according to the procedure described in the Step 2 through 3 of the EXAMPLE 21, using the appropriate amino acid precursor and 1-(tert-butoxycarbonyl)piperidine-4-carboxylic acid instead of (S)-2-(tert-butoxycarbonylamino)-3-(4-chlorophenyl)propanoic acid and (1S,3R)-3-(tert-butoxycarbonyl(methyl)amino)cyclopentanecarboxylic acid, respectively.

TABLE 11-A

| Example | Structure | Chemical Name | HPLC Gradient Method | HPLC Retention Time (min.) | MS (ESI): m/z (M + H)+ |
|---|---|---|---|---|---|
| 75 |  | (S)-N-(1-(4-(3,3-dimethyl-2-oxoindolin-1-yl)piperidin-1-yl)-1-oxo-3-phenylpropan-2-yl)piperidine-4-carboxamide | Method C | 1.44 | 501 |

TABLE 11-A-continued

| Example | Structure | Chemical Name | HPLC Gradient Method | HPLC Retention Time (min.) | MS (ESI): m/z (M + H)+ |
|---|---|---|---|---|---|
| 76 | 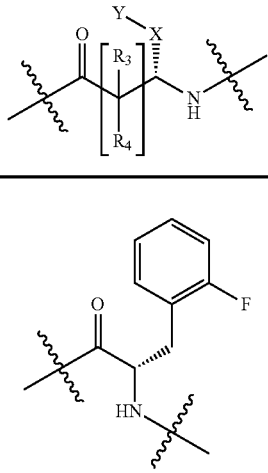 | (S)-N-(1-(4-(3,3-dimethyl-2-oxoindolin-1-yl)piperidin-1-yl)-3-(2-fluorophenyl)-1-oxopropan-2-yl)piperidine-4-carboxamide | Method C | 1.45 | 519 |
| 77 | 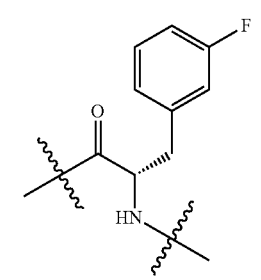 [SMILES: *N[C@@H](Cc1cccc(F)c1)C(*)=O] | (S)-N-(1-(4-(3,3-dimethyl-2-oxoindolin-1-yl)piperidin-1-yl)-3-(3-fluorophenyl)-1-oxopropan-2-yl)piperidine-4-carboxamide | Method C | 1.46 | 519 |
| 78 | 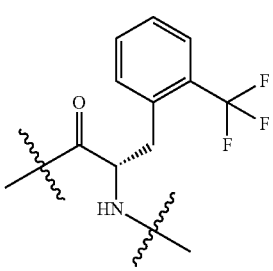 [SMILES: *N[C@@H](Cc1ccccc1C(F)(F)F)C(*)=O] | (S)-N-(1-(4-(3,3-dimethyl-2-oxoindolin-1-yl)piperidin-1-yl)-1-oxo-3-(2-(trifluoromethyl)phenyl)propan-2-yl)piperidine-4-carboxamide | Method C | 1.55 | 569 |
| 79 | 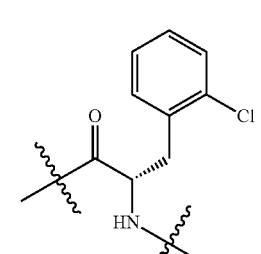 | (S)-N-(3-(2-chlorophenyl)-1-(4-(3,3-dimethyl-2-oxoindolin-1-yl)piperidin-1-yl)-1-oxopropan-2-yl)piperidine-4-carboxamide | Method C | 1.50 | 535 |
| 80 | 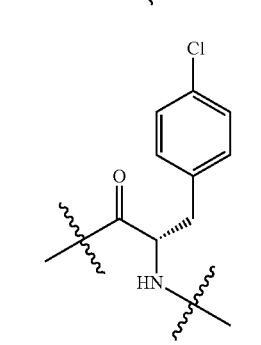 | (S)-N-(3-4-chlorophenyl)-1-(4-(3,3-dimethyl-2-oxoindolin-1-yl)piperidin-1-yl)-1-oxopropan-2-yl)piperidine-4-carboxamide | Method C | 1.54 | 535 |

TABLE 11-B

| Example | Structure | Chemical Name | HPLC Gradient Method | HPLC Retention Time (min.) | MS (ESI): m/z (M + H)+ |
|---|---|---|---|---|---|
| 81 | | (S)-N-(1-(4-(3,3-dimethyl-2-oxoindolin-1-yl)piperidin-1-yl)-3,3-dimethyl-1-oxo-butan-2-yl)piperidine-4-carboxamide | Method C | 1.41 | 467 |

Example 82-88

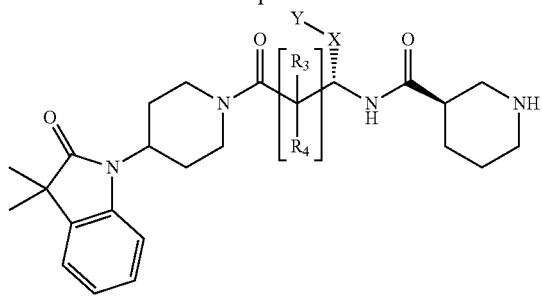

The following examples, EXAMPLE 82-88, were prepared according to the procedure described in the Step 2 through 3 of the EXAMPLE 21, using the appropriate amino acid precursor and (R)-1-(tert-butoxycarbonyl)piperidine-3-carboxylic acid instead of (S)-2-(tert-butoxycarbonylamino)-3-(4-chlorophenyl)propanoic acid and (1S,3R)-3-(tert-butoxycarbonyl(methyl)amino)cyclopentanecarboxylic acid, respectively.

TABLE 12-A

| Example | Structure | Chemical Name | HPLC Gradient Method | HPLC Retention Time (min.) | MS (ESI): m/z (M + H)+ |
|---|---|---|---|---|---|
| 82 | | (R)-N-((S)-1-(4-(3,3-dimethyl-2-oxoindolin-1-yl)piperidin-1-yl)-1-oxo-3-phenylpropan-2-yl)piperidine-3-carboxamide | Method C | 1.46 | 501 |
| 83 | | (R)-N-((S)-1-(4-(3,3-dimethyl-2-oxoindolin-1-yl)piperidin-1-yl)-3-(2-fluorophenyl)-1-oxo-propan-2-yl)piperidine-3-carboxamide | Method C | 1.47 | 519 |

TABLE 12-A-continued

| Example | Structure | Chemical Name | HPLC Gradient Method | HPLC Retention Time (min.) | MS (ESI): m/z (M + H)+ |
|---|---|---|---|---|---|
| 84 | | (R)-N-((S)-1-(4-(3,3-dimethyl-2-oxoindolin-1-yl)piperidin-1-yl)-3-(3-fluorophenyl)-1-oxo-propan-2-yl)piperidine-3-carboxamide | Method C | 1.48 | 519 |
| 85 | | (R)-N-((S)-1-(4-(3,3-dimethyl-2-oxoindolin-1-yl)piperidin-1-yl)-1-oxo-3-(2-(trifluoromethyl)phenyl)propan-2-yl)piperidine-3-carboxamide | Method C | 1.57 | 569 |
| 86 | | (R)-N-((S)-3-(2-chloro-phenyl)-1-(4-(3,3-dimethyl-2-oxoindolin-1-yl)piperidin-1-yl)-1-oxo-propan-2-yl)piperidine-3-carboxamide | Method C | 1.52 | 535 |

TABLE 12-B

| Example | Structure | Chemical Name | HPLC Gradient Method | HPLC Retention Time (min.) | MS (ESI): m/z (M + H)+ |
|---|---|---|---|---|---|
| 87 | 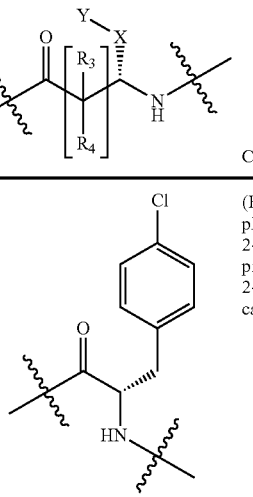 | (R)-N-((S)-3-(4-chloro-phenyl)-1-(4-(3,3-dimethyl-2-oxoindolin-1-yl)piperidin-1-yl)-1-oxopropan-2-yl)piperidine-3-carboxamide | Method C | 1.58 | 535 |

TABLE 12-B-continued

| Example | Structure | Chemical Name | HPLC Gradient Method | HPLC Retention Time (min.) | MS (ESI): m/z (M + H)+ |
|---|---|---|---|---|---|
| 88 | | (R)-N-((S)-1-(4-(3,3-dimethyl-2-oxoindolin-1-yl)piperidin-1-yl)-3,3-dimethyl-1-oxobutan-2-yl)piperidine-3-carboxamide | Method C | 1.44 | 467 |

Example 89

(S)—N—((S)-1-(4-(3,3-dimethyl-2-oxoindolin-1-yl)piperidin-1-yl)-1-oxo-3-phenylpropan-2-yl)-3-(methylamino)pyrrolidine-1-carboxamide

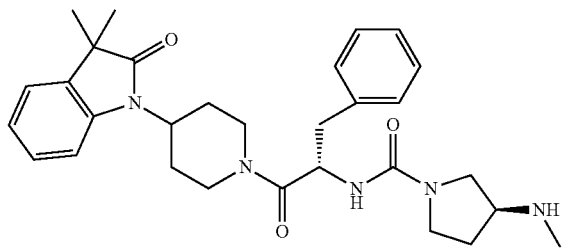 [SMILES: CN[C@H]1CCN(C(=O)N[C@@H](Cc2ccccc2)C(=O)N2CCC(N3C(=O)C(C)(C)c4ccccc43)CC2)C1]

Step 1.

(S)-1-(1-(2-amino-3-phenylpropanoyl)piperidin-4-yl)-3,3-dimethylindolin-2-one

The title compound was prepared according to the procedure described in the Step 2 of the EXAMPLE 21 using (S)-2-(tert-butoxycarbonylamino)-3-phenylpropanoic acid instead of (S)-2-(tert-butoxycarbonylamino)-3-(4-chlorophenyl)propanoic acid.

MS (ESI) m/z: 391 (M+H)+.

HPLC retention time: 1.52 min. (Method C).

Step 2.

(S)—N—((S)-1-(4-(3,3-dimethyl-2-oxoindolin-1-yl)piperidin-1-yl)-1-oxo-3-phenylpropan-2-yl)-3-(methylamino)pyrrolidine-1-carboxamide The title compound was prepared according to the procedure described in the EXAMPLE 47 using (S)-1-(1-(2-amino-3-phenylpropanoyl)piperidin-4-yl)-3,3-dimethylindolin-2-one instead of (S)-1-(1-(2-amino-4-phenylbutanoyl)piperidin-4-yl)-3,3-dimethylindolin-2-one hydrochloride.

MS (ESI) m/z: 516 (M+H)+.

HPLC retention time: 1.43 min. (Method C).

Example 90-94

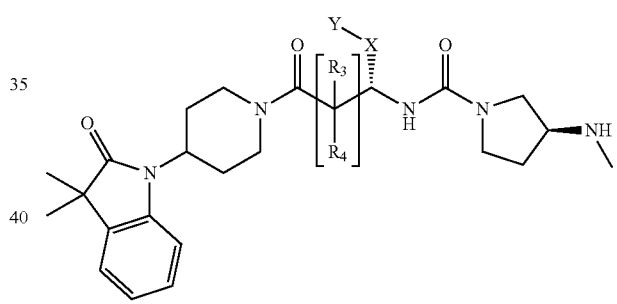

The following examples, EXAMPLE 90-94, were prepared according to the procedure described in the EXAMPLE 89, using the appropriate amino acid precursor instead of (S)-2-(tert-butoxycarbonylamino)-3-phenylpropanoic acid.

TABLE 13

| Example | Structure | Chemical Name | HPLC Gradient Method | HPLC Retention Time (min.) | MS (ESI): m/z (M + H)+ |
|---|---|---|---|---|---|
| 90 | | (S)-N-((S)-1-(4-(3,3-dimethyl-2-oxoindolin-1-yl)piperidin-1-yl)-3-(2-fluorophenyl)-1-oxopropan-2-yl)-3-(methylamino)pyrrolidine-1-caboxamide | Method C | 1.43 | 534 |

TABLE 13-continued

| Example | Structure | Chemical Name | HPLC Gradient Method | HPLC Retention Time (min.) | MS (ESI): m/z (M + H)+ |
|---|---|---|---|---|---|
| 91 | 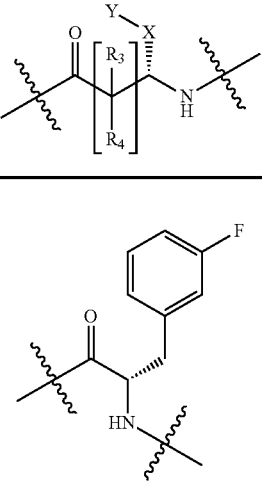 | (S)-N-((S)-1-(4-(3,3-dimethyl-2-oxoindolin-1-yl)piperidin-1-yl)-3-(3-fluorophenyl)-1-oxopropan-2-yl)-3-(methylamino)pyrrolidine-1-carboxamide | Method C | 1.44 | 534 |
| 92 | 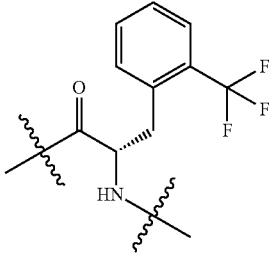 [SMILES: *N[C@@H](Cc1ccccc1C(F)(F)F)C(*)=O] | (S)-N-((S)-1-(4-(3,3-dimethyl-2-oxoindolin-1-yl)piperidin-1-yl)-1-oxo-3-(2-(trifluoromethyl)phenyl)propan-2-yl)-3-(methylamino)pyrrolidine-1-carboxamide | Method C | 1.53 | 584 |
| 93 | 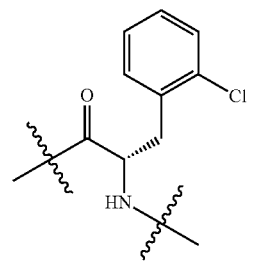 [SMILES: *N[C@@H](Cc1ccccc1Cl)C(*)=O] | (S)-N-((S)-3-(2-chlorophenyl)-1-(4-(3,3-dimethyl-2-oxoindolin-1-yl)piperidin-1-yl)-1-oxopropan-2-yl)-3-(methylamino)pyrrolidine-1-carboxamide | Method C | 1.48 | 550 |
| 94 | 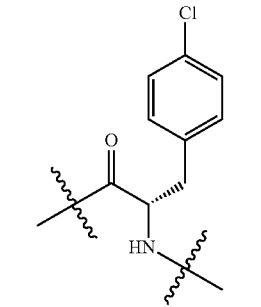 [SMILES: *N[C@@H](Cc1ccc(Cl)cc1)C(*)=O] | (S)-N-((S)-3-(4-chlorophenyl)-1-(4-(3,3-dimethyl-2-oxoindolin-1-yl)piperidin-1-yl)-1-oxopropan-2-yl)-3-(methylamino)pyrrolidine-1-carboxamide | Method C | 1.52 | 550 |

Example 95-97

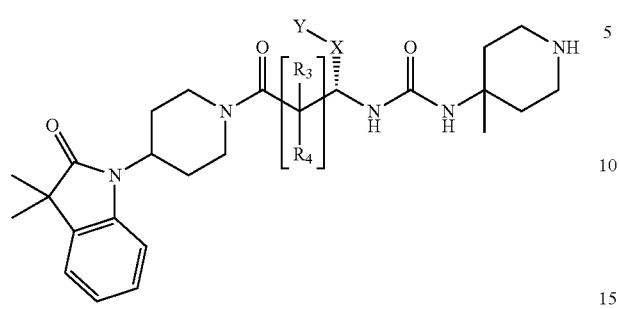

The following examples, EXAMPLE 95-97, were prepared according to the procedure described in EXAMPLE 89, using the appropriate amino acid precursor and tert-butyl 4-amino-4-methylpiperidine-1-carboxylate instead of (S)-2-(tert-butoxycarbonylamino)-3-phenylpropanoic acid and (S)-tert-butyl methyl(pyrrolidin-3-yl)carbamate, respectively.

Example 98

(S)—N—((R)-1-(4-(3,3-dimethyl-2-oxoindolin-1-yl)piperidin-1-yl)-1-oxo-4-phenylbutan-2-yl)-3-(methylamino)pyrrolidine-1-carboxamide

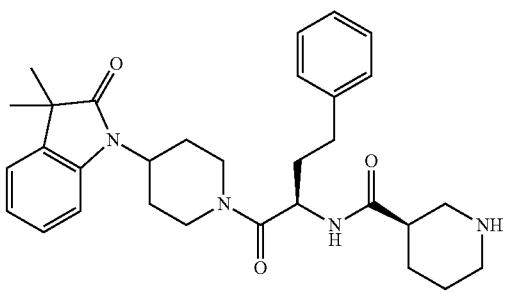 [SMILES: CC1(C)C(=O)N(C2CCN(C(=O)[C@@H](CCc3ccccc3)NC(=O)[C@@H]3CCCNC3)CC2)c2ccccc21]

The title compound was prepared according to the procedure similar to that described in the Step 2 through 3 of the EXAMPLE 21 using (R)-2-(tert-butoxycarbonylamino)-4-

TABLE 14

| Example | Structure | Chemical Name | HPLC Gradient Method | HPLC Retention Time (min.) | MS (ESI): m/z (M + H)+ |
|---|---|---|---|---|---|
| 95 | | (S)-1-(1-(4-(3,3-dimethyl-2-oxoindolin-1-yl)piperidin-1-yl)-1-oxo-3-(2-(trifluoromethyl)phenyl)propan-2-yl)-3-(4-methylpiperidin-4-yl)urea | Method C | 1.52 | 598 |
| 96 | | (S)-1-(3-(2-chlorophenyl)-1-(4-(3,3-dimethyl-2-oxoindolin-1-yl)piperidin-1-yl)-1-oxopropan-2-yl)-3-(4-methylpiperidin-4-yl)urea | Method C | 1.48 | 564 |
| 97 | | (S)-1-(3-(4-chlorophenyl)-1-(4-(3,3-dimethyl-2-oxoindolin-1-yl)piperidin-1-yl)-1-oxopropan-2-yl)-3-(4-methylpiperidin-4-yl)urea | Method C | 1.51 | 564 | phenylbutanoic acid and (R)-1-(tert-butoxycarbonyl)piperidine-3-carboxylic acid instead of (S)-2-(tert-butoxycarbonylamino)-3-(4-chlorophenyl)propanoic acid and (1S,3R)-3-(tert-butoxycarbonyl(methyl)amino)cyclopentanecarboxylic acid, respectively.
MS (ESI) m/z: 517 (M+H)+.
HPLC retention time: 1.50 min (Method C).

Example 99

(S)—N—((R)-1-(4-(3,3-dimethyl-2-oxoindolin-1-yl)piperidin-1-yl)-1-oxo-4-phenylbutan-2-yl)-3-(methylamino)pyrrolidine-1-carboxamide

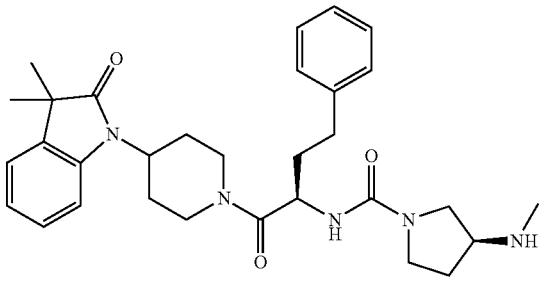 [SMILES: CN[C@H]1CCN(C(=O)N[C@H](CCc2ccccc2)C(=O)N2CCC(N3C(=O)C(C)(C)c4ccccc43)CC2)C1]

Step 1.

(R)-1-(1-(2-amino-4-phenylbutanoyl)piperidin-4-yl)-3,3-dimethylindolin-2-one

The title compound was prepared according to the procedure similar to that described in the Step 3 through 4 of the EXAMPLE 1 using (R)—N-tert-butoxycarbonyl-homophenylalanine instead of (S)—N-tert-butoxycarbonyl-homophenylalanine.
MS (ESI) m/z: 406 (M+H)+.
Step 2.

(S)—N—((R)-1-(4-(3,3-dimethyl-2-oxoindolin-1-yl)piperidin-1-yl)-1-oxo-4-phenylbutan-2-yl)-3-(methylamino)pyrrolidine-1-carboxamide The title compound was prepared according to the procedure similar to that described in the Step 1 of the EXAMPLE 47 using (R)-1-(1-(2-amino-4-phenylbutanoyl)piperidin-4-yl)-3,3-dimethylindolin-2-one (EXAMPLE 76, Step 1) instead of (S)-1-(1-(2-amino-4-phenylbutanoyl)piperidin-4-yl)-3,3-dimethylindolin-2-one.
MS (ESI) m/z: 532 (M+H)+.
HPLC retention time: 1.49 min (Method C).

GPR38 (Motilin Receptor) Functional Assay

A CHO-K1 cell line stably transfected NFAT-beta-lactamase reporter and human motilin receptor gene was used. The cells were cultured in culture medium (Dulbecco's modified eagle medium containing 10% fetal bovine serum, 1 mM sodium pyruvate, 0.1 mM MEM nonessential amino acids, 25 mM HEPES buffer, 50 units/mL penicillin, 50 microg/mL streptomycin, 100 microg/mL zeocin, and 500 microg/mL G418). The cells were harvested with 0.05% trypsin EDTA and centrifuged. The cell pellets were resuspended in the culture medium and plated into a black/clear bottom 384-well plate at a density of 8000 cells per well, then incubated at 37° C. with 5% $CO_2$ for over night (about 20 hours). On the day of assay, the culture medium was aspirated and 20 microL of assay medium (Dulbecco's modified eagle medium containing 100 units/mL penicillin and 100 microg/mL streptomycin) was added to each well, then the cell plates were placed in incubator at 37° C. with 5% $CO_2$ for 1.5 hours. Compounds were prepared in 100% DMSO and these were diluted to 5× of final concentration with assay buffer (Hanks balanced salt solution, 20 mM HEPES, and 0.1% BSA), then dispensed into 384-well plate (5 microL/well). After incubation at 37° C. with 5% $CO_2$ for 4.5 hours, CCF4-AM loading solution (Invitrogen Corp.) was added to each well. After incubation for 2 hours at room temperature, fluorescence intensities were measured by using plate reader FDSS (Hamamatsu Photonics K. K.) with excitation 400 nm, emission 465 nm/540 nm. Agonistic activity ($EC_{50}$) was calculated from the sigmoidal dose-response curve using GraphPad Prism software (GraphPad Software, Inc.).

Example 1-97 of the invention have an EC50=<100 nM in the functional assay described above.

Example 1-3, 6-7, 9-10, 12-15, 17, 20-39, 43-57, 60-65, 67-72, 78-80, 82-87 and 91-94 of the invention have an EC50=<10 nM in the functional assay described above.

As shown in the table below, functional activity toward GPR38 (motilin receptor) was influenced by the absolute configuration of the amino acid linker moiety as much as 100-10000 fold.

TABLE 15

| Example | Structure | Amino Acid Linker | Absolute Configuration | ED50 (nM) |
|---|---|---|---|---|
| 1 | 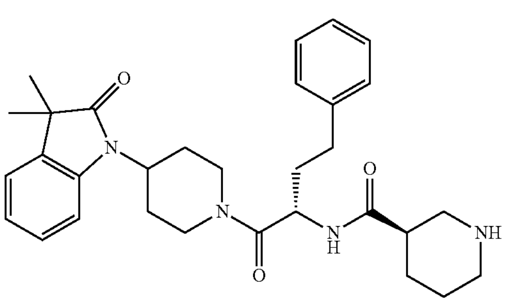 [SMILES: CC1(C)C(=O)N(C2CCN(C(=O)[C@H](CCc3ccccc3)NC(=O)[C@@H]3CCCNC3)CC2)c2ccccc21] | | (S) | 0.24 |

TABLE 15-continued

| Example | Structure | Amino Acid Linker | Absolute Configuration | ED50 (nM) |
|---------|-----------|-------------------|------------------------|-----------|
| 98 | 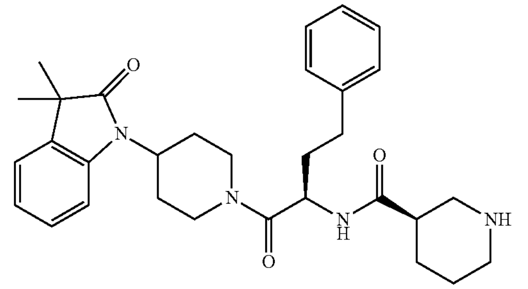 [SMILES: CC1(C)C(=O)N(C2CCN(C(=O)[C@@H](CCc3ccccc3)NC(=O)[C@@H]3CCCNC3)CC2)c2ccccc21] | | (R) | 6211 |
| 47 | 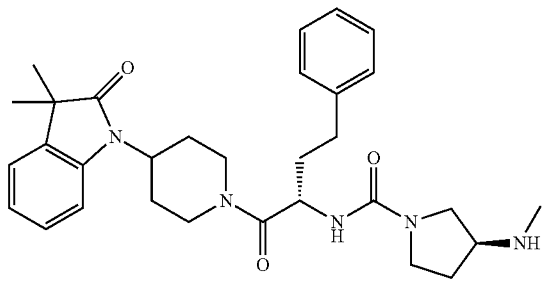 [SMILES: CN[C@H]1CCN(C(=O)N[C@@H](CCc2ccccc2)C(=O)N2CCC(N3C(=O)C(C)(C)c4ccccc43)CC2)C1] | | (S) | 0.98 |
| 99 | 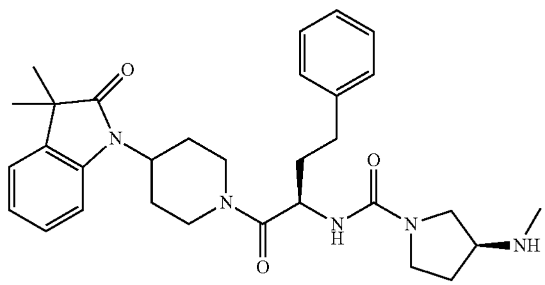 [SMILES: CN[C@H]1CCN(C(=O)N[C@H](CCc2ccccc2)C(=O)N2CCC(N3C(=O)C(C)(C)c4ccccc43)CC2)C1] | | (R) | 488 |

PAM PA (Parallel Artificial Membrane Permeation Assay)

Experiments were performed in 96-well acceptor and donor plates. Such 96-well system was described in J. Med. Chem., 1998, 41, 1007. As artificial membrane material were used 4% phosphatidylcholine and 1% stearic acid in dodecane. The acceptor plate (96 well hydrophobic filter plate (MAIPN45, Millipore)) was prepared by adding 5 pL of artificial membrane material on the top of the filter and the plate was filled with 250 pL of 2-(N-morpholino)ethanesulfonic acid (MES) buffered Hank's balanced salt solution (HBSS) (pH 6.5). The donor plate (Transport Receiver plate (MATRNPS50, Millipore)) was filled 35 with 300 pL of MES buffered HBSS (pH 6.5) containing 10 pM of the test compounds. The acceptor plate was placed onto the donor plate to form a "sandwich" and was incubated at 30° C. for 2.5 hours. After the incubation period, acceptor, donor and initial donor solution (reference) were analyzed via LC-MS/MS.

Data were reported as the effective permeability value (Pe) in cm×10$^{-6}$/sec and the membrane retention value.

Example 1, 3-4, 6-7, 13, 17, 20, 22-23, 29, 35-36, 39, 44, 47-48, 50, 54, 64-66, 68-70, 73-74, 85 and 92-94 of the invention have a Pe>=2.0 cm×10$^{-6}$/sec in the permeation assay described above.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A compound of the following formula (I):

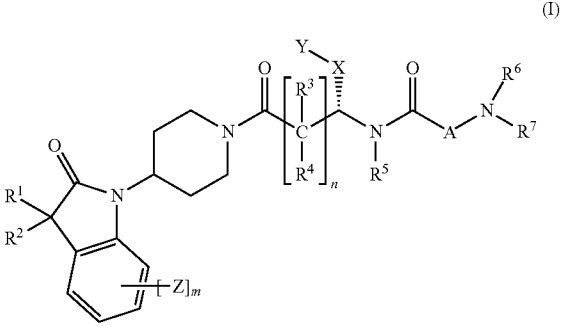

wherein $R^1$ and $R^2$ are independently selected from the group consisting of hydrogen, $C_1$-$C_4$ alkyl, and $C_3$-$C_7$ cycloalkyl;

or alternatively $R^1$ and $R^2$, together with the atoms to which they are attached, form a 3 to 6 membered ring which may contain oxygen; said ring is optionally substituted with 1 to 4 substituents independently selected from the group consisting of halogen, hydroxy, $C_1$-$C_4$ alkyl, and $C_1$-$C_4$ alkoxy;

$R^3$ and $R^4$ are independently hydrogen or $C_1$-$C_4$ alkyl;

$R^5$ is hydrogen, $C_1$-$C_4$ alkyl, or $C_1$-$C_4$ alkoxy $C_1$-$C_4$ alkyl;

$R^6$ and $R^7$ are independently selected from hydrogen, $C_1$-$C_4$ alkyl, hydroxy $C_1$-$C_4$ alkyl, $C_1$-$C_4$ alkoxy $C_1$-$C_4$ alkyl, amino $C_1$-$C_4$ alkyl, $C_1$-$C_4$ alkyl amino $C_1$-$C_4$ alkyl, di($C_1$-$C_4$ alkyl)amino $C_1$-$C_4$ alkyl, saturated heterocyclyl, and saturated heterocyclyl $C_1$-$C_4$ alkyl; said saturated heterocyclyl and alkyl may have independently 1 to 4 $C_1$-$C_4$ alkyl; or alternatively $R^6$ and $R^7$ together with nitrogen atom to which they are attached form a 4 to 6 membered ring which may contain nitrogen or oxygen, wherein the 4 to 6 membered ring is optionally substituted with 1 to 4 substituents independently selected from the group consisting of hydroxy, $C_1$-$C_4$ alkyl, $C_1$-$C_4$ alkoxy, $C_3$-$C_7$ cycloalkyl, amino, $C_1$-$C_4$ alkylamino, and di($C_1$-$C_4$ alkyl)amino;

A is

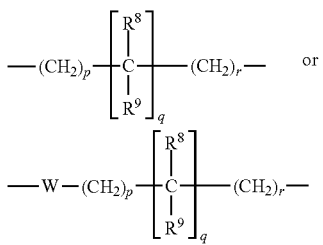

{Chem. 2} where p, q, and r are independently 0, 1, 2 or 3;

$R^8$ and $R^9$ are independently hydrogen, $C_1$-$C_6$ alkyl or $C_3$-$C_7$ cycloalkyl; said alkyl and cycloalkyl are optionally substituted with hydroxy, $C_1$-$C_4$ alkyl, amino, $C_1$-$C_4$ alkylamino, and di($C_1$-$C_4$ alkyl)amino; or $R^8$ and $R^9$ may be joined to one another to form a $C_3$-$C_7$ membered ring which may contain oxygen; or $R^8$ and $R^9$ may independently be joined to one or both of $R^8$ and $R^9$ groups to form alkylene bridges between the terminal nitrogen and the alkyl portion of the $R^8$ or $R^9$ groups, wherein the bridge contains 1 to 5 carbons atoms and may contain nitrogen or oxygen; said bridge is optionally substituted with 1 to 4 substituents independently selected from the group consisting of halogen, hydroxy, $C_1$-$C_4$ alkyl, halo $C_1$-$C_4$ alkyl, and $C_1$-$C_4$ alkoxy;

W is N—$R^{10}$, said $R^{10}$ is hydrogen or $C_1$-$C_4$ alkyl;

X is $C_0$-$C_4$ alkylene, or $C_0$-$C_4$ alkylene-K—$C_0$-$C_4$ alkylene, where K is —O—, —NH—, $NR^9$—, —S—, —SO—, —SO$_2$—, —CO—, —OCO—, —C(O)O—, —$CR^{10}$=$CR^{12}$—,

—C≡C—,

—$NR^{11}$CO—, or —$CONR^{11}$—; said alkylene is optionally substituted with $C_1$-$C_4$ alkyl, hydroxy $C_1$-$C_4$ alkyl, amino $C_1$-$C_4$ alkyl, $C_1$-$C_4$ alkyl amino $C_1$-$C_4$ alkyl, di($C_1$-$C_4$)alkylamino $C_1$-$C_4$ alkyl, or $C_1$-$C_4$ alkoxy $C_1$-$C_4$ alkyl;

$R^{11}$ is hydrogen or $C_1$-$C_4$ alkyl;

Y is hydrogen, halogen, or 5-10 membered ring; said ring is optionally substituted with hydroxy, halogen, halo $C_1$-$C_4$ alkyl, $C_1$-$C_4$ alkyl, hydroxy $C_1$-$C_4$ alkyl, amino $C_1$-$C_4$ alkyl, $C_1$-$C_4$ alkoxy, or $C_1$-$C_4$ alkoxy $C_1$-$C_4$ alkyl;

Z is halogen, $C_1$-$C_4$ alkyl, $C_1$-$C_4$ alkoxy, or hydroxy;

m is 0, 1, 2, 3, or 4;

n is 0, 1, or 2;

or a pharmaceutically acceptable salt thereof.

2. The compound or the pharmaceutically acceptable salt thereof, as claimed in claim 1, wherein:

$R^5$ is hydrogen or $C_1$-$C_4$ alkyl;

X is $C_0$-$C_4$ alkylene, or $C_0$-$C_4$ alkylene-K—$C_0$-$C_4$ alkylene, where K is —O—, —NH— or $NR^9$—; said alkylene is optionally substituted with $C_1$-$C_4$ alkyl, hydroxy $C_1$-$C_4$ alkyl, or $C_1$-$C_4$ alkoxy $C_1$-$C_4$ alkyl;

Y is hydrogen or 5-10 membered ring; said ring is optionally substituted with hydroxy, halogen, halo $C_1$-$C_4$ alkyl, $C_1$-$C_4$ alkyl, hydroxy $C_1$-$C_4$ alkyl, $C_1$-$C_4$ alkoxy, or $C_1$-$C_4$ alkoxy $C_1$-$C_4$ alkyl;

m is 0, 1, or 2; and n is 0 or 1.

3. A compound selected from the group consisting of:

(R)—N—((S)-1-(4-(3,3-dimethyl-2-oxoindolin-1-yl)piperidin-1-yl)-1-oxo-4-phenylbutan-2-yl)piperidine-3-carboxamide;

(S)—N—((S)-1-(4-(3,3-dimethyl-2-oxoindolin-1-yl)piperidin-1-yl)-1-oxo-4-phenylbutan-2-yl)piperidine-2-carboxamide;

(S)-2-amino-N—((S)-1-(4-(3,3-dimethyl-2-oxoindolin-1-yl)piperidin-1-yl)-1-oxo-4-phenylbutan-2-yl)-3,3-dimethylbutanamide;

(S)-2-(1-aminocyclobutyl)-N-(1-(4-(3,3-dimethyl-2-oxoindolin-1-yl)piperidin-1-yl)-1-oxo-4-phenylbutan-2-yl)acetamide;

(S)-1-(aminomethyl)-N-(1-(4-(3,3-dimethyl-2-oxoindolin-1-yl)piperidin-1-yl)-1-oxo-4-phenylbutan-2-yl)cyclopropanecarboxamide;

(S)—N-(1-(4-(3,3-dimethyl-2-oxoindolin-1-yl)piperidin-1-yl)-1-oxo-4-phenylbutan-2-yl)azetidine-3-carboxamide;

(S)—N-(1-(4-(3,3-dimethyl-2-oxoindolin-1-yl)piperidin-1-yl)-1-oxo-4-phenylbutan-2-yl)piperidine-4-carboxamide;

(S)-2-(1-aminocyclopentyl)-N-(1-(4-(3,3-dimethyl-2-oxoindolin-1-yl)piperidin-1-yl)-1-oxo-4-phenylbutan-2-yl)acetamide;

(S)—N-(1-(4-(3,3-dimethyl-2-oxoindolin-1-yl)piperidin-1-yl)-1-oxo-4-phenylbutan-2-yl)-3-methyl-3-(methylamino)butanamide;

(S)-3-(cyclopentylamino)-N-(1-(4-(3,3-dimethyl-2-oxoindolin-1-yl)piperidin-1-yl)-1-oxo-4-phenylbutan-2-yl)propanamide;

(S)—N-(1-(4-(3,3-dimethyl-2-oxoindolin-1-yl)piperidin-1-yl)-1-oxo-4-phenylbutan-2-yl)-3-((2-methoxyethyl)(methyl)amino)propanamide;

(S)—N-(1-(4-(3,3-dimethyl-2-oxoindolin-1-yl)piperidin-1-yl)-1-oxo-4-phenylbutan-2-yl)-2-(pyrrolidin-1-yl)acetamide;

(R)—N—((S)-1-(4-(3,3-dimethyl-2-oxoindolin-1-yl)piperidin-1-yl)-1-oxo-4-phenylbutan-2-yl)-1-methylpiperidine-3-carboxamide;

(1S,3R)—N—((S)-3-(4-chlorophenyl)-1-(4-(3,3-dimethyl-2-oxoindolin-1-yl)piperidin-1-yl)-1-oxopropan-2-yl)-3-(methylamino)cyclopentanecarboxamide;

(1S,3R)—N—((S)-1-(4-(3,3-dimethyl-2-oxoindolin-1-yl)piperidin-1-yl)-1-oxo-3-(2-(trifluoromethyl)phenyl)propan-2-yl)-3-(methylamino)cyclopentanecarboxamide;

(1S,3R)—N—((S)-3-cyclohexyl-1-(4-(3,3-dimethyl-2-oxoindolin-1-yl)piperidin-1-yl)-1-oxopropan-2-yl)-3-(methylamino)cyclopentanecarboxamide;

(1S,3R)—N—((S)-1-(4-(3,3-dimethyl-2-oxoindolin-1-yl)piperidin-1-yl)-3-(naphthalen-1-yl)-1-oxopropan-2-yl)-3-(methylamino)cyclopentanecarboxamide;

(1S,3R)—N—((S)-3-(2-chlorophenyl)-1-(4-(3,3-dimethyl-2-oxoindolin-1-yl)piperidin-1-yl)-1-oxopropan-2-yl)-3-(methylamino)cyclopentanecarboxamide;

(1S,3R)—N—((S)-1-(4-(3,3-dimethyl-2-oxoindolin-1-yl)piperidin-1-yl)-1-oxo-3-o-tolylpropan-2-yl)-3-(methylamino)cyclopentanecarboxamide;

(1S,3R)—N—((S)-1-(4-(3,3-dimethyl-2-oxoindolin-1-yl)piperidin-1-yl)-3-(4-fluorophenyl)-1-oxopropan-2-yl)-3-(methylamino)cyclopentanecarboxamide;

(1S,3R)—N—((S)-1-(4-(3,3-dimethyl-2-oxoindolin-1-yl)piperidin-1-yl)-3-(3-fluorophenyl)-1-oxopropan-2-yl)-3-(methylamino)cyclopentanecarboxamide;

(1S,3R)—N—((S)-3-(3-chlorophenyl)-1-(4-(3,3-dimethyl-2-oxoindolin-1-yl)piperidin-1-yl)-1-oxopropan-2-yl)-3-(methylamino)cyclopentanecarboxamide;

(1S,3R)—N—((S)-1-(4-(3,3-dimethyl-2-oxoindolin-1-yl)piperidin-1-yl)-1-oxo-3-phenylpropan-2-yl)-3-(methylamino)cyclopentanecarboxamide;

(1S,3R)—N—((S)-1-(4-(3,3-dimethyl-2-oxoindolin-1-yl)piperidin-1-yl)-3-(3-methoxyphenyl)-1-oxopropan-2-yl)-3-(methylamino)cyclopentanecarboxamide;

(1S,3R)—N—((S)-1-(4-(3,3-dimethyl-2-oxoindolin-1-yl)piperidin-1-yl)-3-(2-fluorophenyl)-1-oxopropan-2-yl)-3-(methylamino)cyclopentanecarboxamide;

(1S,3R)—N—((S)-1-(4-(3,3-dimethyl-2-oxoindolin-1-yl)piperidin-1-yl)-4-methyl-1-oxopentan-2-yl)-3-(methylamino)cyclopentanecarboxamide;

(1S,3R)—N—((S)-1-(4-(3,3-dimethyl-2-oxoindolin-1-yl)piperidin-1-yl)-3-(1H-indol-3-yl)-1-oxopropan-2-yl)-3-(methylamino)cyclopentanecarboxamide;

(1S,3R)—N—((S)-1-(4-(3,3-dimethyl-2-oxoindolin-1-yl)piperidin-1-yl)-1-oxo-3-(3-(trifluoromethyl)phenyl)propan-2-yl)-3-(methylamino)cyclopentanecarboxamide;

(1S,3R)—N—((S)-1-(4-(3,3-dimethyl-2-oxoindolin-1-yl)piperidin-1-yl)-1-oxo-3-(4-(trifluoromethyl)phenyl)propan-2-yl)-3-(methylamino)cyclopentanecarboxamide;

(1S,3R)—N—((S)-1-(4-(3,3-dimethyl-2-oxoindolin-1-yl)piperidin-1-yl)-3-(4-methoxyphenyl)-1-oxopropan-2-yl)-3-(methylamino)cyclopentanecarboxamide;

(1S,3R)—N—((S)-1-(4-(3,3-dimethyl-2-oxoindolin-1-yl)piperidin-1-yl)-1-oxo-3-phenoxypropan-2-yl)-3-(methylamino)cyclopentanecarboxamide;

(1S,3R)—N—((S)-3-(2-chlorophenoxy)-1-(4-(3,3-dimethyl-2-oxoindolin-1-yl)piperidin-1-yl)-1-oxopropan-2-yl)-3-(methylamino)cyclopentanecarboxamide;

(1S,3R)—N—((S)-4-(4-(3,3-dimethyl-2-oxoindolin-1-yl)piperidin-1-yl)-4-oxo-1-phenylbutan-2-yl)-3-(methylamino)cyclopentanecarboxamide;

(R)—N—((S)-1-(4-(5-fluoro-3,3-dimethyl-2-oxoindolin-1-yl)piperidin-1-yl)-1-oxo-4-phenylbutan-2-yl)piperidine-3-carboxamide;

(1S,3R)—N—((S)-1-(4-(5-fluoro-3,3-dimethyl-2-oxoindolin-1-yl)piperidin-1-yl)-1-oxo-4-phenylbutan-2-yl)-3-(methylamino)cyclopentanecarboxamide;

(S)—N-(1-(4-(5-fluoro-3,3-dimethyl-2-oxoindolin-1-yl)piperidin-1-yl)-1-oxo-4-phenylbutan-2-yl)-3-methyl-3-(methylamino)butanamide;

(S)—N—((S)-1-(4-(3,3-dimethyl-2-oxoindolin-1-yl)piperidin-1-yl)-1-oxo-4-phenylbutan-2-yl)-3-(methylamino)pyrrolidine-1-carboxamide;

1-((S)-1-(4-(3,3-dimethyl-2-oxoindolin-1-yl)piperidin-1-yl)-1-oxo-4-phenylbutan-2-yl)-3-((S)-pyrrolidin-2-ylmethyl)urea;

1-((S)-1-(4-(3,3-dimethyl-2-oxoindolin-1-yl)piperidin-1-yl)-1-oxo-4-phenylbutan-2-yl)-3-((R)-piperidin-3-yl)urea;

3-((S)-1-(4-(3,3-dimethyl-2-oxoindolin-1-yl)piperidin-1-yl)-1-oxo-4-phenylbutan-2-yl)-1-methyl-1-((S)-pyrrolidin-2-ylmethyl)urea;

1-((S)-1-(4-(3,3-dimethyl-2-oxoindolin-1-yl)piperidin-1-yl)-1-oxo-4-phenylbutan-2-yl)-3-((R)-pyrrolidin-2-ylmethyl)urea;

1-((S)-1-(4-(3,3-dimethyl-2-oxoindolin-1-yl)piperidin-1-yl)-1-oxo-4-phenylbutan-2-yl)-3-((R)-pyrrolidin-3-yl)urea;

1-((S)-1-(4-(3,3-dimethyl-2-oxoindolin-1-yl)piperidin-1-yl)-1-oxo-4-phenylbutan-2-yl)-3-((R)-pyrrolidin-3-ylmethyl)urea;

(R)—N—((S)-1-(4-(3,3-dimethyl-2-oxoindolin-1-yl)piperidin-1-yl)-1-oxo-4-phenylbutan-2-yl)-3-methylpiperazine-1-carboxamide;

(S)-1-(1-(4-(3,3-dimethyl-2-oxoindolin-1-yl)piperidin-1-yl)-1-oxo-4-phenylbutan-2-yl)-3-(4-ethylpiperidin-4-yl)urea;

(S)-1-(1-(4-(3,3-dimethyl-2-oxoindolin-1-yl)piperidin-1-yl)-1-oxo-4-phenylbutan-2-yl)-3-(4-methylpiperidin-4-yl)urea;

1-((S)-1-(4-(3,3-dimethyl-2-oxoindolin-1-yl)piperidin-1-yl)-1-oxo-4-phenylbutan-2-yl)-3-((S)-pyrrolidin-3-yl)urea;

1-((S)-1-(4-(3,3-dimethyl-2-oxoindolin-1-yl)piperidin-1-yl)-1-oxo-4-phenylbutan-2-yl)-3-((S)-piperidin-2-ylmethyl)urea;

1-((S)-1-(4-(3,3-dimethyl-2-oxoindolin-1-yl)piperidin-1-yl)-1-oxo-4-phenylbutan-2-yl)-3-((R)-piperidin-3-ylmethyl)urea;

(S)-1-(2-amino-2-methylpropyl)-3-(1-(4-(3,3-dimethyl-2-oxoindolin-1-yl)piperidin-1-yl)-1-oxo-4-phenylbutan-2-yl)urea;

(S)-3-(cyclopropyl(methyl)amino)-N—((S)-1-(4-(3,3-dimethyl-2-oxoindolin-1-yl)piperidin-1-yl)-1-oxo-4-phenylbutan-2-yl)pyrrolidine-1-carboxamide;

(S)-1-(1-(4-(3,3-dimethyl-2-oxoindolin-1-yl)piperidin-1-yl)-1-oxo-4-phenylbutan-2-yl)-3-(2-(pyrrolidin-1-yl)ethyl)urea;

(S)-1-(1-(4-(3,3-dimethyl-2-oxoindolin-1-yl)piperidin-1-yl)-1-oxo-4-phenylbutan-2-yl)-3-(2-(dimethylamino)ethyl)urea;

(S)—N—((S)-1-(4-(3,3-dimethyl-2-oxoindolin-1-yl)piperidin-1-yl)-1-oxo-4-phenylbutan-2-yl)-3-(dimethylamino)pyrrolidine-1-carboxamide;

1-((S)-1-(4-(3,3-dimethyl-2-oxoindolin-1-yl)piperidin-1-yl)-1-oxo-4-phenylbutan-2-yl)-3-(((S)-1-methylpyrrolidin-2-yl)methyl)urea;

(S)-1-(1-(4-(3,3-dimethyl-2-oxoindolin-1-yl)piperidin-1-yl)-1-oxo-4-phenylbutan-2-yl)-3-(1,4-dimethylpiperidin-4-yl)urea;

(S)—N—((S)-1-(4-(5-fluoro-3,3-dimethyl-2-oxoindolin-1-yl)piperidin-1-yl)-1-oxo-4-phenylbutan-2-yl)-3-(methylamino)pyrrolidine-1-carboxamide;

1-((S)-1-(4-(5-fluoro-3,3-dimethyl-2-oxoindolin-1-yl)piperidin-1-yl)-1-oxo-4-phenylbutan-2-yl)-3-((S)-pyrrolidin-2-ylmethyl)urea;

(S)-1-(1-(4-(5-fluoro-3,3-dimethyl-2-oxoindolin-1-yl)piperidin-1-yl)-1-oxo-4-phenylbutan-2-yl)-3-(4-methylpiperidin-4-yl)urea;

(S)—N-(1-(4-(3,3-dimethyl-2-oxoindolin-1-yl)piperidin-1-yl)-1-oxo-3-(2-(trifluoromethyl)phenyl)propan-2-yl)piperidine-4-carboxamide;

(S)—N-(3-(2-chlorophenyl)-1-(4-(3,3-dimethyl-2-oxoindolin-1-yl)piperidin-1-yl)-1-oxopropan-2-yl)piperidine-4-carboxamide;

(S)—N-(3-(4-chlorophenyl)-1-(4-(3,3-dimethyl-2-oxoindolin-1-yl)piperidin-1-yl)-1-oxopropan-2-yl)piperidine-4-carboxamide;

(R)—N—((S)-1-(4-(3,3-dimethyl-2-oxoindolin-1-yl)piperidin-1-yl)-1-oxo-3-phenylpropan-2-yl)piperidine-3-carboxamide;

(R)—N—((S)-1-(4-(3,3-dimethyl-2-oxoindolin-1-yl)piperidin-1-yl)-3-(2-fluorophenyl)-1-oxopropan-2-yl)piperidine-3-carboxamide;

(R)—N—((S)-1-(4-(3,3-dimethyl-2-oxoindolin-1-yl)piperidin-1-yl)-3-(3-fluorophenyl)-1-oxopropan-2-yl)piperidine-3-carboxamide;

(R)—N—((S)-1-(4-(3,3-dimethyl-2-oxoindolin-1-yl)piperidin-1-yl)-1-oxo-3-(2-(trifluoromethyl)phenyl)propan-2-yl)piperidine-3-carboxamide;

(R)—N—((S)-3-(2-chlorophenyl)-1-(4-(3,3-dimethyl-2-oxoindolin-1-yl)piperidin-1-yl)-1-oxopropan-2-yl)piperidine-3-carboxamide;

(R)—N—((S)-3-(4-chlorophenyl)-1-(4-(3,3-dimethyl-2-oxoindolin-1-yl)piperidin-1-yl)-1-oxopropan-2-yl)piperidine-3-carboxamide;

(S)—N—((S)-1-(4-(3,3-dimethyl-2-oxoindolin-1-yl)piperidin-1-yl)-3-(3-fluorophenyl)-1-oxopropan-2-yl)-3-(methylamino)pyrrolidine-1-carboxamide;

(S)—N—((S)-1-(4-(3,3-dimethyl-2-oxoindolin-1-yl)piperidin-1-yl)-1-oxo-3-(2-(trifluoromethyl)phenyl)propan-2-yl)-3-(methylamino)pyrrolidine-1-carboxamide;

(S)—N—((S)-3-(2-chlorophenyl)-1-(4-(3,3-dimethyl-2-oxoindolin-1-yl)piperidin-1-yl)-1-oxopropan-2-yl)-3-(methylamino)pyrrolidine-1-carboxamide; and (S)—N—((S)-3-(4-chlorophenyl)-1-(4-(3,3-dimethyl-2-oxoindolin-1-yl)piperidin-1-yl)-1-oxopropan-2-yl)-3-(methylamino)pyrrolidine-1-carboxamide;

or a pharmaceutically acceptable salt thereof.

4. A pharmaceutical composition comprising the compound or the pharmaceutically acceptable salt thereof, as claimed in claim 1, and a pharmaceutically acceptable carrier.

5. A pharmaceutical composition as claimed in claim 4, further comprising another pharmacologically active agent.

* * * * *

UNITED STATES PATENT AND TRADEMARK OFFICE
CERTIFICATE OF CORRECTION

PATENT NO.         : 8,697,877 B2                        Page 1 of 1
APPLICATION NO.    : 13/203301
DATED              : April 15, 2014
INVENTOR(S)        : Sudo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 133 days.

Signed and Sealed this

Twenty-ninth Day of September, 2015

Michelle K. Lee
*Director of the United States Patent and Trademark Office*